United States Patent
Gomez-Galeno et al.

(10) Patent No.: US 10,221,130 B2
(45) Date of Patent: *Mar. 5, 2019

(54) GLUCAGON ANTAGONISTS

(71) Applicant: Metabasis Therapeutics, Inc., San Diego, CA (US)

(72) Inventors: Jorge E. Gomez-Galeno, San Diego, CA (US); Scott J. Hecker, Del Mar, CA (US); Qun Dang, San Diego, CA (US); Mali Venkat Reddy, San Diego, CA (US); Zhili Sun, San Diego, CA (US); Matthew P. Grote, Carlsbad, CA (US); Thanh Huu Nguyen, Solana Beach, CA (US); Robert Huerta Lemus, Escondido, CA (US); Haiqing Li, San Diego, CA (US)

(73) Assignee: Metabasis Therapeutics, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/721,556

(22) Filed: Sep. 29, 2017

(65) Prior Publication Data

US 2018/0022695 A1  Jan. 25, 2018

Related U.S. Application Data

(63) Continuation of application No. 14/555,503, filed on Nov. 26, 2014, now Pat. No. 9,783,494, which is a continuation of application No. 13/058,604, filed as application No. PCT/US2009/053795 on Aug. 13, 2009, now Pat. No. 8,907,103.

(60) Provisional application No. 61/088,697, filed on Aug. 13, 2008.

(51) Int. Cl.
| | |
|---|---|
| C07C 309/15 | (2006.01) |
| C07D 263/57 | (2006.01) |
| A61K 31/185 | (2006.01) |
| A61K 31/423 | (2006.01) |
| A61K 45/06 | (2006.01) |

(52) U.S. Cl.
CPC .......... C07C 309/15 (2013.01); A61K 31/185 (2013.01); A61K 31/423 (2013.01); A61K 45/06 (2013.01); C07D 263/57 (2013.01); C07B 2200/07 (2013.01); C07C 2601/14 (2017.05); C07C 2601/16 (2017.05)

(58) Field of Classification Search
CPC ............................ C07C 309/15; A61K 31/185
USPC ....................................................... 548/224
See application file for complete search history.

(56) References Cited

U.S. PATENT DOCUMENTS

| | | | |
|---|---|---|---|
| 3,524,846 | A | 8/1970 | Moffatt et al. |
| 3,536,809 | A | 10/1970 | Applezweig |
| 3,598,123 | A | 8/1971 | Zaffaroni |
| 3,845,770 | A | 11/1974 | Theeuwes et al. |
| 3,916,899 | A | 11/1975 | Theeuwes et al. |
| 4,008,719 | A | 2/1977 | Theeuwes et al. |
| 5,059,595 | A | 10/1991 | Le Grazie |
| 5,073,543 | A | 12/1991 | Marshall et al. |
| 5,120,548 | A | 6/1992 | McClelland et al. |

(Continued)

FOREIGN PATENT DOCUMENTS

| | | |
|---|---|---|
| CA | 2678265 | 10/2015 |
| CA | 2770298 | 6/2017 |

(Continued)

OTHER PUBLICATIONS

Alexander, P., et al., "Preparation of 9-(2-Phosphonomethoxyethyl) Adenine Esters as Potential Prodrugs," Col/ect. Czech. Chem. Commun. (in prior U.S. Appl. No. 12/526,45859),1853-1869, Nakladatelstvi Ceskoslovenski Akademie Ved. (1994).

(Continued)

*Primary Examiner* — Melenie L Gordon
*Assistant Examiner* — Taina D Matos Negron

(57) ABSTRACT

Provided herein are compounds, including enantiomerically pure forms thereof, and pharmaceutically acceptable salts or co-crystals and prodrugs thereof which have glucagon receptor antagonist or inverse agonist activity. Further, provided herein are pharmaceutical compositions comprising the same as well as methods of treating, preventing, delaying the time to onset or reducing the risk for the development or progression of a disease or condition for which one or more glucagon receptor antagonist is indicated, including Type I and II diabetes, insulin resistance and hyperglycemia. Moreover, provided herein are methods of making or manufacturing compounds disclosed herein, including enantiomerically pure forms thereof, and pharmaceutically acceptable salts or Co-crystals and prodrugs thereof.

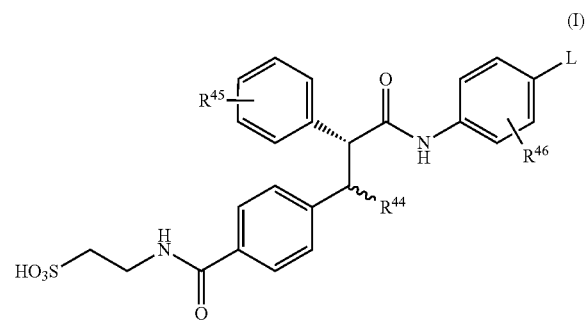

14 Claims, No Drawings

(56) References Cited

U.S. PATENT DOCUMENTS

| | | |
|---|---|---|
| 5,157,027 A | 10/1992 | Biller et al. |
| 5,354,556 A | 10/1994 | Sparks et al. |
| 5,591,767 A | 1/1997 | Mohr et al. |
| 5,639,476 A | 6/1997 | Oshlack et al. |
| 5,674,533 A | 10/1997 | Santus et al. |
| 5,733,566 A | 3/1998 | Lewis |
| 6,132,420 A | 10/2000 | Dionne et al. |
| 6,245,357 B1 | 6/2001 | Edgren et al. |
| 6,270,787 B1 | 8/2001 | Ayer |
| 6,283,953 B1 | 9/2001 | Ayer et al. |
| 6,287,295 B1 | 9/2001 | Chen et al. |
| 6,333,050 B2 | 12/2001 | Wong et al. |
| 6,342,249 B1 | 1/2002 | Wong et al. |
| 6,365,185 B1 | 4/2002 | Ritschel et al. |
| 6,368,626 B1 | 4/2002 | Bhatt et al. |
| 6,375,975 B1 | 4/2002 | Modi |
| 6,375,978 B1 | 4/2002 | Kleiner et al. |
| 6,503,949 B1 | 1/2003 | Lau et al. |
| 6,875,760 B2 | 4/2005 | Lau et al. |
| 6,881,746 B2 | 4/2005 | Lau et al. |
| 7,301,036 B2 | 11/2007 | Parmee et al. |
| 8,519,145 B2 | 8/2013 | Kang et al. |
| 8,710,236 B2 | 4/2014 | Gomez-Galeno et al. |
| 8,907,103 B2 | 12/2014 | Gomez-Galeno et al. |
| 9,169,201 B2 | 10/2015 | Gomez-Galeno et al. |
| 9,701,626 B2 | 7/2017 | Gomez-Galeno et al. |
| 2003/0212119 A1 | 11/2003 | Lau et al. |
| 2003/0236292 A1 | 12/2003 | Kodra et al. |
| 2004/0014789 A1 | 1/2004 | Lau et al. |
| 2004/0152750 A1 | 8/2004 | Kodra et al. |
| 2005/0288329 A1 | 12/2005 | Yao et al. |
| 2006/0084681 A1 | 4/2006 | Parmee et al. |
| 2006/0116366 A1 | 6/2006 | Parmee et al. |
| 2007/0015757 A1 | 1/2007 | Madsen et al. |
| 2007/0054902 A1 | 3/2007 | Fukui et al. |
| 2007/0088071 A1 | 4/2007 | Kim et al. |
| 2007/0105930 A1 | 5/2007 | Parmee et al. |
| 2007/0203186 A1 | 8/2007 | Beeson et al. |
| 2007/0249688 A1 | 10/2007 | Conner et al. |
| 2008/0085926 A1 | 4/2008 | Stelmach et al. |
| 2008/0108620 A1 | 5/2008 | Brockunier et al. |
| 2008/0125468 A1 | 5/2008 | Chappell et al. |
| 2015/0087680 A1 | 3/2015 | Gomez-Galeno |
| 2017/0216229 A1 | 8/2017 | Zhi |
| 2017/0275246 A1 | 9/2017 | Gomez-Galeno et al. |

FOREIGN PATENT DOCUMENTS

| | | |
|---|---|---|
| CN | 1774433 A | 5/2006 |
| CN | 1784226 A | 6/2006 |
| CN | 102292316 | 7/2015 |
| CN | 104803891 A | 7/2015 |
| CN | 106687118 A | 5/2017 |
| CN | ZL 20880004461.9 | 8/2017 |
| DK | 2799428 | 2/2017 |
| EP | 0 284 240 B2 | 6/1993 |
| EP | 0 632 048 A1 | 1/1995 |
| EP | 2 129 654 A1 | 12/2009 |
| EP | 2 326 618 A1 | 10/2014 |
| EP | 2 786 985 A1 | 10/2014 |
| EP | 2 799 428 | 11/2016 |
| EP | 3 153 501 | 4/2017 |
| EP | 3 154 956 | 4/2017 |
| HK | 1203481 A | 10/2015 |
| IN | 273645 | 6/2016 |
| JP | 63-32538 | 2/1988 |
| JP | 63-231452 A2 | 9/1988 |
| JP | 09-241284 A | 9/1997 |
| JP | 11-97740 A | 4/1999 |
| JP | 2003-524651 | 8/2003 |
| JP | 2004-501897 | 1/2004 |
| JP | 2005-511683 | 4/2005 |
| JP | 2006-500325 | 1/2006 |
| JP | 2006-510650 | 3/2006 |
| JP | 2010-511604 | 4/2010 |
| JP | 2010-518124 A | 5/2010 |
| JP | 2013-177426 | 9/2013 |
| JP | 5322951 | 10/2013 |
| JP | 5684126 | 1/2015 |
| JP | 2015-129133 | 7/2015 |
| JP | 2016-041702 | 3/2016 |
| JP | 2017-101039 | 6/2017 |
| JP | 2017-51900 | 7/2017 |
| KR | 10-2008-0050348 | 12/2006 |
| KR | 10-2015-0008922 | 1/2015 |
| KR | 10-1538810 | 7/2015 |
| KR | 10-1599089 | 2/2016 |
| KR | 10-2017-0085615 | 7/2017 |
| MX | 318858 | 3/2014 |
| WO | WO 90/08155 A1 | 7/1990 |
| WO | WO 90/10636 A1 | 9/1990 |
| WO | WO 91/19721 A1 | 12/1991 |
| WO | WO 00/069810 A1 | 11/2000 |
| WO | WO 00/071510 A2 | 11/2000 |
| WO | WO 01/019830 A1 | 3/2001 |
| WO | WO 01/062717 A1 | 8/2001 |
| WO | WO 02/00612 A1 | 1/2002 |
| WO | WO 02/040444 A1 | 5/2002 |
| WO | WO 03/048109 A1 | 6/2003 |
| WO | WO 03/053938 A1 | 7/2003 |
| WO | WO 04/002480 A1 | 1/2004 |
| WO | WO 04/050039 A2 | 6/2004 |
| WO | WO 04/052869 A1 | 6/2004 |
| WO | WO 04/069158 A2 | 8/2004 |
| WO | WO 04/092156 A1 | 10/2004 |
| WO | WO 04/100875 A2 | 11/2004 |
| WO | WO 05/051298 A1 | 6/2005 |
| WO | WO 05/054213 A1 | 6/2005 |
| WO | WO 05/065680 A1 | 7/2005 |
| WO | WO 05/118542 A1 | 12/2005 |
| WO | WO 05/121097 A2 | 12/2005 |
| WO | WO 05/123668 A1 | 12/2005 |
| WO | WO 06/086488 A2 | 8/2006 |
| WO | WO 06/102067 A1 | 9/2006 |
| WO | WO 06/104826 A2 | 10/2006 |
| WO | WO 07/015999 A2 | 2/2007 |
| WO | WO 07/047177 A1 | 4/2007 |
| WO | WO 07/106181 A2 | 9/2007 |
| WO | WO 07/111864 A2 | 10/2007 |
| WO | WO 07/114855 A2 | 10/2007 |
| WO | WO 07/120270 A2 | 10/2007 |
| WO | WO 07/120284 A2 | 10/2007 |
| WO | WO 07/123581 A1 | 11/2007 |
| WO | WO 07/136577 A2 | 11/2007 |
| WO | WO 08/001883 A1 | 1/2008 |
| WO | WO 08/042223 A1 | 4/2008 |
| WO | WO 08/066356 A1 | 6/2008 |
| WO | WO 08/098244 A1 | 8/2008 |
| WO | WO2008098244 A1 * | 8/2008 |
| WO | WO 10/019830 A1 | 2/2010 |
| WO | WO 2013/012959 A1 | 1/2013 |
| WO | WO 2015/191900 A1 | 12/2015 |
| WO | WO 2017/084226 | 5/2017 |

OTHER PUBLICATIONS

Alza Corporation, "L-Oros™ Technology—Advancing New Therapies Through ALZA's Liquid Drug Formation," Delivery Times, vol. II, Issue II, 2002, 12 pages.

American Heart Association, "Metabolic Syndrome" <http://www.americanheart.org/presenter.jhtml?identifier=4756>, Accessed Mar. 31, 2009.

Ash and Ash, Eds., Handbook of Pharmaceutical Additives, 3rd ed, Gower Publishing Company, 2007, 3 pages.

Baddiley et al., "Structure of Coenzyme A," Nature 171:76 (1953).

Benzaria et al., "Synthesis, in Vitro Antiviral Evaluation, and Stability Studies of Bis(S-acyl-2-thioethyl) Ester Derivatives of 9-[2-(Phosphonomethoxy)ethyl] adenine (PMEA) as Potential PMEA Prodrugs with Improved Oral Bioavailability," J. Med. Chem. 39(25):4958-4965 (1996).

Bhongle et al., "Expedient and High-Yield Synthesis of Alkylphosphonyl Cichlorides Under Mile, Neutral Conditions: Reaction of BIS

(56) References Cited

OTHER PUBLICATIONS (Trimethylsilyl) Slkyl Phosphonates with Oxalyl Chloridel Dimethylformarnide," Synth. Commu. 17:1071-1706 (1987).
Blackburn et al., "Specific Dealkylation of Phosphonate Esters using Iodotrimcthylsilanc," J. Chem. Soc., Chem. Commun. 870-871 (1978).
Brand et al., "Evidence for a Major Role of Glucagon in the Hyperglycemia of Experimental Diabetes," A Journal of the American Diabetes Association, 1994, 43 (Suppl. 1), 172A.
Brand et al., "Immunoneutralization of endogenous glucagon with monoclonal glucagon antibody normalizes hyperglycaemia in moderately streptozotocin-diabetic rats," Diabetologia 1994, vol. 37, pp. 985-993.
Brechbühler et al., "Die Reaktion von Carbonsauren mit Acetalen des N, N-Dimethylformmids: eine Veresterungsmethode," Helv. Chim. Acta. 48(7):1746-1771 (1965).
Bundgaaard, ed., Design of Prodrugs, Elsevier Science, Amsterdam, 1985.
Busch-Peterson et al., "Lithium N-trityl-N-(R)-I-phenethylamide, a readily available and useful base for the enantioselective formation of chiral cnolates from achiral ketones," Tetrahedron Letters 41(36):6941-6944 (2000).
Campagne, J.-M. et al., "Synthesis of Mixed Phosphonate Diester Analogues of Dipeptides using BOP or PyBOP Reagents," Tetrahedron Left. 34(42), 6743-6744, Pergamon Press Ltd. (1993).
Campbell, DA, "The Synthesis of Phosphonate Esters, an Extension of the Mitsunobu Reaction," J. Org. Chem. 57,6331-6335, American Chemical Society (1992).
CAS Registry No. 852460-16-3, STN Entry Date Jun. 17, 2005.
CAS Registry No. 131055-48-6, STN Entry Date Dec. 14. 1990.
CAS Registry No. 127192-35-2, STN Entry Date May 18, 1990.
CAS Registry No. 141740-28-5, STN Entry Date Jun. 12, 1992.
CAS Registry No. 141220-32-8, STN Entry Date May 8, 1992.
CAS Registry No. 127192-36-3, STN Entry Date May 18, 1992.
CAS Registry 699001-74-6, STN Entry Date Jun. 25, 2004.
Casara, P.J. et al., Synthesis of Acid Stable 5'-O-Fluoromethyl Phosphonates of Nucleosides. Evaluation as Inhibitors of Reverse Transcriptase,• Bioorg. Med. Chem. Left. 2(2), 145-148, Pergamon Press pic. (1992).
Cereda et al., "Solid-phase synthesis of 3-hydroxymethyl isoxazoles via resin bound nitrile oxides," Tetrahedron Lett. 42(30):4951-4953(2001).
Coppi et al., "Lewis Acid Mediated Condensation of Alkenols and Aldehydes. A Selective Synthesis of Tetrahydropyrans and Oxepanes," J. Org. Chern. 53(4) 911-913 (1988).
Curran et al., "Thermolysis ofbis[2-[(trimethylsilyl)oxy]prop-2-yl] furoxan (TOP-furoxan), The First Practical Method for Intermolecular Cycloaddition of an in Situ Generated Nitrile Oxide with 1, 2-Di—and Trisubstituted Olefins," J. Am. Chem. Soc. 107(21):6023-6028 (1985).
DeLambert et al., "N-Phosphonomethyl Dipeptides and Their Phosphonate Prodrugs, a New Generation of Neutral Endopeptidase (NEP, TIC3.4.24.11) Inhibitors," J. Med. Chem. 37(7):498-511 (1994).
Egron et al., "Synthesis and Anti-HIV Activity of Some S-Acyl-2-thioethyl (SATE) Phosphoramidate Derivatives of3' -Acido-2' 3' -dideoxythymidine," Nucleosides & Nucleotides 18(4):981-982 (1999).
Elhaddadi et al., "A Convenient Synthesis of Alkyl and Dialkyl 1-benzyloxyamino alkyl phosphonates and phosphinates," Phosphorus, Sulfur and Silicon 54:143-150 (1990).
Elliott, RL. et al., "Synthesis and Biological Evaluation of Phosphonamidate Peptide Inhibitors of Enkephalinase and Angiotensin-Converting Enzyme," J. Med. Chem. 28: 1208-1216, American Chemical Society (1985).
Farquhar et al., "Biologically Reversible Phosphate-Protective Groups," J. Pharm. Sci. 72(3):324-325 (1983).
Faulon, J-L., et al.: "The Signature Molecular Descriptor. 2. Enumerating Molecules from Their Extended Valence Sequences," Journal of Chemical Information and Computer Sciences, 2003, vol. 43, No. 3, pp. 721-734.

Federal Register 2011, 76 (27), p. 7166.
Ferres, "Pro-Drugs of B-Lactam Antibiotics," Drugs of Today 19(9):499-538 (1983).
Franchetti, P. et al.: Potent and selective inhibitors of human Immunodeficiency virus protease structurally related toL-694,746, Antiviral Chemistry and Chemotherapy, 1998, vol. 9, No. 4, pp. 303-309.
Freed et al., "Evidence for Acyloxmethyl Esters of Pyrimidine 5'-Deoxyribonucleotides as Extracellular Sources of Active 5'-Deoxyribonucleotides in Cultured Cells," Biochem. Pharmac. 38:3193-3198 (1989).
Garbisch et al, "Conformations. IV. The Conformational Preference of the Phenyl Group in Cyclohexane," J. Am. Chem. Soc., 1963, vol. 85, pp. 3228-3231.
Gibson, Ed., Pharmaceutical Preformulation and Formulation, CRC Press LLC, Boca Raton, FL, 2004.
Greene et al., Protective Groups in Organic Synthesis, John Wiley, New York, 1990.
Grundy et al., "Diagnosis and Management of the Metabolic Syndrome," Circulation, 112 (2005), p. 2735-2752.
Gupta et al., "An Improved Synthesis of Vinylic Phosphonates from Ketones," Synth. Commun. 10(4):299-304 (1980).
Hoffman, "A Simple Efficient Synthesis of Dibenzyl and Di-p-nitrobenzyl 1-Hydroxyalkanephosphonates," Synthesis 1988(1):62-64 (1988).
Huang et al., "a-Hypervalent Iodine Functionalized Phosphonium and Arsonium Ylides and Their Tandem Reaction as Umpolung Reagents," J Org. Chem. 67(23):8261-8264 (2002).
Inanaga et al., "A Rapid Esterification by Means of Mixed Anydride and Its Application to Large-ring Lactonization," Bulletin of the Chemical Society of Japan 52(7):1989-1993 (1979).
Johnson et al., "The Regulation of Gluconeogenesis in Isolated Rat Liver Cells by Glucagon, Insulan, Dibutyrl Cyclic Adenosine Monophosphate, and Fatty Acids," J. Biol. Chem., 1972, vol. 247, No. 10, pp. 3229-3235.
Juliano, Ed., Drug Delivery Systems, Oxford Univ. Press, Oxford, 1980.
Kerns et al., "Selective N-Sulfation of Glucosamine Derivatives Using Phenyl Chlorosulfate in Non-Qqueous Solvent," Synthetic Communications., 26:2671-2680, 1996.
Khamnei, S. et al., "Neighboring Group Catalysis in the Design of Nucleotide Prodrugs," J. Med. Chem. 39, 4109-4115, American Chemical Society (1996).
Kim, Cherug-ju, Controlled Release Dosage Form Design, 231-238, Technomic Publishing, Lancaster PA 2000.
Kozma, CRC Handbook of Optical resolutions via Diastereomeric Salt Formation, CRC Press, 2001.
Kurti et al., Strategic Applications of Named Reactions in Organic Synthesis, Elsvier, 340-342, 2005.
Kurukulasuriya et al., "Biaryl amide glucagon receptor antagonists," Bioorg. Med. Chem. Lett. 14(9):2047-2050 (2004).
Larock, Comprehensive Organic transformations, VCH, New York, 1989.
Latour et al., "Simple Syntheses of 2-Hydroxymethy-1, 3-propanediol and Related Compounds," Synthesis 1987(8):742-745 (1987).
Lee et al., "Synthesis and In Vitro Activity of Novel Isoxazolyl Tetrahydropyridinyl Oxazolidinone Antibacterial Agents," Bioorg. Med. Chern. Lett. 13(22):4117-4120 (2003).
Lejczak et al., Transcstcrification ofDiphenyl Phosphonates Using the Potassium Fluoride/Crown Ether/Alcohol System; Part 2. The Use of Diphenyl 1-Aminoalkanephosphonates in Phosphonopeptide Synthesis 1982(5):412-414 (1982).
Li et al.: "Chiral Drug Separation," Encyclopedia of Chemical Processing (2006), pp. 449-458.
Lyapkalo et al., (Enantioselective Synthesis of Cyclohexenylalkenes by Asymmetric Depprotonation of 4-tert-Butylcyclohexanone Followed by O-Nonatlation and Heck Couplings, SynZett 1292-1295 (2001).
Martin et al., "Synthesis and Antiviral Activity of Various Esters of 9-[(1 ,3-Dihydroxy-2-propoxy)methyl]guanine," J. Pharm. Sci. 76(2):180-184 (1987).

(56) References Cited

OTHER PUBLICATIONS

Mathur,"Metabolic Syndrome" see section "How is metabolic syndrome defined?" <http://www.medicinenet.com/metabolic syndrome/article.htm>, pp. 2-3, Accessed Mar. 31, 2009.

McGuigan, C. et al., "Kinase Bypass: A New Strategy for Anti-HIV Drug Design," Bioorganic & Medicinal Chemistry Letters 3(6): 1207-1210, Pergamon Press Ltd. (1993).

McKenna et al., "The facile dealkylation of phosphonic acid dialkyl esters by bromotrimethylsilanc," Tetrahedron Lett. 2:155-158 (1977).

Meier, C. et al., "Cyclic Saligenyl Phosphotriesters of 2',3'-Dideoxy-2',3'-didehydrothymidine (d4T)—A New Pro-Nucleotide Approach," Bioorganic Med. Chem. Lett. 7(2), 99-104, Elsevier Science Ltd. (1997).

Mitchell, A.G. et al., "Bioreversible Protection for the Phospho Group: Bioactivation of the Di(4-acyloxybenzyl) and Mono(4-acyloxybenzyl) Phosphoesters of Methylphosphonate and Phosphonacetate," J. Chem. Soc. Perkin Trans. 1 38:2345-2353, Chemical Society, London (1992).

Mitsunobu, 0., "The Use of Diethyl Azodicarboxylate and Triphenylphosphine in Synthesis and Transformation of Natural Products," Synthesis 1-28, Georg Thieme Verlag (1981).

Moriarty et al., "Diphenyl Methylphosphonate as a Phosphonylation Reagent with High Diastereoselectivity at Phosphorus," Tetrahedron Lett. 38(15):2597-2600 (1997).

Mukalyama et al., "Synthesis of Oligothymidylates and Nucleoside Cyclic Phosphates by Oxidation-Reduction Condensation," J. Am. Chem. Soc. 94(24):8528-8532 (1972).

Nishimura et al., "Orally Active 1-(Cyclohexyloxycarbonyloxy)alkyl Ester Prodrugs of Cefotiam," J. Antibiotics 40(1):81-90 (1987).

Ogg, M.S. et al., "A Reporter Gene Assay to Assess the Molecular Mechanisms of Xenobiotic-dependent Induction of the Human CYP3A4 Gene in Vitro," Xenobiotica 29(3), 269-279, Taylor & Francis Ltd. (Mar. 1999).

Ohashi, K. et al., "Synthesis of Phosphonosphingoglycolipid Found in Marine Snail Turbo Cornutus," Tetrahedron Lett. 29(10), 1189-1192, Pergamon Press pic. (1988).

Patois et al., "Easy preparation of alkylphosphonyl dichlorides," Bull. Soc. Chim Fr. 130:485-487 (1993).

Pelchowicz, "Organic Phosphorus Compounds. Part 1.The Reaction of Dialkyl Mthylphosphnates and Methylphosphonothionates with Inorganic Acid Chlorides," J Chern. Soc. 238-240 (1961).

Petasis et al., "The boronic acid mannich reaction: A new method for the synthesis of geometrically pure allylarnines," Tetrahedron Lett. 34(4):583-586 (1993).

Posner et al., "3-bromo-2-pyrone: an easily prepared chameleon diene and a synthetic equivalent of 2-pyrone in thermal diels-alder cycloadditions," Tetrahedron Letters 32(39):5295-5298 (1991).

PubMed Health,"Type 1 diabetes" Jun. 28, 2011.

Puech et al., "Intracellular delivery ofnucleoside monophosphates through a reductase-mediated activation process," Antiviral Res. 22(2-3):155-174 (1993).

Quast et al., "Herstellung von Methylphosphonsaure-dichlorid," Synthesis 1974(7):490 (1974).

Rabinowitz, "The Reactions of Phosphonic Acid Esters with Acid Chlorides. A Very Mild Iiydrolytic Route," J. Org. Chem. 28(11):2975-2978 (1963).

Ramachandran et al., "Efficient General Synthesis of 1,2—and 1,3-diols in High Enantiomeric Excess via the Intramolecular Asymmetric Reduction of the Corresponding Ketoalkyl Diisopinocampheylborinate Intermediates," Tetrahedron, 38(5):761-764 (1997).

Rao et al., "Studies directed towards the synthesis of immunosuppressive agent FK-506: synthesis of the entire top-half," Tetrahedron Letters 32(4):547-550 (1991).

Rathbone et al, Eds., Modified-Release Drug Deliver Technology, Drugs and the Pharmaceutical Science, Marcel Dekker, Inc.: New York, NY, vol. 126, 2003.

Remington: The Science and Practice of Pharmacy, 21st Ed., Lippincott Williams & Wilkins, Philadephia, PA, 2005.

Remington's Pharmaceutical Sciences, 18th ed., Mack Publishing, Easton PA, 173, 1990, and pp. 172-174.

Roche, Ed., Design of Biopharmaceutical Properties through Prodrugs and Analogs, American Pharmaceutical Association, Washington, 1977.

Roden et al., "The Roles of Insulin and Glucagon in the Regulation of Hepatic Glycogen Synthesis and Turnover in Humans," J. Clin. Invest. 1996, vol. 97, No. 3, pp. 642-648.

Rosowsky et al., "Methotrexate Analogues. 32. Chain Extension, a-Carboxyl Delection, and y-Carboxyl Replacement by Sulfonate and Phosphonate: Effect on Enzyme Binding and Cell-Growth Inhibition," J. Med. Chem. 31: 1326-1331 (1988).

Rowe et al., Eds., Handbook of Pharmaceutical Excipients, 5th Ed., The Pharmaceutical Press and the Merican Pharmaceutical Association, 2006.

Sakamoto et al., "The palladium-catalyzed arylation of 4H-1,3-dioxin," Tetrahedron Lett. 33(45):6845-6848 (1992).

Schoeller, et al., "Measurement of energy expenditure in humans by doubly labeled water method," J. Appl Physiol., 53(4), pp. 955-959, (1982).

Serafinowska et al., "Synthesis and in Vivo Evaluation of Prodrugs of 9-[2-(Phosphonomethoxy)ethoxy] adenine," J. Med. Chem. 38(8):1372-1379 (1995).

Shafer et al., "On the Mechanism of Reductive Cleavage of Aryl Phosphates," J. Am. Chem. Soc. 99(15):5118-5123 (1977).

Shaw-Ponter et al., "New synthesis of both D—and L-3-O-Carbamoyl-2-deoxy-4-thioribosides, Substrates for I)-selective Glycosylations," Tetrahedron Letters 37:1871-1874 (1981).

Shono et al., "Electroreductive Elimination of Phenolic Hydroxyl Groups and a New Synthesis of OlivetoI," J. Org. Chem. 44(25):4508-4511.

Siddiqui et al., "The Presence of Substitucnts on the Aryl Moeity of the Aryl Phosphoramidate Derivative of d4T Enhances Anti-HIV Efficacy in Cell Culture: A Structure-Activity Relationship," J. Med. Chem. 42:393-399 (1999).

Silverman, Chapter 8: "Prodrugs and Drug Delivery Systems", The Organic Chemistry of Drug Design and Drug Action, Academic Press, 1992, pp. 352-401.

Singh et al., "Design and Synthesis of Isoxazole Containing Bioisosteres of Epihatidine as Potent Nicotinic Acetylcholine Receptor Agonists," Chem. Pharm. Bull. 47(10):1501-1505 (1999).

Slavica et al., "Systhesis and Biological Activities of a New Set of Irreversibly Acting 2-(4'-Isothiocyanatobenzyl)imidazoline Analogs in Rat Thoracic Aorta," J. Med. Chem. 1994, vol. 37, No. 12, pp. 1874-1881.

Starrett, Jr. et al., "Synthesis, Oral Bioavailability Determination, and in Vitro Evaluation of Prodrugs of the Antiviral Agent 9-[2-(Phosphonomethoxy)ethyl]adenine (PMEA)," J. Med, Chem 37:1857-1864 (1994).

Still et al., "Direct synthesis of Z-unsaturated esters. A useful modification of the hormer-emmons olefination," Tetrahedron Letters 24(41):4405-4408 (1983).

Stowell et al., "The Mild Preparation of Synthetically Useful Phosphonic Dichlorides: Applicationt to the Synthesis of Cyclic Phosphonic Diesters and Diamides," Tetrahedron Letters 31(23):3261-3262 (1990).

Tawfik et al., "1,8-Diazabicyclo[5.4.0]undecene Mediated Transesterification ofp-Nitrophenyl Phosphonates: A Novel Route to Phosphono Esters," Synthesis 1993(10):968-972 (1993).

Toke et al., "A Versatile Building Block for the Synthesis of Substituted Cyclopropanephosphonic Acid Esters," Tetrahedron Letters 51(33):9167-9178 (1995).

Turner, JA, "A General Approach to the Synthesis of 1,6-,1,7-, and 1,8- Naphthyridines," J. Org. Chem. 55(15),4744-4750, American Chemical Society (1990).

United States Pharmacopeia, The, 23rd ed., pp. 1843-1844, 1995.

Valette et al., "Decomposition Pathways and in Vitro HIV Inhibitory Effects of IsoddA Pronucleotides: Toward a Rational Approach for Intracellular Delivery of Nucleotide 5'-Monophosphates," J. Med. Chem. 39(10):1981-1990 (1996).

(56) References Cited

OTHER PUBLICATIONS

Vanderwal et al., "An Enantioselective Synthesis of FR182877 Provides a Chemical Rationalization of Its Structure and Affords Multigram Quantities of Its Direct Precursor," J. Am. Chem. Soc. 125(18):5393-5407.
Xu et al., "A General Route to the Synthesis of N-Protected 1-Substituted and 1,2-Disubstituted Taurines," Synthesis 2004(2):276-282 (2004).
Yamamoto et. al., "Synthesis of Pyridine N-Oxide-SbCIs Complexes and Their Intramolecular and Oxygen-Transfer Reaction," Tetrahedron 37:1871-1873 (1981).
Yan et al., "Preparation, Properties, Reactions, and Adenosine Receptor Affinities of Sulfophenylxanthine Nitrophenyl Esters: Toward the Development of Sulfonic Acid Prodrugs with Peroral Bioavailability," J. Med. Chem. 47(4):1031-1043 (2004).
Yao et al., "Generation of Nitroalkanes, Hydroximoyl Halides and Nitrile Oxides from the Reactions of B-Nitrostyrenes with Grignard or Organolithium Reagents," Tetrahedron Letters 54(5/6):791-822 (1998).
Younker et al., "A mechanistic Study of the Alkaline Hydrolysis of Diaryl Sulfate Diesters," J. Org. Chem. 69(26):9043-9048(2004).
Ballatore: "Carboxylic Acid (Bio)Isosteres in Drug Design," ChemMedChem 8.3 (2013): 385-395.
R. Jason Herr: "5-Substituted—1H-tetrazoles as Carboxylic Acid Isosteres: Medicinal Chemistry and Synthetic Methods," Bioorg. Med. Chem. 10 (2002) 3379-3393.
Macchiarulo, et al.: "Exploring the other side of bilogically relevant chemical space: Insights into carboxylic, sulfonic and phosphonic acid bioisosteric relationships Roberto Pellicciari," Journal of Molecular Graphics and Modelling 26 (2007) 728-739.
Lidia Moerira Lima, et al.: "Bioisosterism: A Useful Strategy for Molecular Modificaion and Drug Design, Current Medicinal Chemistry," 2005, 12, 23-49.
Australian Office Action in AU Application No. 2008212816, dated Nov. 9, 2012.
Australian Office Action in AU Application No. 2008212816, dated Dec. 20, 2012.
Australian Office Action in AU Application No. 2014204420, dated Aug. 22, 2016.
Office Action in U.S. Appl. No. 13/083,321, dated Jul. 12, 2013.
Office Action in U.S. Appl. No. 14/860,593, dated Jan. 5, 2016.
Canadian Office Action in CA Application No. 2,678,265, dated Feb. 4, 2014.
Canadian Office Action in CA Application No. 2,678,265, dated Jul. 11, 2014.
Canadian Office Action in CA Application No. 2,894,112, dated Jul. 4, 2016.
First Office Action in Chinese Application No. 200880004461.9 dated Jun. 15, 2012.
Second Office Action in Chinese Application No. 200880004461.9 dated Apr. 28, 2013.
Third Office Action in Chinese Application No. 200880004461.9 dated Jan. 17, 2014.
Decision on Rejction in Chinese Application No. 200880004461.9 dated Jun. 27, 2014.
Supplementary Partial European Search Report dated Jul. 17, 2012, European Patent Application No. EP 08 72 9528, 7 pages.
Examination Report, re EP Application No. EP 08 729 528.3, dated Feb. 20, 2013.
Extended Search Report, re EP Application No. 14162609.3, dated Jan. 8, 2015.
Indian Office Action, re IN Application No. 5771/DELNP/2009, dated Sep. 13, 2009.
Japanese Office Action, re JP Application No. JP 2009-549286, dated Feb. 26, 2013.
Japanese Office Action, re JP Application No. JP 2013-110101, dated Jun. 3, 2014.
Japanese Office Action, re JP Application No. JP 2013-110101, dated Jun. 2, 2015.
Japanese Pre-appeal Exam Report, re JP Application No. JP 2013-110101, dated Oct. 29, 2015.
Japanese Office Action, re JP Application No. JP 2015-196171, dated Nov. 8, 2016.
Korean Office Action (Reasons for Rejection), re KR Application No. 10-2012-7025865.
Korean Office Action, re KR Application No. 10-2014-7036395, dated Mar. 23, 2015.
Korean Office Action, re KR Application No. 10-2014-7036395, dated Jan. 4, 2016.
Korean Notice on the Result of Reexamination, re KR Applicaton No. 10-2014-7036395, dated (appx.) Jun. 16, 2016.
Korean Office Action (wTranslation), re KR Application No. 10-2016-7011147, dated Jul. 19, 2016.
Office Action in Mexico Application No. MX/a/2009/008534 dated Jun. 27, 2013.
Office in Mexico Application No. MX/a/2014/003565, dated May 16, 2016 (w/translation).
Office in Mexico Application No. MX/a/2014/003565, dated Oct. 26, 2016 (w/translation).
International Search Report dated Jul. 17, 2008, in International Application No. PCT/US2008/053581.
International Preliminary Report on Patentability dated Aug. 11, 2009, in International Application No. PCT/US2008/053581.
Canadian Office Action, re CA Application No. 2,770,298, dated Jun. 8, 2015.
Canadian Office Action, re CA Application No. 2,770,298, dated Feb. 17, 2016.
Chinese Office Action in CN Application No. 200980141324.4, dated Apr. 15, 2013.
Chinese Search Report in CN Application No. 200980141324.4, dated Apr. 3, 2013.
Chinese Office Action in CN Application No. 200980141324.4, dated Jan. 6, 2014.
Chinese Third Office Action in CN Application No. 200980141324.4, dated Aug. 5, 2014.
Chinese First Office Action in CN Application No. 201510257808.2, dated Feb. 16, 2016.
Chinese Second Office Action in CN Application No. 201510257808.2, dated Oct. 26, 2016.
European Exam Report, re EP Application No. 09 791 510.2, dated Feb. 7, 2013.
European Exam Report, re EP Application No. 09 791 510.2, dated Apr. 2, 2014.
European Extended Search Report, re EP Application No. 14179199.6, dated Nov. 17, 2104.
Japanese Office Action, re JP Application No. JP 2011-523184, dated Jan. 14, 2014.
Japanese Office Action, re JP Application No. JP 2015-005005, dated Dec. 1, 2015.
Japanese Office Action, re JP Application No. JP 2015-005005, dated Sep. 6, 2016.
Korean Office Action, re KR Application No. 10-2014-7036395 (Original KR App. No. 10-2009-7016602), dated Mar. 20, 2015.
Korean Notice of Preliminary Rejection, re KR Application No. 10-2014-7036395 (Original KR App. No. 10-2009-7016602), dated Aug. 11, 2015.
Korean Notice of Preliminary Rejection, re KR Application No. 10-2015-7027964 (Original KR App. No. 10-2011-7005737), dated Dec. 1, 2015.
Korean Notice of Allowance, re KR Application No. 10-2015-7027964 (Original KR App. No. 10-2011-7005737), dated Mar. 24, 2016.
Mexican Office Action, re MX Application No. MX/a/2011/001708, dated Jul. 23, 2013.
International Search Report in Application No. PCT/US2009/053795 (now International Publication No. WO 2010/019830 A1), dated Dec. 18, 2009 (2 pages).
International Search Report and Written Opinion in Application No. PCT/US15/35400, dated Sep. 3, 2015. (23 pages).
International Preliminary Report on Patentability in Application No. PCT/US15/35400, dated Dec. 15, 2016. (14 pages).

(56) References Cited

OTHER PUBLICATIONS

Australian Office Action in AU Application No. 2014204420, dated Mar. 17, 2017.
Australian Office Action in AU Application No. 2014204420, dated Aug. 10, 2017.
Canadian Office Action in CA Application No. 2,894,112, dated Apr. 26, 2017.
Fourth Office Action in Chinese Application No. 200880004461.9 dated Jan. 13, 2017.
Chinese Notice of Allowance, re CN Application No. 200880004461.9, dated May 23, 2017.
Chinese First Office Action in CN Application No. 20151088427.4, dated May 2, 2017.
Exam Report, re EP Application No. 14162609.3, dated Feb. 2, 2017.
Korean Decision of Trial, re KR Application No. 10-2014-7036395, dated Aug. 23, 2017.
Korean Office Action, re KR Application No. 10-2016-7011147, dated May 17, 2017.
Korean Office Action, re KR Application No. 10-2017-7019679, dated Aug. 22, 2017.
Canadian Office Action, re CA Application No. 2,966,273, dated Aug. 14, 2017.
Chinese Third Office Action in CN Application No. 201510257808.2, dated Apr. 20, 2017.
Chinese Notice of Allowance in CN Application No. 201510257808.2, dated Sep. 12, 2017.
Indian Office Action, re IN Application No. 1841/DELNP/2011, dated Mar. 23, 2017.
European Extended Search Report, re EP Application No. 16198552.8, dated Mar. 1, 2017.
San Diego, "Ligand Initiates Phase 1 Trial with Glucagon Receptor Antagonist for Type 2 Diatests," Diabetes Week, Nov. 25, 2013.
Vajda et al., "Pharmacokinetics and pharmacodynamics of single and multiple doses of the glucagon receptor antagonist LGD-6972 in healthy subjects and subjects with type 2 diabetes mellitus," Diabetes, Obestity and Metabolism, vol. 19, No. 1, Aug. 31, 2016.
European Extended Search Report re EP Application No. 15805822.2, dated Dec. 20, 2016.

\* cited by examiner

GLUCAGON ANTAGONISTS

RELATED APPLICATIONS

This application is a continuation application of U.S. patent application Ser. No. 13/058,604 which was filed Oct. 6, 2011, which is a 371 of international application PCT/US2009/053795 filed Aug. 13, 2009, which claims priority to and the benefit of U.S. Provisional Application 61/088,697 filed Aug. 13, 2008, the entire contents of all of which are incorporated herein by reference.

FIELD

Provided are antagonists of glucagon receptors. In particular, provided are compounds and compositions for use in treatment, prevention or amelioration of one or more symptoms, causes, or effects of a glucoregulatory or glucagon receptor-mediated disease or disorder.

BACKGROUND

Glucagon is a 29-amino acid pancreatic hormone which is secreted from the pancreatic a cells into the portal blood supply in response to hypoglycemia. It acts as a counter-regulatory hormone to insulin. Most of the physiological effects of glucagon are mediated by its interaction with glucagon receptors in the liver, followed by activation of adenylate cyclase to increase intracellular cAMP levels. The result is an increase in glycogenolysis and gluconeogenesis, while attenuating the ability of insulin to inhibit these metabolic processes (Johnson et al., *J. Biol Chem.* 1972, 247, 3229-3235). As such, overall rates of hepatic glucose synthesis and glycogen metabolism are controlled by the systemic ratio of insulin and glucagon (Roden et al., *J. Clin. Invest.* 1996. 97, 642-648; Brand et al., *Diabetologia* 1994, 37, 985-993).

Diabetes is a disease characterized by elevated levels of plasma glucose. Uncontrolled hyperglycemia is associated with an increased risk for microvascular and macrovascular diseases, including nephropathy, retinopathy, hypertension, stroke, and heart disease. Control of glucose homeostasis is a major approach to the treatment of diabetes. It has been demonstrated in healthy animals as well as in animal models of types I and II diabetes that removal of circulating glucagon with selective and specific antibodies results in reduction of the glycemic level (Brand et al., *Diabetologia* 1994, 37, 985-993; Brand et al., *Diabetes* 1994. 43(Suppl. 1), 172A). Therefore, one of the potential treatments for diabetes and other diseases involving impaired glycemia is to block a glucagon receptor with a glucagon receptor antagonist to improve insulin responsiveness, to decrease the rate of gluconeogenesis, and/or to lower plasma glucose levels by reducing the rate of hepatic glucose output in a patient.

Glucagon antagonists are known, e.g., UA20040014789. UA20040152750A1, WO04002480A1, U.S. Ser. No. 06/881,746B2, WO03053938A1, UA20030212119. UA20030236292. WO03048109A1, WO03048109A1, WO00069810A1, WO02040444A1, U.S. Ser. No. 06/875,760B2, UA20070015757A, WO04050039A2. UA20060116366A1, WO04069158A2, WO05121097A2, WO05121097A2, WO07015999A2. UA20070203186A1, UA20080108620A1, UA20060084681A1, WO04100875A2, WO05065680A1, UA20070105930A1, U.S. Ser. No. 07/301,036B2, UA20080085926A1, WO08042223A1, WO07047177A1, UA20070088071A1, WO07111864A2, WO06102067A1, WO07136577A2, WO06104826A2, WO05118542A1, WO05123668A1, WO06086488, WO07106181A2, WO07114855A2, UA20070249688A1, WO07123581A1, WO06086488A2, WO07120270A2, WO07120284A2, and UA20080125468A1, although at this time none are commercially available as therapeutics. Not all compounds that are glucagon antagonists have characteristics affording the best potential to become useful therapeutics. Some of these characteristics include high affinity at the glucagon receptor, duration of receptor activation, oral bioavailability, and stability (e.g., ability to formulate or crystallize, shelf life). Such characteristics can lead to improved safety, tolerability, efficacy, therapeutic index, patient compliance, cost efficiency, manufacturing ease, etc. It has been unexpectedly discovered that specific stereochemistry and functional groups of the compounds of the present invention exhibit one or more of these desired characteristics, including markedly improved receptor binding properties, oral bioavailability, and/or other advantageous features that enhance their suitability for therapeutic use.

All documents referred to herein are incorporated by reference into the present application as though fully set forth herein.

BRIEF SUMMARY

Provided herein are compounds, including enantiomerically pure forms thereof, and pharmaceutically acceptable salts or co-crystals and prodrugs thereof which have glucagon receptor antagonist or inverse agonist activity. Further, provided herein are pharmaceutical compositions comprising the same, as well as methods of treating, preventing, delaying the time to onset or reducing the risk for the development or progression of a disease or condition for which one or more glucagon receptor antagonist is indicated, including without limitation Type I and II diabetes, insulin resistance and hyperglycemia. Moreover, provided herein are methods of making or manufacturing compounds disclosed herein, including enantiomerically pure forms thereof, and pharmaceutically acceptable salts or co-crystals and prodrugs thereof.

By resolution of a synthetic intermediate into pure enantiomeric forms, a more active enantiomeric series was identified and was characterized as having the R configuration. Methods for synthesis of these enantiomers are described herein. No crystal structure was obtained, however, so while the depictions herein represent the R enantiomer, the compounds of the invention are those that represent the most active enantiomer and were obtained by the synthetic methods described herein. The most active enantiomers (compounds of the invention) are those that display improved characteristics, such as surprisingly increased ratio activity vs, the S enantiomer at the cellular level as compared to activity in the receptor displacement assay.

In one aspect, a compound of Formula I is provided:

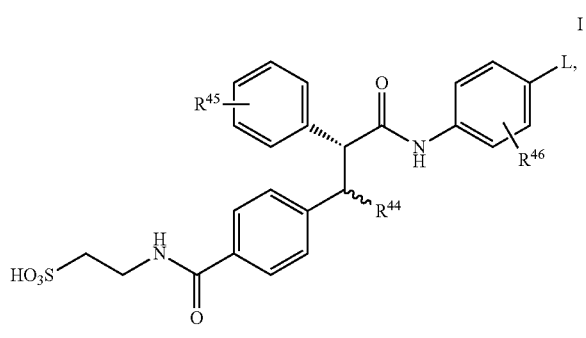

wherein:

$R^{44}$ is H, $CH_3$ or $CH_3CH_2$;

$R^{45}$ is $C_{1-6}$-alkyl, alkenyl, alkoxy, $C_{3-6}$-cycloalkyl, $C_{4-8}$-cycloalkenyl, $C_{4-8}$-bicycloalkenyl, aryl or heteroaryl, any of which can be optionally substituted with one or more substituents selected from $C_{1-6}$alkyl. $CF_3$, F, CN or $OCF_3$;

L is phenyl, indenyl, benzoxazol-2-yl, $C_{3-6}$-cycloalkyl, $C_{4-8}$-cycloalkenyl or $C_{4-8}$-bicycloalkenyl, any of which can be optionally substituted with one or more substituents selected from F, Cl, $CH_3$, $CF_3$, $OCF_3$ or CN; and $R^{46}$ represents one or more substituents selected from H, F, Cl, $CH_3$, $CF_3$, $OCF_3$ or CN;

or a pharmaceutically acceptable salt, solvate, or prodrug thereof.

In another aspect, a compound of Formula II is provided:

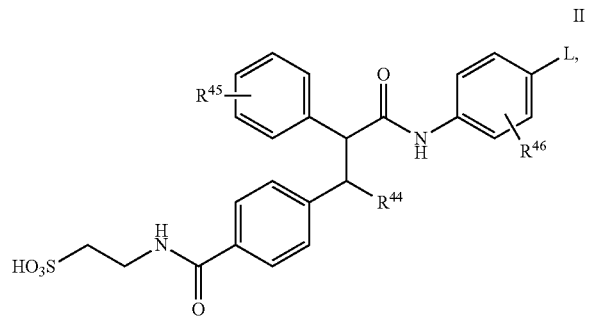

II wherein:

$R^{44}$ is H;

$R^{45}$ is cis-4-t-butylcyclohexyl, trans-4-t-butylcyclohexyl, 4,4-dimethylcyclohexyl, 4,4-diethylcyclohexyl, 4,4-dipropylcyclohexyl, 4,4-diethylcyclohex-1-enyl, 4,4-dimethylcyclohex-1-enyl, (S)-4-t-butylcyclohex-1-enyl, (R)-4-t-butylcyclohex-1-enyl, 4,4-dipropykyclohex-1-enyl, 4-t-butylphenyl, (1R,4S)-1,7,7-trimethylbicyclo[2.2.1]-3-hept-2-enyl or (1R,4R)-1,7,7-trimethylbicyclo[2.2.1]-2-hept-2-enyl:

L is phenyl, benzoxazol-2-yl, 4-alkyl-cyclohex-1-enyl, 4,4-dialkylcyclohex-1-enyl, 4-alkyl-cyclohexyl, 4,4-dialkylcyclohexyl or 4,4-dimethylcyclohexenyl, any of which can be optionally substituted with one or more substituents selected from F, Cl, $CH_3$, $CF_3$, $OCF_3$ or CN; and $R^{46}$ is H;

or a pharmaceutically acceptable salt, solvate, or prodrug thereof.

In another aspect, pharmaceutical compositions are provided comprising a compound provided herein, e.g., a compound of Formula I or Formula II, including a single enantiomer, a mixture of enantiomers, or a mixture of diastereomers thereof; or a pharmaceutically acceptable salt, solvate, or prodrug thereof; in combination with one or more pharmaceutically acceptable carriers.

Further provided herein is a method of treating, preventing, or ameliorating one or more symptoms of a condition, disorder, or disease associated with a glucagon receptor, comprising administering to a subject having or being suspected to have such a condition, disorder, or disease, a therapeutically effective amount of a compound provided herein, e.g., a compound of Formula I or II, or a pharmaceutically acceptable salt, solvate, or prodrug thereof.

Additionally, provided herein is a method of treating, preventing, or ameliorating one or more symptoms of a condition, disorder, or disease responsive to the modulation of a glucagon receptor, comprising administering to a subject having or being suspected to have such a condition, disorder, or disorder, a therapeutically effective amount of a compound provided herein, e.g., a compound of Formula I or II, or a pharmaceutically acceptable salt, solvate, or prodrug thereof; or a pharmaceutical composition thereof.

Provided herein is a method of treating, preventing, or ameliorating one or more symptoms of a GCGR-mediated condition, disorder, or disease, comprising administering to a subject having or being suspected to have such a condition, disorder, or disease, a therapeutically effective amount of a compound provided herein, e.g., a compound of Formula I or II, or a pharmaceutically acceptable salt, solvate, or prodrug thereof; or a pharmaceutical composition thereof.

Provided herein is a method of treating, preventing, or ameliorating one or more symptoms of a condition, disorder, or disease responsive to a decrease in die hepatic glucose production or in the blood glucose level of a subject, comprising administering to the subject a therapeutically effective amount of a compound provided herein, e.g., a compound of Formula I or II, or a pharmaceutically acceptable salt, solvate, or prodrug thereof, or a pharmaceutical composition thereof.

Provided herein is a method of modulating the biological activity of a glucagon receptor, comprising contacting the receptor with one or more of the compounds provided herein, e.g., a compound of Formula I or II, or a pharmaceutically acceptable salt, solvate, or prodrug thereof; or a pharmaceutical composition thereof.

These and other aspects of the invention will be more clearly understood with reference to the following preferred embodiments and detailed description.

DETAILED DESCRIPTION a. Definitions

To facilitate understanding of the disclosure set forth herein, a number of terms are defined below.

Generally, the nomenclature used herein and the laboratory procedures in organic chemistry, medicinal chemistry, and pharmacology described herein are those well known and commonly employed in the art. Unless defined otherwise, all technical and scientific terms used herein generally have the same meaning as commonly understood by one of ordinary skill in the art to which this disclosure belongs.

The term "subject" refers to an animal, including, but not limited to, a primate (e.g., human), cow, sheep, goat, horse, dog, cat, rabbit, rat, or mouse. The terms "subject" and "patient" are used interchangeably herein in reference, for example, to a mammalian subject, such as a human subject.

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself.

The terms "prevent," "preventing," and "prevention" are meant to include a method of delaying and/or precluding the onset of a disorder, disease, or condition, and/or its attendant symptom(s); barring a subject from acquiring a disease; or reducing a subject's risk of acquiring a disorder, disease, or condition.

The term "therapeutically effective amount" are meant to include the amount of a compound that, when administered, is sufficient to prevent development of, or alleviate to some extent, one or more of the symptoms of the disorder, disease, or condition being treated. The term "therapeutically effective amount" also refers to the amount of a compound that is sufficient to elicit the biological or medical response of a cell, tissue, system, animal, or human, which is being sought by a researcher, veterinarian, medical doctor, or clinician.

The term "$IC_{50}$" refers an amount, concentration, or dosage of a compound that is required for 50% inhibition of a maximal response in an assay that measures such response.

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, excipient, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See. Remington: The Science and Practice of Pharmacy, 21st Edition, Lippincott Williams & Wilkins: Philadelphia, Pa., 2005; Handbook of Pharmaceutical Excipients, 5th Edition, Rowe et al., Eds., The Pharmaceutical Press and the American Pharmaceutical Association: 2005; and Handbook of Pharmaceutical Additives, 3rd Edition, Ash and Ash Eds., Gower Publishing Company: 2007; Pharmaceutical Preformulation and Formulation, Gibson Ed., CRC Press LLC: Boca Raton, Fla. 2004.

The term "about" or "approximately" means an acceptable error for a particular value as determined by one of ordinary skill in the art, which depends in part on bow the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The terms "active ingredient" and "active substance" refer to a compound, which is administered, alone or in combination with one or more pharmaceutically acceptable excipients, to a subject for treating, preventing, or ameliorating one or more symptoms of a condition, disorder, or disease. As used herein, "active ingredient" and "active substance" may be an optically active isomer of a compound described herein.

The terms "drug," "therapeutic agent" and "chemotherapeutic agent" refer to a compound, or a pharmaceutical composition thereof, which is administered to a subject for treating, preventing, or ameliorating one or more symptoms of a condition, disorder, or disease.

The term "naturally occurring" or "native" when used in connection with biological materials such as nucleic acid molecules, polypeptides, host cells, and the like, refers to materials which are found in nature and are not manipulated by man. Similarly, "non-naturally occurring" or "non-native" refers to a material that is not found in nature or that has been structurally modified or synthesized by man.

The term "glucagon receptor" or "GCGR" refers to a glucagon receptor protein or variant thereof, which is capable of mediating a cellular response to glucagon in vitro or in vivo. GCGR variants include proteins substantially homologous to a native GCGR. i.e., proteins having one or more naturally or non-naturally occurring amino acid deletions, insertions, or substitutions (e.g., GCGR derivatives, homologs, and fragments), as compared to the amino acid sequence of a native GCGR. In certain embodiments, the amino acid sequence of a GCGR variant is at least about 80% identical, at least about 90% identical, or at least about 95% identical to a native GCGR. In certain embodiments, the GCGR is a human glucagon receptor.

The term "glucagon receptor antagonist" or "GCGR antagonist" refers to a compound that, e.g., partially or completely blocks, decreases, prevents, inhibits, or down-regulates GCGR activity. These terms also refer to a compound that binds to, delays the activation of, inactivates, or desensitizes GCGR. A GCGR antagonist may act by interfering with the interaction of glucagon with GCGR.

The term "GCGR-mediated condition, disorder, or disease" refers to a condition, disorder, or disease characterized by inappropriate, e.g., less than or greater than normal, GCGR activity. Inappropriate GCGR functional activity might arise as the result of an increase in glucagon concentration, GCGR expression in cells which normally do not express GCGR, increased GCGR expression or degree of intracellular activation, leading to, e.g., abnormal plasma glucose levels; or decreased GCGR expression. A GCGR-mediated condition, disorder or disease may be completely or partially mediated by inappropriate GCGR activity. In particularly, a GCGR-mediated condition, disorder or disease is one in which modulation of GCGR results in some effect on the underlying symptom, condition, disorder, or disease, e.g., a GCGR antagonist results in some improvement in at least some of patients being treated.

The term "alkyl" and the prefix "alk" refers to a linear or branched saturated monovalent hydrocarbon radical, wherein the alkyl may optionally be substituted with one or more substituents. The term "alkyl" also encompasses linear, branched, and cyclic alkyl, unless otherwise specified. In certain embodiments, the alkyl is a linear saturated monovalent hydrocarbon radical that has 1 to 20 (C1-20), 1 to 15 (C1-15), 1 to 12 (C1-12), 1 to 10 (C1-10), or 1 to 6 (C1-6) carbon atoms, or branched saturated monovalent hydrocarbon radical of 3 to 20 (C3-20), 3 to 15 (C3-15), 3 to 12 (C3-12), 3 to 10 (C3-10), or 3 to 6 (C3-6) carbon atoms. As used herein, linear C1-6 and branched C3-6 alkyl groups are also referred as "lower alkyl." Examples of alkyl groups include, but are not limited to, methyl, ethyl, propyl (including all isomeric forms), n-propyl, isopropyl, butyl (including all isomeric forms), n-butyl, isobutyl, t-butyl, pentyl (including all isomeric forms), and hexyl (including all isomeric forms). For example, C1-6 alkyl refers to a linear saturated monovalent hydrocarbon radical of 1 to 6 carbon atoms or a branched saturated monovalent hydrocarbon radical of 3 to 6 carbon atoms. Cycloalkyl also includes monocyclic rings fused to an aryl group in which the point of attachment is on the non-aromatic portion. Examples of cycloalkyl include cyclopropyl, cyclobutyl, cyclopentyl, cyclohexyl, cycloheptyl, tetrahydronaphthyl, decahydronaphthyl, indanyl and the like.

The term "alkenyl" refers to a linear or branched monovalent hydrocarbon radical, which contains one or more, in one embodiment, one to five, carbon-carbon double bonds. The alkenyl may be optionally substituted with one or more substituents. The term "alkenyl" also embraces radicals having "cis" and "trans" configurations, or alternatively, "E" and "Z" configurations, as appreciated by those of ordinary skill in the art. As used herein, the term "alkenyl" encompasses both linear and branched alkenyl, unless otherwise specified. For example, C2-6 alkenyl refers to a linear unsaturated monovalent hydrocarbon radical of 2 to 6 carbon atoms or a branched unsaturated monovalent hydrocarbon radical of 3 to 6 carbon atoms. In certain embodiments, the alkenyl is a linear monovalent hydrocarbon radical of 2 to 20 (C2-20), 2 to 15 (C2-15), 2 to 12 (C2-12), 2 to 10 (C2-10), or 2 to 6 (C2-6) carbon atoms, or a branched monovalent hydrocarbon radical of 3 to 20 (C3-20), 3 to 15 (C3-15), 3 to 12 (C3-12), 3 to 10 (C3-10), or 3 to 6 (C3-6) carbon atoms. Examples of alkenyl groups include, but are not limited to, vinyl, isopropenyl, pentenyl, hexenyl, heptenyl, ethenyl, propen-1-yl, propen-2-yl, allyl, butenyl, 2-butenyl, 2-methyl-2-butenyl, 4-methylbutenyl, and the like.

The term "alkynyl" refers to a linear or branched monovalent hydrocarbon radical, which contains one or more, in one embodiment, one to five, carbon-carbon triple bonds. The alkynyl may be optionally substituted with one or more substituents. The term "alkynyl" also encompasses both linear and branched alkynyl, unless otherwise specified. In certain embodiments, the alkynyl is a linear monovalent hydrocarbon radical of 2 to 20 (C2-20), 2 to 15 (C2-15), 2 to 12 (C2-12), 2 to 10 (C2-10), or 2 to 6 (C2-6) carbon atoms, or a branched monovalent hydrocarbon radical of 3 to 20 (C3-20), 3 to 15 (C3-15), 3 to 12 (C3-12), 3 to 10 (C3-10), or 3 to 6 (C3-6) carbon atoms. Examples of alkynyl groups include, but are not limited to, ethynyl (—C≡CH), propargyl (—CH2C≡CH), 3-methyl-1-pentynyl, 2-heptynyl, and the like. For example, C2-6 alkynyl refers to a linear unsaturated monovalent hydrocarbon radical of 2 to 6 carbon atoms or a branched unsaturated monovalent hydrocarbon radical of 3 to 6 carbon atoms.

The term "cycloalkyl" refers to a cyclic saturated bridged and/or non-bridged monovalent hydrocarbon radical, which may be optionally substituted with one or more substituents. In certain embodiments, the cycloalkyl has from 3 to 20 (C3-20), from 3 to 15 (C3-15), from 3 to 12 (C3-12), from 3 to 10 (C3-10), or from 3 to 7 (C3-7) carbon atoms.

Examples of cycloalkyl groups include, but are not limited to, cyclopropyl, cyclobutyl, cyclopentyl, cyclohexyl, cycloheptyl, decalinyl, and adamantyl.

The term "cycloalkenyl" refers to a cyclic unsaturated bridged and/or non-bridged monovalent hydrocarbon radical, which contains one or more double bonds in its ring. The cycloalkenyl may be optionally substituted with one or more substituents. In certain embodiments, the cycloalkenyl has from 3 to 20 (C3-20), from 3 to 15 (C3-15), from 3 to 12 (C3-12), from 3 to 10 (C3-10), or from 3 to 7 (C3-7) carbon atoms.

The term "aryl" (Ar) refers to a monocyclic aromatic group and/or multicyclic monovalent aromatic group that contain at least one aromatic hydrocarbon ring. In certain embodiments, the aryl has from 6 to 20 (C6-20), from 6 to 15 (C6-15), or from 6 to 10 (C6-10) ring atoms. Examples of aryl groups include, but are not limited to, phenyl, naphthyl, fluorenyl, azulenyl, anthryl, phenanthryl, pyrenyl, biphenyl, and terphenyl. Aryl also refers to bicyclic or tricyclic carbon rings, where one of the rings is aromatic and the others of which may be saturated, partially unsaturated, or aromatic, for example, dihydronaphthyl, indenyl, indanyl, or tetrahydronaphthyl (tetralinyl). In certain embodiments, aryl may also be optionally substituted with one or more substituents.

The term "aralkyl" or "aryl-alkyl" refers to a monovalent alkyl group substituted with aryl. In certain embodiments, both alkyl and aryl may be optionally substituted with one or more substituents.

The term "heteroaryl" (HAR) refers to a monocyclic aromatic group and/or multicyclic aromatic group that contain at least one aromatic ring, wherein at least one aromatic ring contains one or more heteroatoms independently selected from O, S, and N. In some embodiments, each ring contains 5 to 6 atoms. Each ring of a heteroaryl group can contain one or two O atoms, one or two S atoms, and/or one to four N atoms, provided that the total number of heteroatoms in each ring is four or less and each ring contains at least one carbon atom. The heteroaryl may be attached to the main structure at any heteroatom or carbon atom which results in the creation of a stable compound. In certain embodiments, the heteroaryl has from 5 to 20, from 5 to 15, or from 5 to 10 ring atoms. Examples of monocyclic heteroaryl groups include, but are not limited to, pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyramidyl, pyridazinyl, triazolyl, tetrazolyl, and triazinyl. Examples of bicyclic heteroaryl groups include, but are not limited to, indolyl, benzothiazolyl, benzoxazolyl, benzothienyl, benzothiophenyl, furo(2,3-b) pyridyl, quinolinyl, tetrahydroisoquinolinyl, isoquinolyl, isoquinolinyl, benzimidazolyl, benzopyranyl, indolizinyl, benzofuranyl, isobenzofuranyl, chromonyl, coumarinyl, cinnolinyl, quinoxalinyl, indazolyl, purinyl, pyrrolopyridinyl, furopyridinyl, thienopyridinyl, dihydroisoindolyl, and tetrahydroquinolinyl. Examples of tricyclic heteroaryl groups include, but are not limited to, carbazolyl, benzindolyl, phenanthrolinyl, acridinyl, phenanthridinyl, and xanthenyl. In certain embodiments, heteroaryl may also be optionally substituted with one or more substituents. Heteroaryl also includes aromatic heterocyclic groups fused to heterocycles that are non-aromatic or partially aromatic, and aromatic heterocyclic groups fused to cycloalkyl rings. Heteroaryl also includes such groups in charged form, e.g., pyridinium.

The term "heterocyclyl" (Hetcy) or "heterocyclic" refers to a monocyclic non-aromatic ring system and/or multicyclic ring system that contains at least one non-aromatic ring, wherein one or more of the non-aromatic ring atoms are heteroatoms independently selected from O, S, or N; and the remaining ring atoms are carbon atoms. In certain embodiments, the heterocyclyl or heterocyclic group has from 3 to 20, from 3 to 15, from 3 to 10, from 3 to 8, from 4 to 7, or from 5 to 6 ring atoms. In certain embodiments, the heterocyclyl is a monocyclic, bicyclic, tricyclic, or tetracyclic ring system, which may include a fused or bridged ring system, and in which the nitrogen or sulfur atoms may be optionally oxidized, the nitrogen atoms may be optionally quaternized, and some rings may be partially or fully saturated, or aromatic. The heterocyclyl may be attached to the main structure at any heteroatom or carbon atom which results in the creation of a stable compound. Examples of such heterocyclic radicals include, but are not limited to benzoxazinyl, benzodioxanyl, benzodioxolyl, benzopyranonyl, benzopyranyl, benzotetrahydrofuranyl, benzotetrahydrothienyl, benzothiopyranyl, chromanyl, chromonyl, coumarinyl, decahydroisoquinolinyl, dihydrobenzisothiazinyl, dihydrobenzisoxazinyl, 2,3-dihydrofuro(2,3-b)pyridyl, dihydrofuryl, dihydroindolyl, dihydropyranyl, dioxolanyl, dihydropyrazinyl, dihydropyridinyl, dihydropyrazolyl, dihydropyrimidinyl, dihydropyrrolyl, 1,4-dithianyl, imidazolidinyl, imidazolinyl, indolinyl, isobenzotetrahydrofuranyl, isobenzotetrahydrothienyl, isochromanyl, isocoumarinyl, isoindolinyl, isothiazolidinyl, isoxazolidinyl, morpholinyl, octahydroindolyl, octahydroisoindolyl, oxazolidinonyl, oxazolidinyl, oxiranyl, quinuclidinyl, tetrahydrofuryl, tetrahydrofuranyl, tetrahydroquinolinyl, tetrahydroisoquinolinyl, tetrahydropyranyl, tetrahydrothienyl, thiamorpholinyl, thiazolidinyl, and 1,3,5-trithianyl. Heterocyclyl/heterocyclic also includes partially unsaturated monocyclic rings that are not aromatic, such as 2- or 4-pyridones attached through the nitrogen or N-substituted-(1H,3H)-pyrimidine-2,4-diones (N-substituted uracils). Heterocyclyl/heterocyclic also includes such moieties in charged form, e.g., piperidinium. In certain embodiments, heterocyclyl/heterocyclic may also be optionally substituted with one or more substituents.

The term "alkoxy" refers to an —OR radical, wherein R is, for example, alkyl, alkenyl, alkynyl, cycloalkyl, aryl, heteroaryl, or heterocyclyl, each as defined herein. When R is aryl, it is also known as aryloxy. Examples of alkoxy groups include, but are not limited to, methoxy, ethoxy, propoxy, n-propoxy, 2-propoxy, n-butoxy, isobutoxy, tert-butoxy, cyclohexyloxy, phenoxy, benzoxy, and 2-naphthyloxy. In certain embodiments, alkoxy may also be optionally substituted with one or more substituents.

The term "acyl" refers to a —C(O)R radical, wherein R is, for example, hydrogen, alkyl, alkenyl, alkynyl, cycloalkyl, aryl, heteroaryl, or heterocyclyl, each as defined herein. Examples of acyl groups include, but are not limited to, formyl, acetyl, propionyl, butanoyl, isobutanoyl, pentanoyl, hexanoyl, heptanoyl, octanoyl, nonanoyl, decanoyl, dodecanoyl, tetradecanoyl, hexadecanoyl, octadecanoyl eicosanoyl, docosanoyl, myristoleoyl, palmitoleyl, oleoyl, linoleoyl, arachidonoyl, benzoyl, pyridinylcarbonyl, and furoyl. In certain embodiments, acyl may also be optionally substituted with one or more substituents.

The term "halogen", "halide" or "halo" (Halo) refers to fluorine, chlorine, bromine, and/or iodine.

The term "optionally substituted" is intended to mean that a group, including alkyl, alkoxy, acyl, alkyl-cycloalkyl, hydroxyalkyl, alkenyl, alkynyl, cycloalkyl, cycloalkenyl, cycloalkynyl, cycloalkylalkyl, aryl, aryloxy, aralkyl, arylalkenyl, aryl-alkynyl, heteroaryl, heteroarylalkyl, heteroaryl-alkenyl, heteroaryl-alkynyl, and heterocyclyl, or acyl, may be substituted with one or more substituents, in one embodiment, one, two, three, four substituents, where in some embodiments each substituent is independently selected from the group consisting of cyano, halo, oxo, nitro, $C_{1-6}$ alkyl, $C_{2-6}$ alkenyl, $C_{2-6}$ alkynyl, $C_{3-7}$ cycloalkyl, $C_{6-14}$ aryl, heteroaryl, heterocyclyl, —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^f$, —NR$^e$C(O)OR$^f$, —NR$^e$C(O)NR$^f$R$^g$, —NR$^e$C(=NR$^h$)NR$^f$R$^g$, —NR$^e$S(O)R$^f$, —NR$^e$S(O)$_2$R$^f$, —NR$^e$S(O)NR$^f$R$^g$, —NR$^e$S(O)$_2$NR$^f$R$^g$, —SR$^e$, —S(O)R$^e$, —S(O)$_2$R$^e$, and —S(O)$_2$NR$^f$R$^g$, wherein each R$^e$, R$^f$, R$^g$, and R$^h$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl; or R$^f$ and R$^g$ together with the N atom to which they are attached form heterocyclyl.

The term "optically active" refers to a collection of molecules, which has an enantiomeric excess of no less than about 50%, no less than about 70%, no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%.

In describing an optically active compound, the prefixes R and S are used to denote the absolute configuration of the molecule about its chiral centers). The (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the molecule, R and S.

The term "solvate" refers to a compound provided herein or a salt thereof, which further includes a stoichiometric or non-stoichiometric amount of solvent bound by non-covalent intermolecular forces. Where the solvent is water, the solvate is a hydrate.

"Binding" means the specific association of the compound of interest to the target of interest, e.g., a receptor.

The term "crystalline" and related terms used herein, when used to describe a substance, component or product, means that the substance, component or product is crystalline as determined by X-ray diffraction. See. e.g., *Remington's Pharmaceutical Sciences*, 18$^{th}$ ed, Mack Publishing, Easton Pa. 173 (1990): *The United States Pharmacopeia*. 23$^{rd}$ ed., 1843-1844 (1995).

"Co-crystal" as used herein means a crystalline material comprised of two or more unique solids at room temperature that are H-bonded.

"Diabetes" refers to a heterogeneous group of disorders that share impaired glucose tolerance in common. Its diagnosis and characterization, including pre-diabetes, type I and type II diabetes, and a variety of syndromes characterized by impaired glucose tolerance, impaired fasting glucose, and abnormal glycosylated hemoglobin, are well known in the art. It may be characterized by hyperglycemia, glycosuria, ketoacidosis, neuropathy or nephropathy, increased hepatic glucose production, insulin resistance in various tissues, insufficient insulin secretion and enhanced or poorly controlled glucagon secretion from the pancreas.

The term "drug" refers to a compound, or a pharmaceutical composition thereof, which is administered to a subject for treating, preventing, or ameliorating one or more symptoms of a condition, disorder, or disease.

The term "EC$_{50}$" refers an amount, concentration, or dosage of a compound at which 50% of a maximal response is observed in an assay that measures such response.

The term "percent enantiomeric excess (% ee)" refers to optical purity. It is obtained by using the following formula:

$$\frac{[R]-[S]}{[R]+[S]} \times 100 = \% R - \% S$$

where [R] is the amount of the R isomer and [S] is the amount of the S isomer. This formula provides the % ee when R is the dominant isomer.

The term "enantiomerically pure" refers to a compound which comprises at least about 80% by weight of the designated enantiomer and at most about 20% by weight of the other enantiomer or other stereoisomer(s), at least about 90% by weight of the designated enantiomer and at most about 10% by weight of the other enantiomer or other stereoisomers), at least about 95% by weight of the designated enantiomer and at most about 5% by weight of the other enantiomer or other stereoisomers), at least about 96.6% by weight of the designated enantiomer and at most about 3.4% by weight of the other enantiomer or other stereoisomers), at least about 97% by weight of the designated enantiomer and at most about 3% by weight of the other enantiomer or other stereoisomers), at least about 99% by weight of the designated enantiomer and at most about 1% by weight of the other enantiomer or other stereoisomers), or at least about 99.9% by weight of the designated enantiomer and at most about 0.1% by weight of the other enantiomer or other stereoisomers). In certain embodiments, the weights are based upon total weight of the compound.

As used in connection with the compounds of Formula I and II disclosed herein, the terms "R-isomer" and "R-enantiomer" refer to the configuration R of the aliphatic carbon which is alpha to the —C(O)NH— group. Formula I below shows the R-stereochemistry.

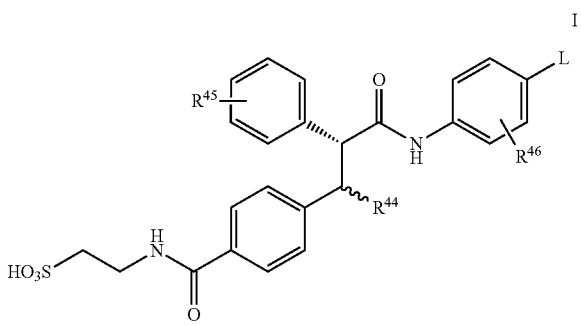

The term "chiral" as used herein includes a compound that has the property that it is not superimposable on its mirror image.

"Insulin resistance" is defined clinically as the impaired ability of a known quantity of exogenous or endogenous insulin to increase whole body glucose uptake and utilization.

"Impaired glucose tolerance (IGT)" refers to a condition known to precede the development of overt Type 2 diabetes. It is characterized by abnormal blood glucose excursions following a meal. The criteria for diagnosing and characterizing impaired glucose tolerance and related syndromes are well known in the art.

"Lower" referred to herein in connection with organic radicals or compounds respectively defines such radicals or compounds as containing up to and including 6 carbon atoms. One aspect provides organic radicals or compounds as containing up to and including 4 carbon atoms. Yet another aspect provides organic radicals or compounds that contain one to three carbon atoms. Such groups may be straight chain, branched, or cyclic.

"Metabolic disease" includes diseases and conditions such as obesity, diabetes and lipid disorders such as hypercholesterolemia, hyperlipidemia, hypertriglyceridemia as well as disorders that are associated with abnormal levels of lipoproteins, lipids, carbohydrates and insulin such as metabolic syndrome X, diabetes, impaired glucose tolerance, atherosclerosis, coronary artery disease, cardiovascular disease. The criteria for diagnosing and characterizing these conditions and related syndromes are well known in the art.

"Prodrug" as used herein refers to any compound that when administered to a biological system generates a biologically active compound as a result of spontaneous chemical reaction(s), enzyme catalyzed chemical reaction(s), and/or metabolic chemical reaction(s), or a combination of each. Standard prodrugs are formed using groups attached to functionality, e.g., HO—, HS—, HOOC—, —NHR, associated with the drug, that cleave in vivo. Standard prodrugs include but are not limited to carboxylate esters where the group is alkyl, aryl, aralkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. The groups illustrated are exemplary, not exhaustive, and one skilled in the art could prepare other known varieties of prodrugs. Such prodrugs of the compounds of Formula I or II disclosed herein fall within this scope. Prodrugs must undergo some form of a chemical transformation to produce the compound that is biologically active or is a precursor of the biologically active compound. In some cases, the prodrug is biologically active, usually less than the drug itself, and serves to improve drug efficacy or safety through improved oral bioavailability, and/or pharmacodynamic half-life, etc. Prodrug forms of compounds may be utilized, for example, to improve bioavailability, improve subject acceptability such as by masking or reducing unpleasant characteristics such as bitter taste or gastrointestinal irritability, alter solubility such as for intravenous use, provide for prolonged or sustained release or delivery, improve ease of formulation, or provide site-specific delivery of the compound. Prodrugs are described in The Organic Chemistry of Drug Design and Drug Action, by Richard B. Silverman, Academic Press, San Diego, 1992. Chapter 8: "Prodrugs and Drug delivery Systems" pp.352-401: Design of Prodrugs, edited by H. Bundgaard. Elsevier Science, Amsterdam, 1985; Design of Biopharmaceutical Properties through Prodrugs and Analogs, Ed. by E. B. Roche, American Pharmaceutical Association, Washington. 1977; and Drug Delivery Systems, ed. by R. L. Juliano, Oxford Univ. Press, Oxford, 1980.

b. Compounds

One aspect provides for compounds of Formula I

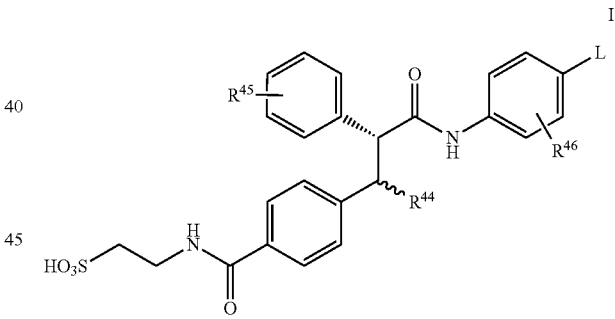

wherein:
$R^{44}$ is H, $CH_3$ or $CH_3CH_2$;
$R^{45}$ is $C_{1-6}$-alkyl, alkenyl, alkoxy, $C_{3-6}$-cycloalkyl, $C_{4-8}$-cycloalkenyl, $C_{4-8}$-bicycloalkenyl, aryl or heteroaryl, any of which can be optionally substituted with one or more substituents selected from $C_{1-6}$alkyl, $CF_3$, F, CN or $OCF_3$;
L is phenyl, indenyl, benzoxazol-2-yl or 4,4-dimethylcyclohexenyl, any of which can be optionally substituted with one or more substituents selected from F, Cl, $CH_3$, $CF_3$, $OCF_3$ or CN; and
$R^{46}$ represents one or more substituents selected from H, F, Cl, $CH_3$, $CF_3$, $OCF_3$ or CN.

In certain embodiments according to Formula I, the configuration of the aliphatic carbon which is alpha to the —C(O)NH— group is R.

In other embodiments according to Formula I. L is substituted with one or more substituents independently selected from F, Cl, $CH_3$, $CF_3$, $OCF_3$ or CN. In another embodiment. L is phenyl, benzoxazol-2-yl or 4,4-dimethyl-cyclohexenyl, any of which can be optionally substituted with one or more substituents. In another embodiment, L is 4-chloro-2-methylphenyl, 4-methyl-2-benzoxazolyl, 2,4,6-trimethylphenyl, benzoxazol-2-yl, 4-chloro-3-methylphenyl or 4,4-dimethylcyclohexenyl.

In another embodiment, $R^{44}$ is H or $CH_3$. In another embodiment, $R^{44}$ is H.

In certain embodiments, $R^{45}$ is attached to the 3 (meta) or 4 (para) position. In another embodiment, $R^{45}$ is attached to the 4 (para) position. In another embodiment, $R^{45}$ is alkenyl, $C_{3-6}$-cycloalkyl, $C_{4-8}$-cycloalkenyl, $C_{4-8}$-bicycloalkenyl or phenyl, any of which can be optionally substituted with one or more substituents. In yet other embodiments according to Formula I, $R^{45}$ is selected from $(CH_3)_3CCH=CH-$, t-butyl-cycloalkyl-, dimethyl-cycloalkyl-, t-butyl-cycloalkenyl-, dimethyl-cycloalkenyl-, bicycloalkenyl or phenyl-.

In certain embodiments according to Formula I. $R^{45}$ is substituted with one or more substituents independently selected from $CH_3$ and $(CH_3)_3C-$.

In certain embodiments according to Formula I, $R^{45}$ is trans-t-butylvinyl, cis-4-t-butylcyclohexyl, trans-4-t-butyl-cyclohexyl, 4,4-dimethylcyclohexyl, cyclohex-1-enyl, (S)-4-t-butylcyclohex-1-enyl, (R)-4-t-butylcyclohex-1-enyl, 4,4-dimethylcyclohex-1-enyl, 4,4-diethylcyclohex-1-enyl, 4,4-diethylcyclohexyl, 4,4-dipropylcyclohex-1-enyl, 4,4-dipropylcyclohexyl, 4,4-dimethylcyclohexa-1,5-dienyl. (1R,4S)-1,7,7-trimethylbicyclo[2.2.1]3-heptyl-2-ene, (1R,4R)-1,7,7-trimethylbicyclo[2.2.1]2-heptyl-2-ene, 2-methyl-4-chloro-phenyl, 2,4,6-trimethylphenyl or 4-t-butylphenyl.

In certain embodiments according to Formula I. $R^{45}$ is trans-t-butylvinyl, cis-4-t-butylcyclohexyl, trans-4-t-butyl-cyclohexyl, 4,4-dimethylcyclohexyl, (S)-4-t-butylcyclohex-1-enyl, (R)-4-t-butylcyclohex-1-enyl, 4,4-dimethylcyclohex-1-enyl, (1R,4R)-1,7,7-trimethylbicyclo[2.2.1]2-heptyl-2-ene or 4-t-butylphenyl.

In another embodiment, $R^{46}$ is H or $CH_3$. In another embodiment. $R^{46}$ is H.

In certain embodiments, the compound of Formula I is one presented below in Table 1:

TABLE 1

Certain Compounds of Formula I

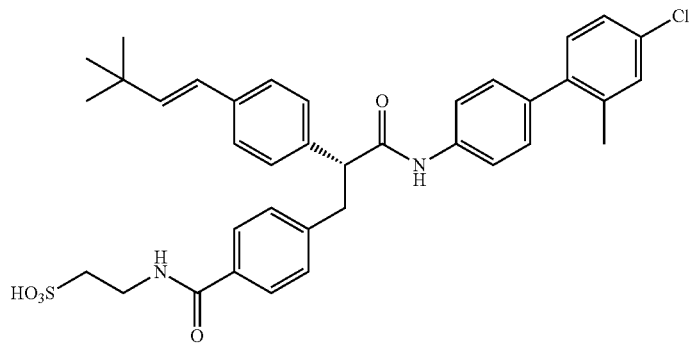 [SMILES: Cc1cc(Cl)ccc1-c1ccc(NC(=O)[C@H](Cc2ccc(C(=O)NCCS(=O)(=O)O)cc2)c2ccc(/C=C/C(C)(C)C)cc2)cc1]

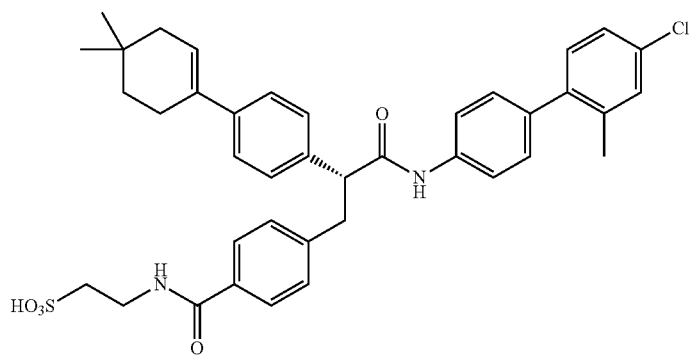 [SMILES: Cc1cc(Cl)ccc1-c1ccc(NC(=O)[C@H](Cc2ccc(C(=O)NCCS(=O)(=O)O)cc2)c2ccc(C3=CCC(C)(C)CC3)cc2)cc1]

TABLE 1-continued
Certain Compounds of Formula I
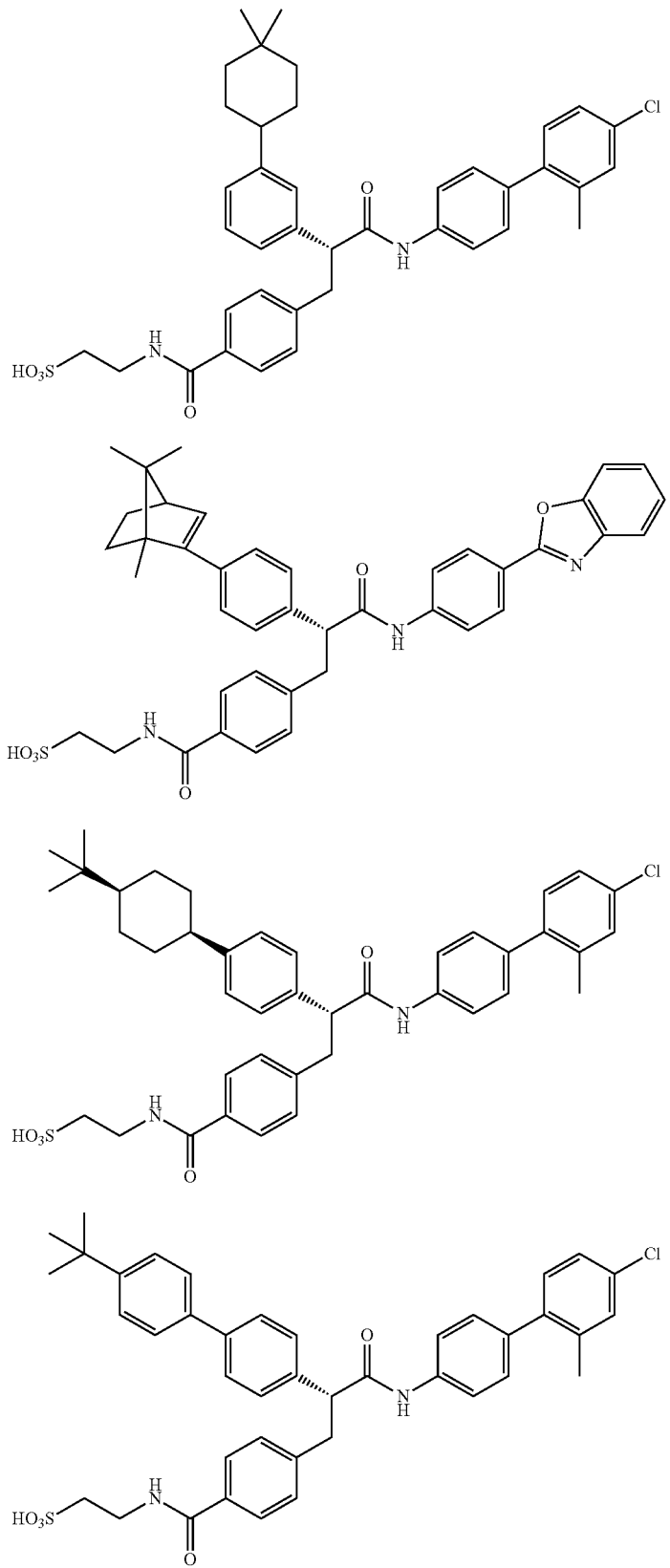

TABLE 1-continued
Certain Compounds of Formula I
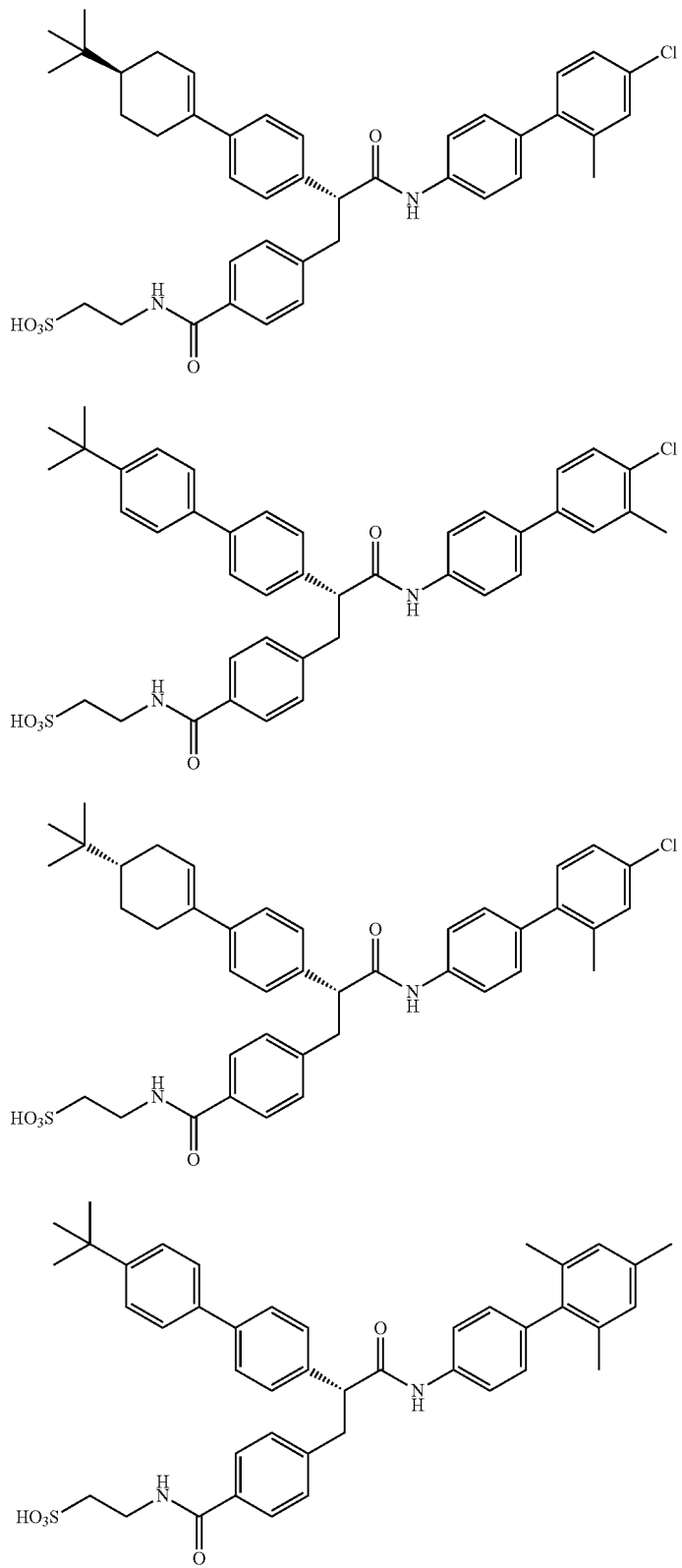

TABLE 1-continued
Certain Compounds of Formula I
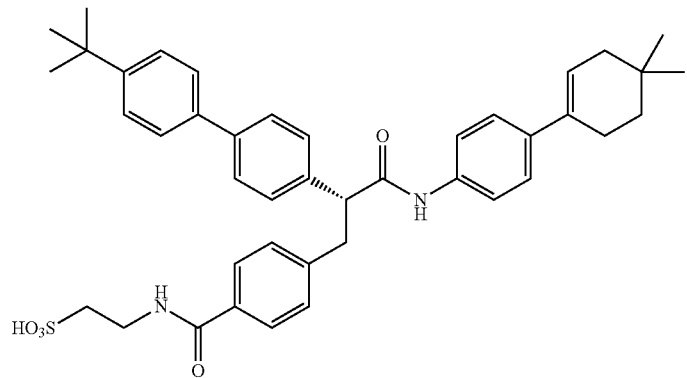 [SMILES: CC1(C)CC=C(c2ccc(NC(=O)[C@H](Cc3ccc(C(=O)NCCS(=O)(=O)O)cc3)c3ccc(-c4ccc(C(C)(C)C)cc4)cc3)cc2)CC1]
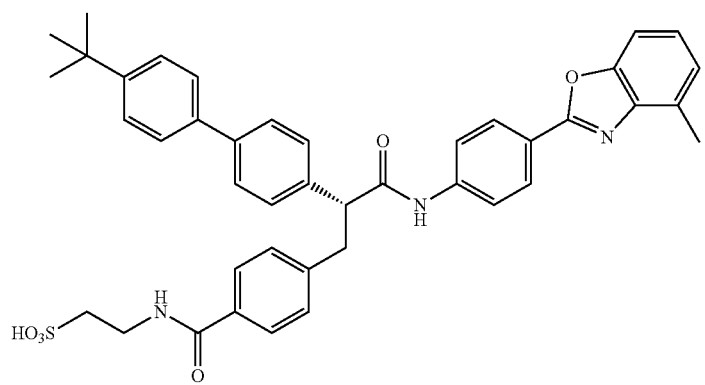 [SMILES: Cc1cccc2oc(-c3ccc(NC(=O)[C@H](Cc4ccc(C(=O)NCCS(=O)(=O)O)cc4)c4ccc(-c5ccc(C(C)(C)C)cc5)cc4)cc3)nc12]
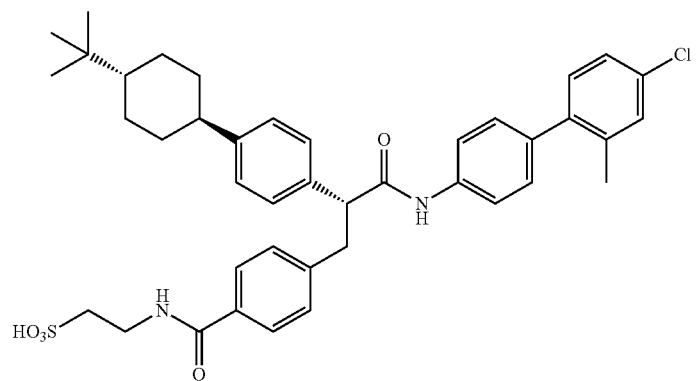 [SMILES: Cc1cc(Cl)ccc1-c1ccc(NC(=O)[C@H](Cc2ccc(C(=O)NCCS(=O)(=O)O)cc2)c2ccc([C@H]3CC[C@H](C(C)(C)C)CC3)cc2)cc1]

Another aspect provides for compounds, prodrugs thereof, and compositions comprising the compounds or prodrugs thereof wherein the compound is a structure of Formula II:

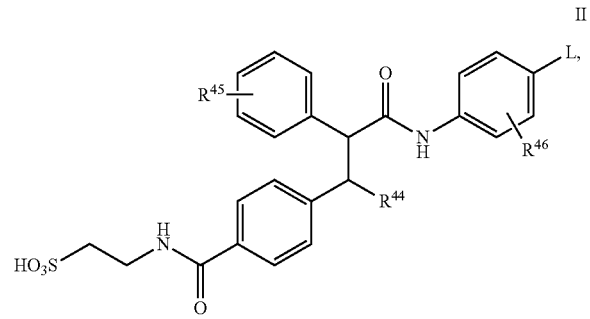

wherein:

R$^{44}$ is H;

R$^{45}$ is cis-4-t-butylcyclohexyl, trans-4-t-butylcyclohexyl, 4,4-dimethylcyclohexyl, 4,4-diethylcyclohexyl, 4,4-dipropylcyclohexyl, 4,4-diethylcyclohex-1-enyl, 4,4-dimethylcyclohex-1-enyl, (S)-4-t-butylcyclohex-1-enyl, (R)-4-t-butylcyclohex-1-enyl, 4,4-dipropylcyclohex-1-enyl, 4-t-butylphenyl, (1R,4S)-1,7,7-trimethylbicyclo[2.2.1]-3-hept-2-enyl or (1R,4R)-1,7,7-trimethylbicyclo[2.2.1]-2-hept-2-enyl;

L is phenyl, benzoxazol-2-yl, 4-alkyl-cyclohex-1-enyl, 4,4-dialkylcyclohex-1-enyl, 4-alkyl-cyclohexyl, 4,4-dialkylcyclohexyl or 4,4-dimethylcyclohexenyl, any of which can be optionally substituted with one or more substituents selected from F, Cl, CH$_3$, CF$_3$, OCF$_3$ or CN; and R$^{46}$ is H.

In certain embodiments according to Formula II, L is substituted with one or more substituents independently selected from Cl or CH$_3$. In another embodiment, L is phenyl, benzoxazol-2-yl or 4,4-dimethylcyclohexenyl, any of which can be optionally substituted with one or more substituents selected from Cl or CH$_3$.

In certain embodiments according to Formula II, R$^{45}$ is attached to the 3 (meta) or 4 (para) position. In another embodiment, R$^{45}$ is attached to the 4 (para) position.

In another embodiment, R$^{45}$ is cis-4-t-butylcyclohexyl, trans-4-t-butylcyclohexyl, 4,4-dimethylcyclohexyl, (S)-4-t-butylcyclohex-1-enyl, (R)-4-t-butylcyclohex-1-enyl, 4,4-dipropykyclohex-1-enyl, 4-t-butylphenyl, (1R,4S)-1,7,7-trimethylbicyclo[2.2.1]-3-hept-2-enyl or (1R,4R)-1,7,7-trimethylbicyclo[2.2.1]-2-hept-2-enyl. In other embodiments, R$^{45}$ is cis-4-t-butylcyclohexyl, 4,4-dimethylcyclohexyl, (S)-4-t-butylcyclohex-1-enyl, (R)-44-butylcyclohex-1-enyl, 4-t-butylphenyl or (1R,4S)-1,7,7-trimethylbicyclo[2.2.1]-3-hept-2-enyl.

In certain embodiments the compound of Formula II is also a compound of Formula I.

In certain embodiments according to Formula II, the configuration of the aliphatic carbon which is alpha to the —C(O)NH— group is R.

In certain embodiments, the compounds of Formula II are a racemic mixture.

Another aspect provides for enantiomerically pure compounds of Formula I or II. In certain embodiments, a single enantiomer is >60%, >70%, >80%, >85%, >90%, >91%, >92%, >93%, >94%, >95%, >96%, >97%, >98% or >99% as compared to the total percentage of all other enantiomers of the same compound or other diastereomers present in the composition.

Another aspect provides enantiomerically pure compounds of Formula I or II. In certain embodiments, the compound comprises at least about 80% by weight of the designated enantiomer and at most about 20% by weight of the other enantiomer or other stereoisomer(s). In certain embodiments, the compound comprises at least about 90% by weight of the designated enantiomer and at most about 10% by weight of the other enantiomer or other stereoisomers). In certain embodiments, the compound comprises at least about 95% by weight of the designated enantiomer and at most about 5% by weight of the other enantiomer or other stereoisomers). In certain embodiments, the compound comprises at least about 96.6% by weight of the designated enantiomer and at most about 3.4% by weight of the other enantiomer or other stereoisomers). In certain embodiments, the compound comprises at least about 97% by weight of the designated enantiomer and at most about 3% by weight of the other enantiomer or other stereoisomers). In certain embodiments, the compound comprises at least about 99% by weight of the designated enantiomer and at most about 1% by weight of the other enantiomer or other stereoisomers). In certain embodiments, the compound comprises at least about 99.9% by weight of the designated enantiomer and al most about 0.1% by weight of the other enantiomer or other stereoisomers). In certain embodiments, the weights are based upon total weight of the compound.

Another aspect provides for salts, including pharmaceutically acceptable salts, of compounds of Formula I or II and pharmaceutical compositions comprising a pharmaceutically acceptable salt of compounds of Formula I or II. Salts of compounds of Formula I or II include an inorganic base addition salt such as sodium, potassium, lithium, calcium, magnesium, ammonium, aluminum salts or organic base addition salts.

Another aspect provides for anhydrates, hydrates and solvates of compounds of Formula I or II and pharmaceutical compositions comprising a pharmaceutically acceptable anhydrates, hydrates and solvates of compounds of Formula I or II. Included are an anhydrate, hydrate or solvate of a free form or salt of a compound of Formula I or II. Hydrates include, for example, a hemihydrate, monohydrate, dihydrate, trihydrate, quadrahydrate, pentahydrate, sesquihydrate.

In certain embodiments, the compounds of Formula I or II are able to displace radiolabeled glucagon from the human glucagon receptor by at least 15% at 1000 nM. In one embodiment, the compounds of Formula I or II are able to displace at least 20%, 30%, 40%, 50%, 60%, 70%, 80%, 90%, 95%, 96%, 97%, 98%, or 99% of radiolabeled glucagon from the human glucagon receptor as described in Example A.

Alternatively, the activities of the compounds of Formula I or II can be described in terms of the concentrations of compounds required for displacement of 50% of the radiolabeled glucagon from the human glucagon receptor (the IC$_{50}$ values) according to the methods of Example A. In one embodiment the IC$_{50}$ values for the compounds of Formula I are less than <10,000 nM, 9,000 nM, 8.000 nM, 7,000 nM, 6,000 nM, 5.000 nM, 4.000 nM, 3.000 nM, 2,000 nM, 1.000 nM, 900 nM, 800 nM, 700 nM, 600 nM, 500 nM, 400 nM, 300 nM, 200 nM, 100 nM, 90 nM, 80 nM, 70 nM, 60 nM, 50 nM, 40 nM, 30 nM, 25 nM, 20 nM, 15 nM, 10 nM or 5 nM.

In another alternative, the activities of the compounds of Formula I or II can be described in terms of the concentrations of compounds required for functional antagonism of glucagon in hepatocytes from various species. The EC$_{50}$ is determined using the method of Example B. In one embodiment the $EC_{50}$ values for the compounds of Formula I or II are less than <10,000 nM, 9,000 nM, 8.000 nM, 7,000 nM, 6,000 nM, 5,000 nM, 4,000 nM, 3.000 nM, 2.000 nM, 1,000 nM, 900 nM, 800 nM, 700 nM, 600 nM, 500 nM, 400 nM, 300 nM, 200 nM, 100 nM, 90 nM, 80 nM, 70 nM, 60 nM, 50 nM, 40 nM, 30 nM, 25 nM, 20 nM, 15 nM, 10 nM or 5 nM.

The compounds of Formula I or II disclosed herein also exhibit the ability to reduce blood glucose in an animal. In certain aspects, circulating blood glucose in fasting or non-fasting (freely-feeding) animals can be reduced between 10% and 100%. A reduction of 100% refers to complete normalization of blood glucose levels, not 0% blood glucose levels. Normal blood glucose in rats, for example, is approximately 80 mg/dl (fasted) and approximately 120 mg/dl (fed). Thus, contemplated herein is a method for reducing excessive circulating blood glucose levels in fasting or freely fed animals (e.g. rat), by administered 10 mg/kg of a compound of Formula I, by at least 10%, 20%, 30%, 40%, 50%, 60%, 70%, 80%, 90%, 95%, or 99%.

c. Administration

Provided herein are pharmaceutical compositions including a compound provided herein as an active ingredient, e.g., a compound of Formula I or II, or a pharmaceutically acceptable salt, solvate, or prodrug thereof; in combination with a pharmaceutically acceptable vehicle, carrier, diluent, excipient, or a mixture thereof.

The pharmaceutical compositions may be formulated in various dosage forms, including, but limited to, the dosage forms for oral, parenteral, subcutaneous, intramuscular, transmucosal, inhaled, or topical/transdermal administration. The pharmaceutical compositions may also be formulated as modified release dosage forms, including, but not limited to, delayed-, extended-, prolonged-, sustained-, pulsatile-, controlled-, accelerated- and fast-, targeted-, programmed-release, and gastric retention dosage forms. These dosage forms can be prepared according to conventional methods and techniques known to those skilled in the art (see. Remington: The Science and Practice of Pharmacy, supra; Modified-Release Drug Deliver Technology. Rathbone et al., Eds., Drugs and the Pharmaceutical Science. Marcel Dekker, Inc.: New York, N.Y., 2003; Vol. 126).

The pharmaceutical compositions provided herein may be provided in a unit- or multiple-dosage form. A unit-dosage form, as used herein, refers to a physically discrete unit suitable for administration to a subject as is known in the art. Examples of a unit-dosage form include an ampoule, syringe, and individually packaged tablet and capsule. A unit-dosage form may be administered in fractions or multiples thereof.

The pharmaceutical compositions provided herein may be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens can be adjusted over time according to the individual need and the professional judgment of the person administering or supervising the administration of the pharmaceutical compositions provided herein.

Exemplary pharmaceutical compositions and components for use therewith are described in U.S. Provisional Application No. 61/088,697, the contents of which are herein incorporated by reference.

d. Methods of Use

In one embodiment, provided herein is a method of treating, preventing, or ameliorating one or more symptoms of a condition, disorder, or disease associated with impaired glucose tolerance, a metabolic syndrome, or a glucagon receptor, comprising administering to a subject having or being suspected to have such a condition, disorder, or disease, a therapeutically effective amount of a compound provided herein, e.g., a compound of Formula I or II, or a pharmaceutically acceptable salt solvate, or prodrug thereof; or a pharmaceutical composition thereof. In one embodiment the subject is a mammal. In another embodiment the subject is a human.

In another embodiment provided herein is a method of treating, preventing, or ameliorating one or more symptoms of a condition, disorder, or disease responsive to a decrease in the hepatic glucose production or in the blood glucose level of a subject, comprising administering to the subject having or being suspected to have such a condition, disorder, or disease, a therapeutically effective amount of a compound provided herein, e.g., a compound of Formula I or II, or a pharmaceutically acceptable salt, solvate, or prodrug thereof; or a pharmaceutical composition thereof. In one embodiment, the subject is a mammal. In another embodiment, the subject is a human.

The conditions and diseases treatable with the methods provided herein include, but are not limited to, type 1 diabetes, type 2 diabetes, gestational diabetes, ketoacidosis, nonketotic hyperosmolar coma (nonketotic hyperglycemia), impaired glucose tolerance (IGT), insulin resistance syndromes, syndrome X, low HDL levels, high LDL levels, hyperglycemia, hyperinsulinemia, hyperlipidemia, hypertriglyceridemia, hyperlipoproteinemia, hypercholesterolemia, dyslipidemia, arteriosclerosis, atherosclerosis, glucagonomas, acute pancreatitis, cardiovascular diseases, hypertension, cardiac hypertrophy, gastrointestinal disorders, obesity, vascular resenosis, pancreatitis, neurodegenerative disease, retinopathy, nephropathy, neuropathy, accelerated gluconeogenesis, excessive (greater than normal levels) hepatic glucose output, and lipid disorders.

Provided herein are also methods of delaying the time to onset or reducing the risk of the development or progression of a disease or condition responsive to decreased hepatic glucose production or responsive to lowered blood glucose levels.

Depending on the condition, disorder, or disease to be treated and the subject's condition, a compound provided herein may be administered by oral, parenteral (e.g., intramuscular, intraperitoneal, intravenous or intraarterial (e.g., via catheter), ICV, intracisternal injection or infusion, subcutaneous injection, or implant), inhalation, nasal, vaginal rectal, sublingual and/or topical (e.g., transdermal or local) routes of administration, and may be formulated alone or together in suitable dosage unit with a pharmaceutically acceptable vehicle, carrier, diluent, excipient, or a mixture thereof, appropriate for each route of administration.

The dose may be in the form of one, two, three, four, five, six, or more sub-doses that are administered at appropriate intervals per day. The dose or sub-doses can be administered in the form of dosage units containing from about from about 0.01 to 2500 mg, from 0.1 mg to about 1,000 mg, from about 1 mg to about 1000 mg, from about 1 mg to about 500 mg, from about 0.1 mg to about 500 mg, from about 0.1 mg to about 100 mg, from about 0.5 mg about to about 100 mg, from about 1 mg to about 100 mg, from about 10 mg to about 1000 mg, from about 10 mg to about 500 mg, or from about 10 mg to about 100 mg of active ingredient(s) per dosage unit. For example, the dose or subdoses can be administered in the form of dosage units containing about 10 mg, about 25 mg, about 50 mg, about 75 mg, about 100 mg, about 250 mg, about 300 mg, about 400 mg, about 500 mg, about 600 mg, about 700 mg, about 800 mg, about 900 mg, or about 1000 mg. If the condition of the patient requires, the dose can, by way of alternative, be administered as a continuous infusion.

In certain embodiments, an appropriate dosage level is about 0.01 to about 100 mg per kg patient body weight per day (mg/kg per day), about 0.01 to about 50 mg/kg per day, about 0.01 to about 25 mg/kg per day, or about 0.05 to about 10 mg/kg per day, which may be administered in single or multiple doses. A suitable dosage level may be about 0.01 to about 100 mg/kg per day, about 0.05 to about 50 mg/kg per day, or about 0.1 to about 10 mg/kg per day. Within this range, the dosage may be about 0.01 to about 0.1, about 0.1 to about 1.0, about 1.0 to about 10, or about 10 to about 50 mg/kg per day.

For oral administration, the pharmaceutical compositions can be provided in the form of tablets containing 1.0 to 1,000 mg of the active ingredient particularly about 1, about 5, about 10, about 15, about 20, about 25, about 50, about 75, about 100, about 150, about 200, about 250, about 300, about 400, about 500, about 600, about 750, about 800, about 900, and about 1,000 mg of the active ingredient for the symptomatic adjustment of the to the patient to be treated. The compositions may be administered on a regimen of 1 to 4 times per day, including once, twice, three times, and four times per day. In various embodiments, the compositions may be administered before a meal, after a meal, in the morning hours, after awakening, in the evening hours, and/or at bedtime.

It will be understood, however, that the specific dose level, frequency, and timing of dosage for any particular patient may be varied and will depend upon a variety of factors including the activity of the specific compound employed, the metabolic stability and length of action of that compound, the age, body weight general health, sex, diet mode and time of administration, rate of excretion, drug combination, the severity of the particular condition, and the host undergoing therapy.

In still another embodiment, provided herein is a method of modulating the biological activity of a glucagon receptor, comprising contacting the receptor with one or more of the compounds provided herein, e.g., a compound of Formulas I or II, including a single enantiomer, a mixture of enantiomers, or a mixture of diastereomers thereof, or a pharmaceutically acceptable salt, solvate, or prodrug thereof, or a pharmaceutical composition thereof. In one embodiment, the glucagon receptor is expressed by a cell.

The compounds provided herein may also be combined or used in combination with other therapeutic agents useful in the treatment, prevention, or amelioration of one or more symptoms of the conditions, disorders, or diseases for which the compounds provided herein are useful. As used herein, the term "in combination" includes the use of more than one therapeutic agents. However, the use of the term "in combination" does not restrict the order in which therapeutic agents are administered to a subject with a condition, disorder, or disorder. A first therapeutic agent (e.g., a therapeutic agent such as a compound provided herein) can be administered prior to (e.g., 5 min, 15 min, 30 min, 45 min, 1 hr, 2 hrs, 4 hrs, 6 hrs, 12 hrs, 24 hrs, 48 hrs, 72 hrs, 96 hrs, 1 wk, 2 wks, 3 wks, 4 wks, 5 wks, 6 wks, 8 wks, or 12 wks before), concomitantly with, or subsequent to (e.g., 5 min. 15 min. 30 min, 45 min. 1 hr, 2 hrs, 4 hrs, 6 hrs, 12 hrs, 24 hrs, 48 hrs, 72 hrs, 96 hrs, 1 wk, 2 wks, 3 wks, 4 wks, 5 wks, 6 wks, 8 wks, or 12 wks after) the administration of a second therapeutic agent to a subject to be treated.

When a compound provided herein is used contemporaneously with one or more therapeutic agents, a pharmaceutical composition containing such other agents in addition to the compound provided herein may be utilized, but is not required. Accordingly, the pharmaceutical compositions provided herein include those that also contain one or more other therapeutic agents, in addition to a compound provided herein.

In one embodiment, the other therapeutic agent is an antidiabetic agent.

Suitable antidiabetic agents include, but are not limited to, insulin sensitizers, biguanides (e.g., buformin, metformin, and phenformin). PPAR agonists (e.g., troglitazone, pioglitazone, and rosiglitazone), insulin and insulin mimetics, somatostatin, $\alpha$-glucosidase inhibitors (e.g., voglibose, miglitol, and acarbose), dipeptidyl peptidase-4 inhibitors, liver X receptor modulators, insulin secretagogues (e.g., acetohexamide, carbutamide, chlorpropamide, glibornuride, gliclazide, glimepiride, glipizide, gliquidone, glisoxepid, glyburide, glyhexamide, glypinamide, phenbutamide, sulfonylureas, tolazamide, tolbutamide, tolcyclamide, nateglinide, and repaglinide), other glucagon receptor antagonists. GLP-1, GLP-1 mimetics (e.g., exenatide, liraglutide, DPPIV inhibitors), GLP-1 receptor agonists, GIP, GIP mimetics, GIP receptor agonists, PACAP, PACAP mimetics, PACAP receptor 3 agonists, cholesterol lowering agents. HMG-CoA reductase inhibitors (e.g., statins, such as lovastatin, simvastatin, pravastatin, fluvastatin, atorvastatin, itavastatin, rivastatin, NK-104 (a.k.a. itavastatin, nisvastatin, and nisbastatin), and ZD-4522 (also known as rosuvastatin, atavastatin, and visastatin)), a cholesterol absorption inhibitor (e.g., ezetimibe), sequestrants, nicotinyl alcohol, nicotinic acid and salts thereof, PPAR $\alpha$ agonists, PPAR $\alpha/\gamma$ dual agonists, inhibitors of cholesterol absorption, acyl CoA:cholesterol acyltransferase inhibitors, anti-oxidants, PPAR $\delta$ agonists, antiobesity compounds, ileal bile acid transporter inhibitors, anti-inflammatory agents, and protein tyrosine phosphatase-1B (PTP-1B) inhibitors.

The dosages given will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

The weight ratio of a compound provided herein to the second active ingredient depends upon the effective dose of each ingredient. Generally, an effective dose of each will be used. Thus, for example, when a compound provided herein is combined with a PPAR agonist the weight ratio of the compound provided herein to the PPAR agonist will generally range from about 1000:1 to about 1:1000 or about 200:1 to about 1:200. Combinations of a compound provided herein and other active ingredients will generally also be within the aforementioned range, but in each case, an effective dose of each active ingredient should be used.

Synthesis of Compounds

Compounds of Formula I and II can be prepared according to the methodology outlined in the following general synthetic schemes or with modifications of these schemes that will be evident to persons skilled in the art, or by other methods readily known to those of skill in the art.

In the following sections, the following abbreviations have the following meanings: THF: Tetrahydrofuran; DME: 1,2-Dimethoxyethane; DMF: N,N-Dimethylformamide; DCC: N, N'-Dicyclohexylcarbodiimide; EDCl or EDC: 1-(3-Dimethylaminopropyl)-3-ethyl carbodiimide hydrochloride; LiHMDS: Lithium hexamethyldisilyl azide; HOBt: I-Hydroxybenzotriazole; EtOAc: Ethyl acetate; EtOH: Ethanol; IPA: iso-Propanol; ACN: Acetonitrile: DIPEA: N,N-Diisopropyl-ethyl amine; and MTBE: Methyl-tert-butyl ether.

a. Synthesis of Various Building Blocks;

The carboxylic acids 3 can be generated using standard methods. As shown in Scheme 1, a carboxylic ester or acid 1 can be alkylated by reaction with a base (such as lithium diisopropylamide or lithium hexamethyldisilylamide) in a suitable solvent (such as THF or DME) followed by reaction with an aralkyl halide to generate intermediates 2. In one embodiment, when Ra is not hydrogen, then the Ra and Rb groups are adequately chosen so that liberation of the carboxylic acid to generate 3 can take place selectively when Ra is H, 2 and 3 represent the same intermediate). For example, if Ra is a methyl or ethyl group, an Rb group can be a benzyl, t-butyl, 2-trimethylsilylethyl group or other groups that can be selectively removed under conditions where the ester group Ra would remain intact such as hydrogenolysis for the benzyl group, mild acid such as trifluoroacetic acid for the t-butyl group or a fluoride source for the 2-trimethylsilylethyl group such as a tetraalkyl ammonium fluoride (e.g. tetrabutyl ammonium fluoride).

Scheme 1

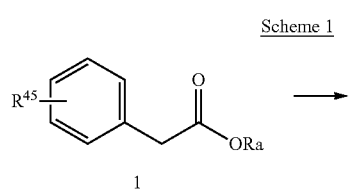

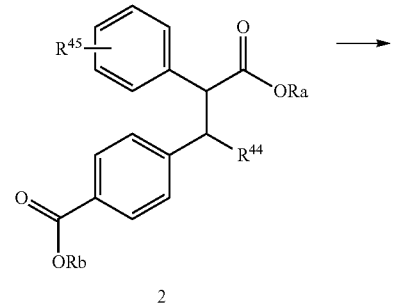

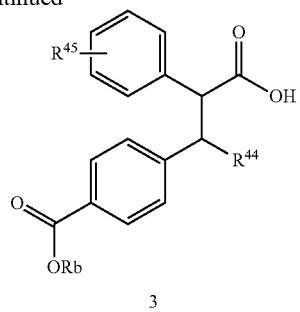

An alternative route for the synthesis of this particular building block, shown in Scheme 2, involves the condensation of an acetic acid derivative 1 with an aldehyde or a ketone leading to the α,β-unsaturated ester intermediate 4. The esters 4 can be hydrogenated under conditions that are well-documented in the literature (for example, hydrogen atmosphere and palladium on carbon as a catalyst in a solvent such as ethanol) to generate the carboxylate esters 3.

Scheme 2

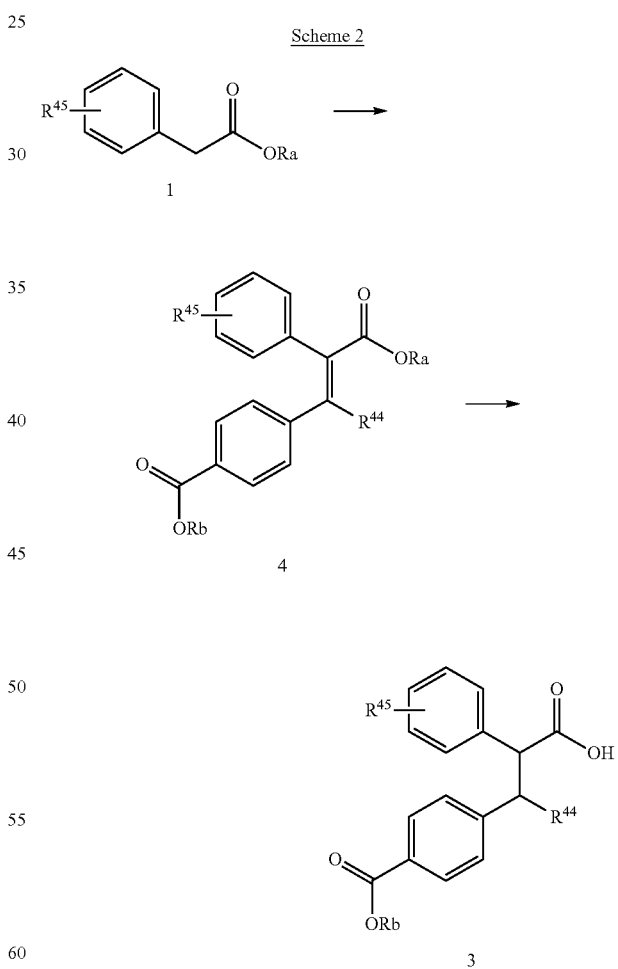

Alternatively, if $R^{44}$ in 4 is H (compound 5), 1,4-addition of an alkyl group can take place by reaction with a suitable carbon nucleophile (e.g. copper mediated reaction of alkyl lithium or alkyl Grignard reagents) to yield compounds 3 where $R^{44}$ is alkyl (Scheme 3).

Scheme 3

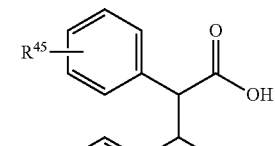

Scheme 4 shows an alternative route to precursors 5, involving the palladium catalyzed reaction of a vinylic halide 7 with an organometallic reagent such as an aryl boronic acid or an aryl stannane. These vinylic halides 7 (where Hal represents bromide or iodide), can be generated from the corresponding benzaldehydes and a halogenated Horner-Emmons reagent $(RO)_2P(O)CH(Hal)CO_2Ra$ (Toke et al. Tetrahedron 51, 9167 (1995); Vanderwal et al. J. Am. Chem. Soc., 125 (18), 5393-5407 (2003)) in the presence of base or by the reaction of the same starting aldehyde with $[Ph_3P=C(IPh)CO_2Ra]^{(+)}[BF_4]^{(-)}$ in dichloromethane in the presence of a halide source such as tetra-n-butyl ammonium bromide or tetra-n-butyl ammonium iodide (Huang et al, J. Org. Chem 67, 8261 (2002))

Scheme 4

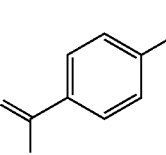

It is recognized that the carbon atom alpha to the central carbonyl group is an asymmetric center. The synthesis of compounds provided herein in enantiomercally pure form can be achieved by utilization of the methods described above if the starting material 8 exists in enantiomerically pure form. An optically pure precursor 8* or 8**, can be generated by resolution of racemic 8 or by use of synthetic methods that generate the asymmetric center in an enantioselective manner.

Resolution methods include the generation of a diastereomeric mixture of carboxylate salts with an optically active amine, which may be separated by fractional crystallization. Acidification of the individual diastereomeric salts and isolation of the carboxylic acid affords the individual enantiomers of the carboxylic acid (D. Kozma: 'CRC Handbook of Optical Resolutions via Diastereomeric Salt Formation' CRC Press, 2001). Alternatively, diastereomeric mixtures of ester or amide derivatives may be prepared by condensation of the racemic carboxylic acid with an optically active alcohol or amine, respectively; these diastereomers may be separated by chromatographic methods and/or fractional crystallization. The pure enantiomers are then generated from the individual diastereomers by reconversion to the carboxylic acid, using methods that are well established in the literature (Scheme 5).

Scheme 5

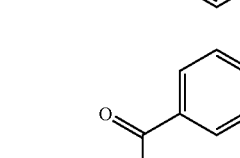

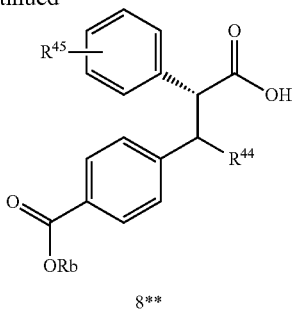

8**

Methods that generate the chiral center in an enantioselective manner include, but are not limited to, the alkylation of precursors containing a chiral auxiliary Xc. This may generate two diastereomers, which may be separated by fractional crystallization or chromatography (Scheme 6). After the separation of the diastereomers, they can be converted into the enantiomerically pure acid 3 and its enantiomer 3* by known procedures and further elaborated into the compounds provided herein as described in the Examples below.

Scheme 6

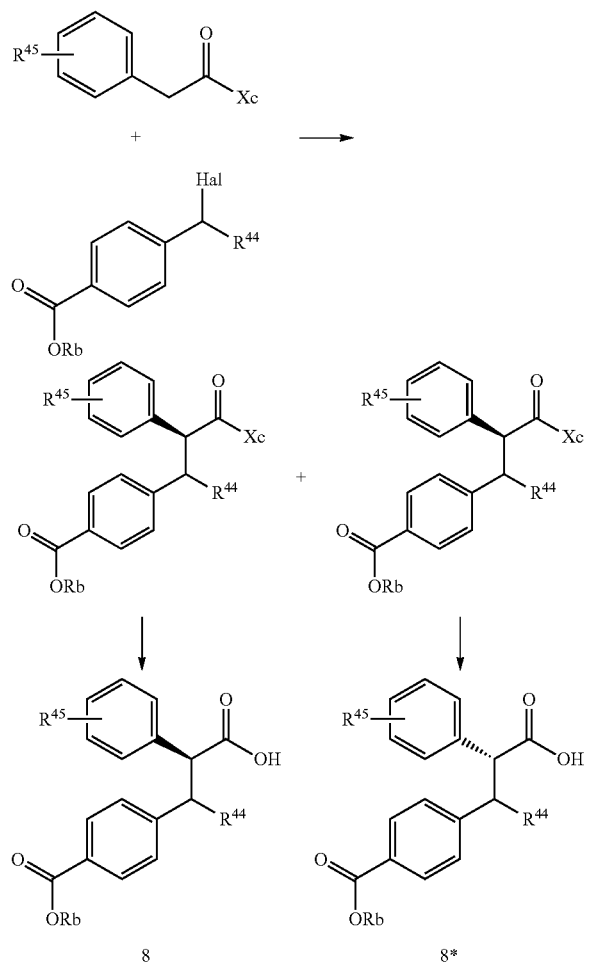

Asymmetric centers may be present in other positions of the molecule. As an example, substitution on a cyclohexenyl group generates a new chiral center in the compound of Example 1. This center can be established in an appropriately functionalized precursor prior to construction of the target molecule. A potential route to this chiral precursor involves the desymmetrization of a racemic ketone as illustrated in Scheme 7. The reaction of 4-t-butylcyclohexanone with a chiral amide base has been reported to generate the corresponding chiral enolate in an enantioselective manner [Busch-Petersen and Corey. Tetrahedron Letters 41, 6941 (2000), Lyapkalo et al. Synlett 1292 (2001)]. Conversion of the enolate into a trifluoromethanesulfonate or a nonafluorobutanesulfonate [Busch-Petersen and Corey, Tetrahedron Letters 41, 6941(2000), Lyapkalo et al. Synlett 1292 (2001)], leads to a chiral precursor that may be used in subsequent steps (A specific enantiomer is shown below, but it should be understood that either enantiomer can be synthesized by modifications of this method). The precursor 9 so obtained can then be elaborated into the single enantiomer as described above.

Scheme 7

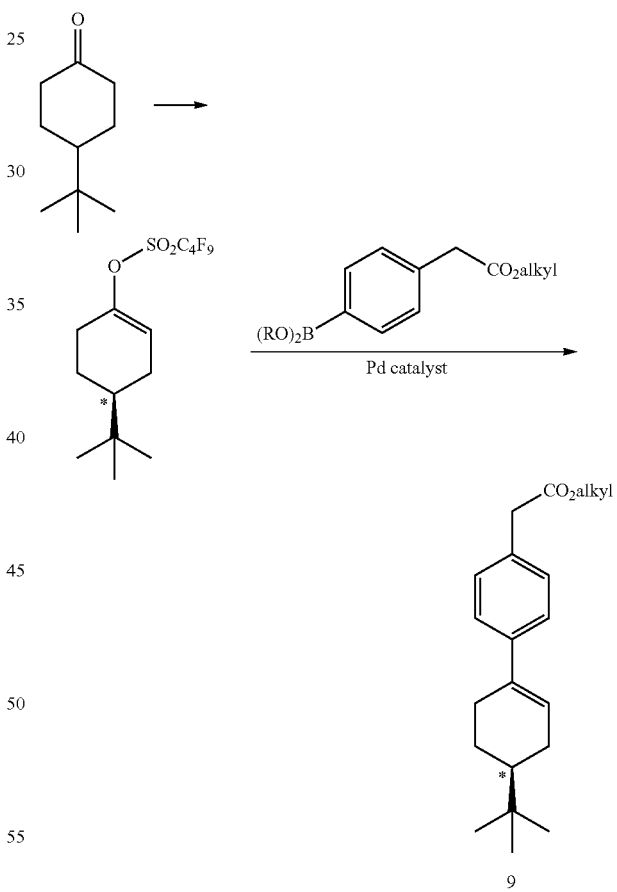

In a related manner, the two enantiomers of a 4-substituted cyclohex-1-enyl system can be obtained through resolution of the corresponding racemic alkene. For example, (enantiospecific or enantioselective) reaction of an alkene 10 (wherein $R^{50}$ and $R^{51}$ are different groups) generates a mixture of diastereomers which upon separation provides 11 and 12. Regeneration of the alkene provides the two enantiomers 13 and 13* (Scheme 8).

Scheme 8

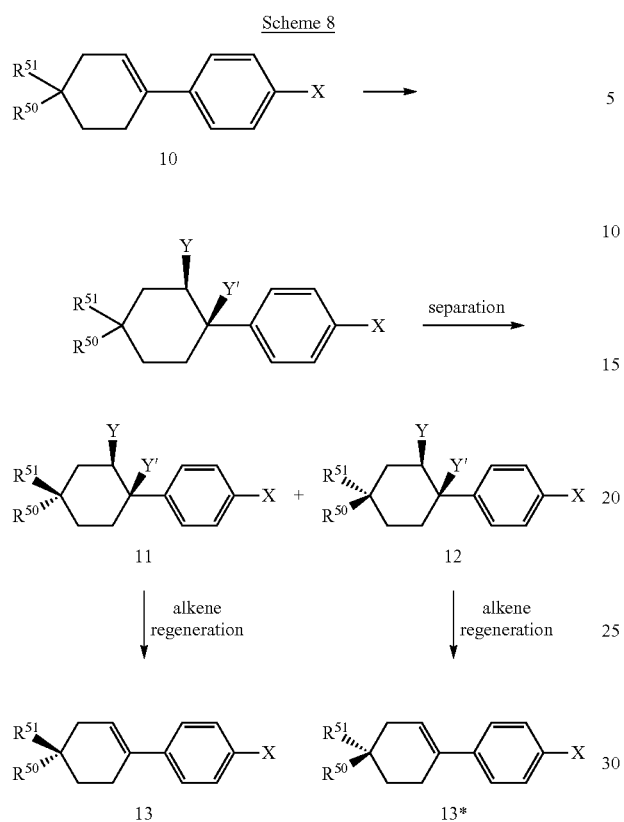

In addition to the methods described above, optically pure compounds can be obtained from their racemic parent compounds through chromatographic methods that utilize a chiral stationary phase.

A method that can be used to synthesize compounds of formula I is exemplified below (Scheme 9). The carboxylic acids 8 are converted to the corresponding amides by methods known for amide bond formation reactions. As an example, generation of an acid chloride 14 from 8 takes place under standard conditions (e.g. thionyl chloride in toluene or oxalyl chloride and catalytic DMF in dichloromethane). Treatment of acid chloride 14 with amines or anilines generates the amides IS. Alternatively, amines can be directly coupled with the carboxylic acid 8 by use of an activating agent (for example, DCC or EDCl with or without a catalyst such as DMAP or HOBT) to directly generate the amides IS. When L is a halo group such as bromo or iodo, aryl amides 15 can be further functionalized through metal-mediated (e.g. Palladium) C—C bond coupling reactions to give further L-functionalized amides 15. Hydrolysis of the ester group of IS (e.g. Rb═—CH$_3$ or —C(CH$_3$)$_3$) results in a carboxylic acid 15 (wherein Rb═H), which can then be coupled with taurine derivatives using standard amide bond forming reactions to generate the targeted compounds 16.

The amide bond in the last step can also be formed by other reported methods known for amide bond formation, for example, reaction of an N-hydroxysuccinimidyl ester of 15 (Rb═O-succinimidyl) and taurine gives the target taurine amide derivative 16. Other activated esters (e.g. pentafluorophenyl esters) can also be used to effect the amide bond formation.

Scheme 9

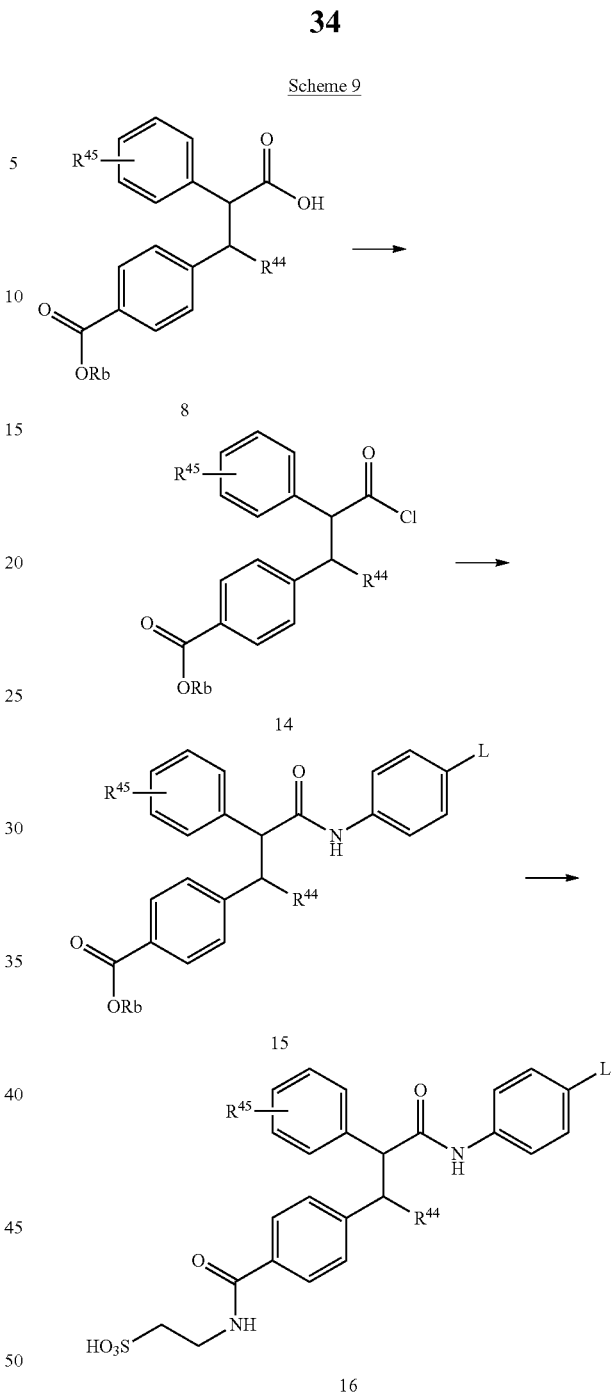

The following examples are provided so that this disclosure can be more fully understood. They should not be construed as limiting the disclosure in any way.

EXAMPLES: BIOLOGICAL EXAMPLES

Example A—Human Glucagon Receptor Affinity

Compounds provided herein are dissolved in a suitable solvent (e.g., dimethylsulfoxide) at a concentration of 10 mM and then diluted in buffer (e.g., 50 mM Hepes, pH 7.4, 5 mM MgCl$_2$, 1 mM CaCl$_2$, and 0.2% BSA) to concentrations ranging from 1 nM to 100 μM. Compounds (20 μL/well) and [$^{125}$I]glucagon at the final concentration of 0.125 nM (20 µl/well) (Perkin Elmer) are added to and mixed in wells of a 96-well plate (Costar, Corning) containing 120 µL of buffer. Next, an appropriate aliquot of a membrane preparation containing the human glucagon receptor (isolated from human liver samples or obtained from a recombinant cell line) is added to the wells. The binding mixtures are incubated for 2 hrs at room temperature. In the meantime, a Multiscreen 96-well filter plate (Millipore) is treated with 200 µL of the buffer, which is vacuumed through the filter just before the binding mixtures are transferred to the plate. At the end of incubation, binding mixtures are transferred to the wells of the Multiscreen 96-well filter plate and filtered through by applying vacuum. The plate is washed once with 200 µL per well of the buffer, and the filters are dried and counted using a gamma counter.

Compounds provided herein have been shown to have high affinity for the glucagon receptor. Examples of some compounds are provided in the Table below. The Table below displays the results of testing the compounds shown in the human glucagon receptor binding assay. Also shown are data from the human hepatocyte assay, oral bioavailability in the rat, and glucose lowering in the db/db mouse (see Examples below for assay descriptions). The column marked "stereo" indicates whether the tested compound tested was racemic or the R-isomer (rac=racemic).

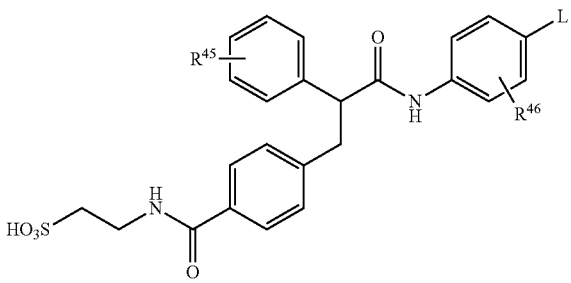

| | | stereo | Hu IC50 (nM) | Hu Hepatocyte EC50 (nM) | OBAV in rat | % Glu lowering in db/db mouse @ 30 mg/kg |
|---|---|---|---|---|---|---|
| 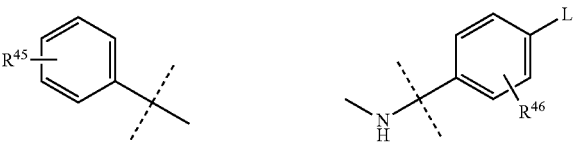 | 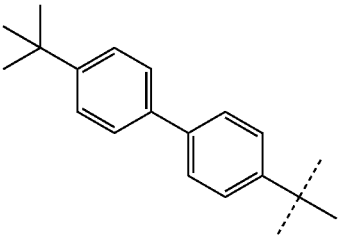 | R | 5 | 4 | 73 | 57 |
| 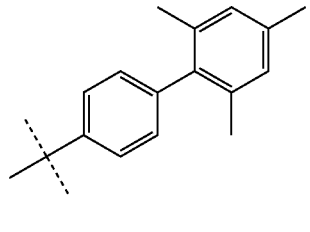 | 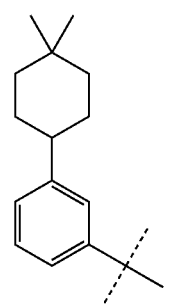 | R | 10 | 12 | 52 | 45 |
| 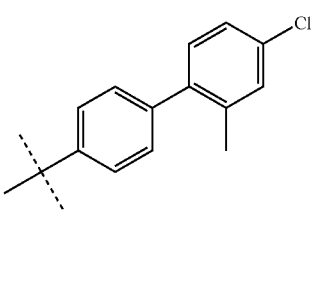 | | R | 9 | 3 | 54 | 53 |

-continued

| | | stereo | Hu IC50 (nM) | Hu Hepatocyte EC50 (nM) | OBAV in rat | % Glu lowering in db/db mouse @ 30 mg/kg |
|---|---|---|---|---|---|---|
| (norbornene-phenyl) | (benzoxazole-phenyl) | rac | 18 | 27 | — | — |
| (4-tert-butyl-biphenyl) | (4-chloro-3-methyl-biphenyl) | R | 6 | 31 | 62 | 33 |
| (4-tert-butyl-biphenyl) | (4,4-dimethylcyclohexenyl-phenyl) | R | 8 | 36 | 69 | 29 |
| (4-tert-butyl-biphenyl) | (2-chloro-biphenyl) | rac | 18 | 412 | — | — |

-continued
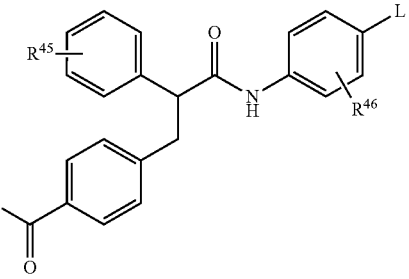
| | | stereo | Hu IC50 (nM) | Hu Hepatocyte EC50 (nM) | OBAV in rat | % Glu lowering in db/db mouse @ 30 mg/kg |
|---|---|---|---|---|---|---|
| 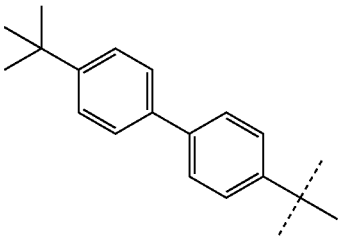 | 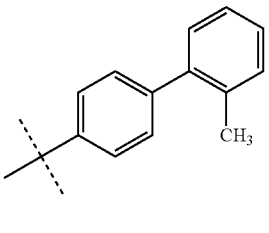 | rac | 10 | 194 | — | 45 |
| 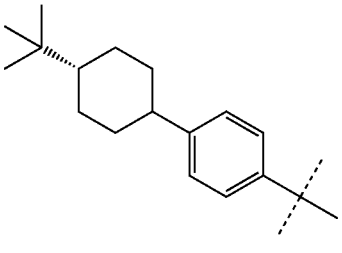 | 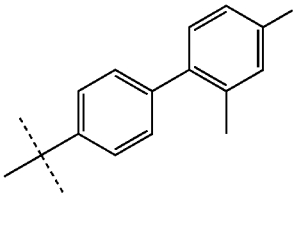 | rac | 12 | 41 | — | 58 |
| 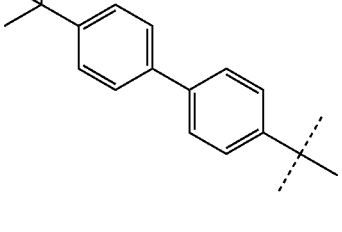 | 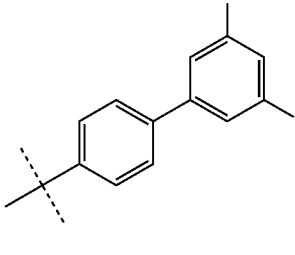 | rac | 15 | 132 | — | — |
| 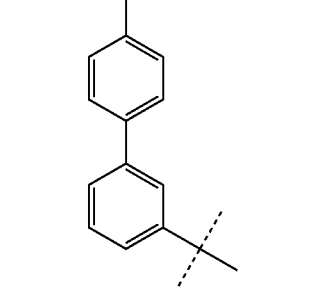 | 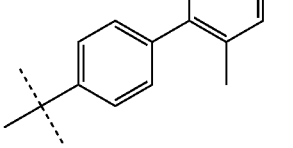 | rac | 15 | 329 | — | — |

| R45 group | NHR46/L group | stereo | Hu IC50 (nM) | Hu Hepatocyte EC50 (nM) | OBAV in rat | % Glu lowering in db/db mouse @ 30 mg/kg |
|---|---|---|---|---|---|---|
| 4-tBu-biphenyl | 5,7-dimethylbenzoxazol-2-yl phenyl | rac | 11 | 560 | — | — |
| 3',5-di-tBu-biphenyl | 2,4-dichlorobiphenyl-4'-yl | rac | 15 | 215 | — | — |
| 4,4-dimethylcyclohexenyl-phenyl | 4-CF3-2-methyl-biphenyl | rac | 11 | 30 | — | 20 |
| 4-tBu-biphenyl | 3,4'-dichloro-2'-methyl-biphenyl | rac | 19 | — | — | — |

US 10,221,130 B2
43 44
-continued
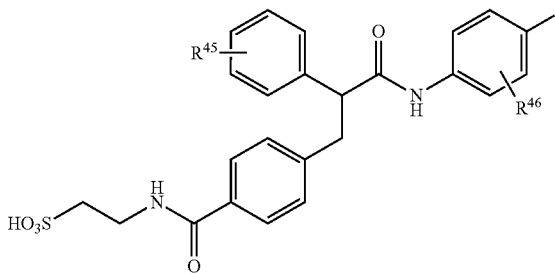
| | | stereo | Hu IC50 (nM) | Hu Hepatocyte EC50 (nM) | OBAV in rat | % Glu lowering in db/db mouse @ 30 mg/kg |
|---|---|---|---|---|---|---|
| 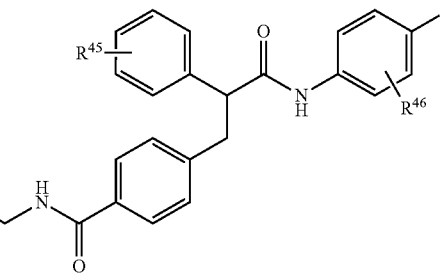 | 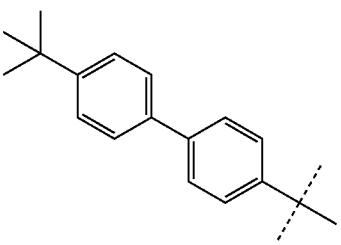 | rac | 18 | 60 | — | — |
| 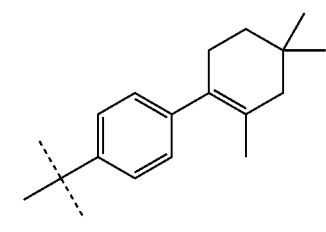 | 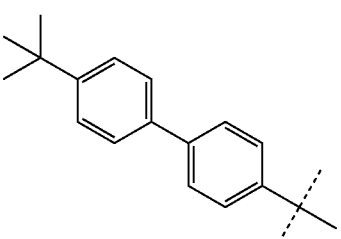 | rac | 12 | 661 | — | — |
| 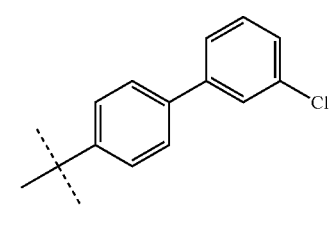 | 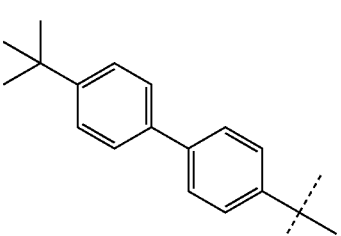 | rac | 10 | — | — | — |
| 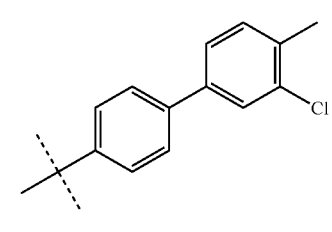 | 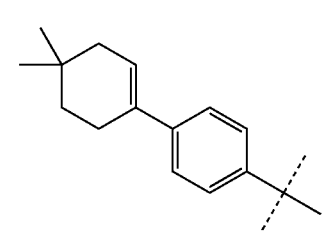 | rac | 16 | — | — | — |

-continued

| R45 group | R46/L group | stereo | Hu IC50 (nM) | Hu Hepatocyte EC50 (nM) | OBAV in rat | % Glu lowering in db/db mouse @ 30 mg/kg |
|---|---|---|---|---|---|---|
| 4-tert-butyl-cyclohexenyl-phenyl | 4-(benzoxazol-2-yl)phenyl | rac | 8 | 116 | — | — |
| 4-tert-butyl-cyclohexyl-phenyl | 4-(benzoxazol-2-yl)phenyl | rac | 18 | 161 | — | — |
| 4-tert-butyl-cyclohexyl-phenyl | 2-Cl-4-CF3-biphenyl | rac | 12 | 30 | — | — |
| 4,4-dimethyl-cyclohexenyl-phenyl | 2-methyl-4-Cl-biphenyl | rac | 17 | 49 | 48 | 42 |
| cyclohexenyl-phenyl | 2-Cl-4-CF3-biphenyl | rac | 16 | — | — | — |

| | | stereo | Hu IC50 (nM) | Hu Hepatocyte EC50 (nM) | OBAV in rat | % Glu lowering in db/db mouse @ 30 mg/kg |
|---|---|---|---|---|---|---|
| 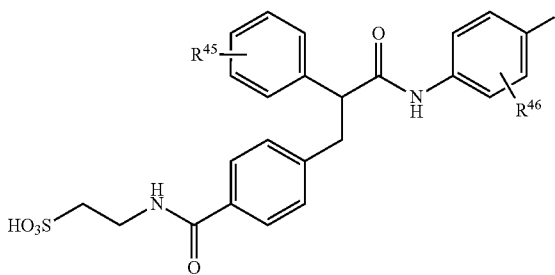 | 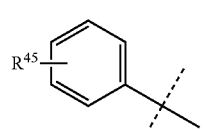 | rac | 16 | 78 | — | — |
| 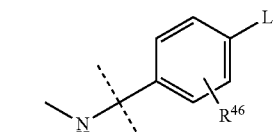 | 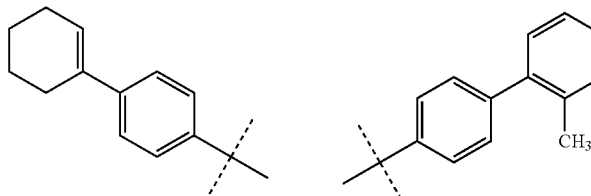 | rac | 15 | 137 | — | — |
| 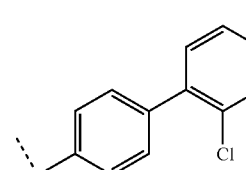 | 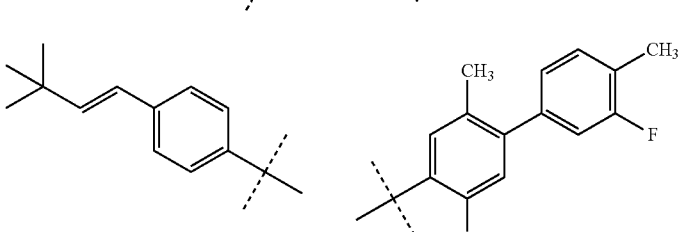 | rac | 20 | 143 | — | — |
| 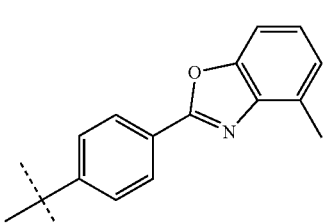 | 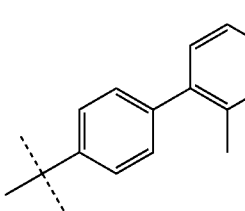 | rac | 13 | 62 | — | 39 |
| | | rac | 9 | 26 | 38 | 56 |

| R⁴⁵ group | R⁴⁶/L group | stereo | Hu IC50 (nM) | Hu Hepatocyte EC50 (nM) | OBAV in rat | % Glu lowering in db/db mouse @ 30 mg/kg |
|---|---|---|---|---|---|---|
| | | rac | 14 | 32 | — | — |
| | | rac | 19 | 108 | — | — |
| | | rac | 15 | 30 | — | 28 |
| | | rac | 18 | 61 | — | — |

-continued

| stereo | Hu IC50 (nM) | Hu Hepatocyte EC50 (nM) | OBAV in rat | % Glu lowering in db/db mouse @ 30 mg/kg |
|---|---|---|---|---|
| rac | 12 | 241 | — | — |
| rac | 8 | 167 | — | — |
| rac | 12 | — | — | — |
| rac | 18 | — | — | — |

-continued
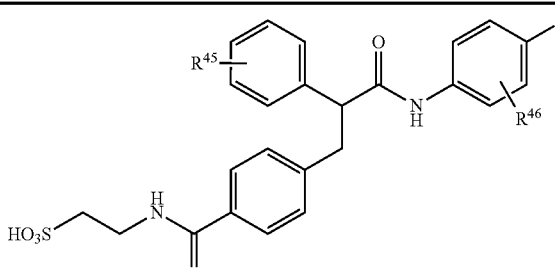
| R⁴⁵ group | R⁴⁶ / L group | stereo | Hu IC50 (nM) | Hu Hepatocyte EC50 (nM) | OBAV in rat | % Glu lowering in db/db mouse @ 30 mg/kg |
|---|---|---|---|---|---|---|
| 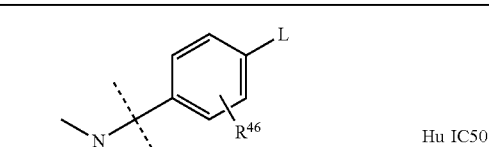 | 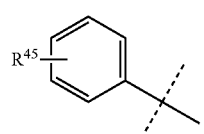 | rac | 16 | — | — | 25 |
| 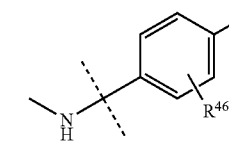 | 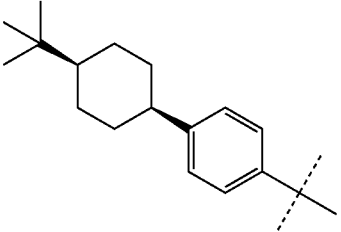 | rac | 12 | — | — | — |
| 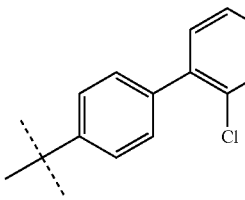 |  | rac | 18 | — | — | — |
|  |  | rac | 10 | — | — | — |
|  |  | rac | 14 | — | — | — |

-continued

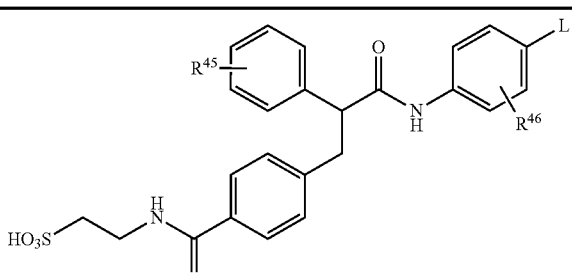

| R⁴⁵ group | R⁴⁶ group | stereo | Hu IC50 (nM) | Hu Hepatocyte EC50 (nM) | OBAV in rat | % Glu lowering in db/db mouse @ 30 mg/kg |
|---|---|---|---|---|---|---|
| 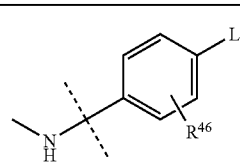 | 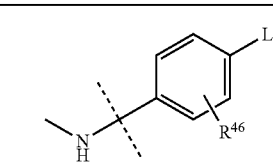 | rac | 10 | 192 | — | — |
| 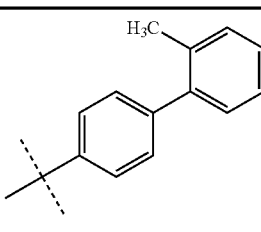 | 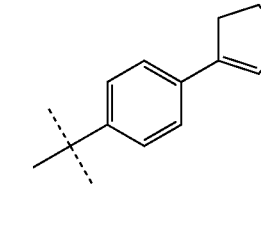 | rac | 17 | 65 | — | 30 |
| 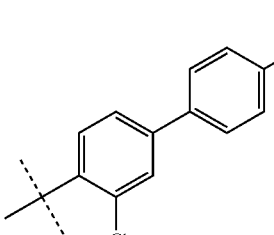 | | rac | 10 | — | — | — |

The compounds of Formula I provided herein which have been tested displace radiolabeled glucagon from the human glucagon receptor with an IC₅₀ of <15 nM.

For certain compounds, the R-enantiomer displays up to 5-fold higher affinity for the human glucagon receptor than the S-enantiomer.

The Table below displays the relative potency in the human glucagon receptor binding assay of the R- vs. S-isomers of the compounds shown. (The stereocenter being changed is marked with an asterisk; the R-isomer is shown in the drawing.)

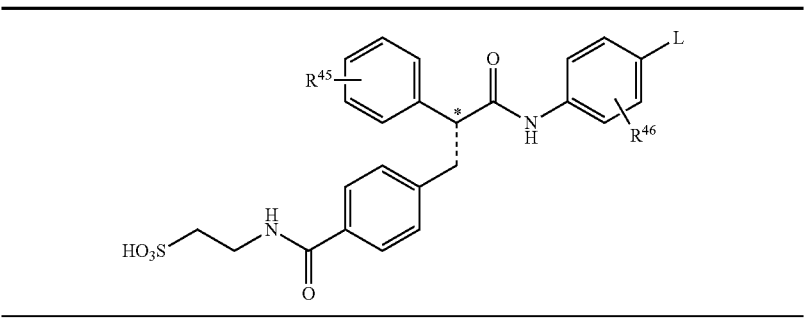
| R45 | NH-R46 with L | Hu IC50 (nM) R | S |
|---|---|---|---|
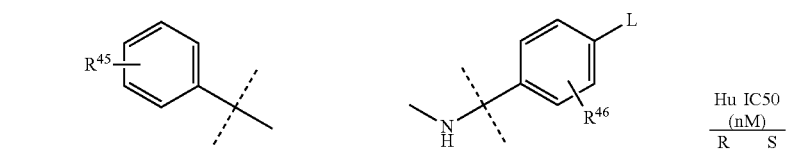 | | 14 | 61 |
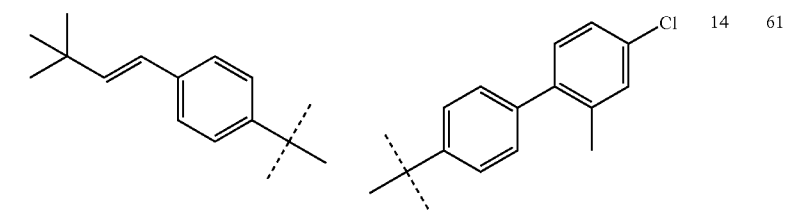 | | 6 | 20 |
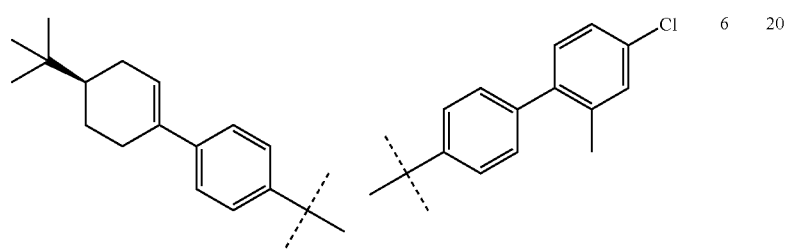 | | 7 | 19 |
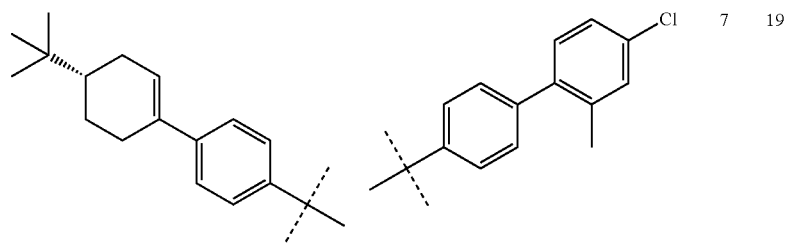 | | 11 | 37 |

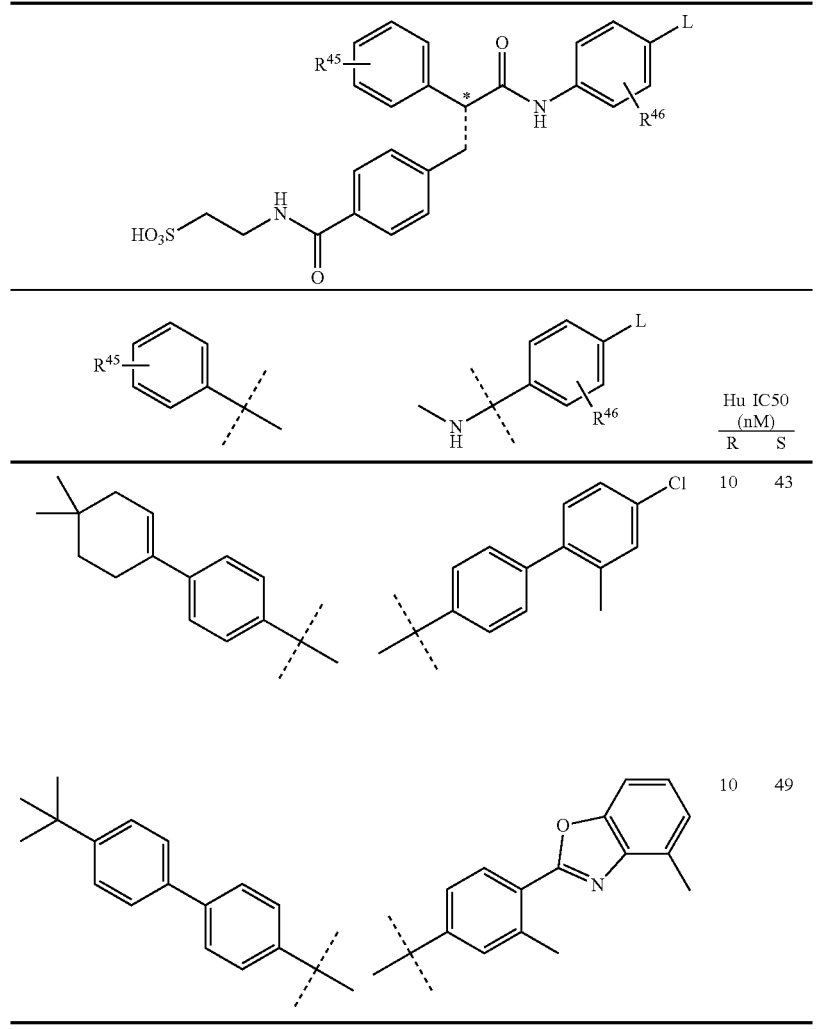

The compounds in the above table display nanomolar affinity for the human glucagon receptor. For certain compounds, the R-enantiomer displays up to 5-fold higher affinity for the human glucagon receptor than the S-enantiomer.

Example B—Functional Antagonism in Hepatocytes from Various Species

Primary human, monkey, dog, rat, or mouse hepatocytes are seeded onto collagen-coated 24-well plates in Williams E medium (supplemented with 10% fetal bovine serum) and incubated at 37° C. overnight in M199 medium (supplemented with 15 mM glucose and 10 nM human insulin). The following day cells are washed twice with a glucose-free Kreb-bicarbonate buffer, pH 7.4, containing 0.1% BSA. Cells are then incubated at 37° C. with the aforementioned buffer containing 1 nM glucagon and varying concentrations of a glucagon antagonist (0~100 microM). Control wells without glucagon or antagonist are also included. After 1 hour, an aliquot of the medium is removed and analyzed for glucose content by means of the glucose oxidase method. The background glucose levels observed in the control wells are subtracted from the glucagon and antagonist containing wells. A graph of % glucose concentration vs drug concentration is plotted and an EC50 value for inhibition of glucose production generated using Sigmaplot software (SAS, Cary, N.C.). Alternatively, intracellular cAMP levels are measured using standard kits and EC50 values determined by plotting these levels against drug concentration. Antagonists of the glucagon receptor inhibit glucagon-induced cAMP production.

The R-enantiomer compounds of Formula I provided herein which have been tested show functional antagonism of glucose production in human hepatocytes with an $EC_{50}$ of <40 nM.

The compounds disclosed herein display significant functional antagonism of glucose production in human hepatocytes. For certain compounds, the R-enantiomer displays up to 50-fold greater functional antagonism in human hepatocytes than the S-enantiomer.

The Table below displays the relative potency in the human hepatocyte functional assay of the R- vs. S-isomers of the compounds shown. (The stereocenter being changed is marked with an asterisk; the R-isomer is shown in the drawing.)

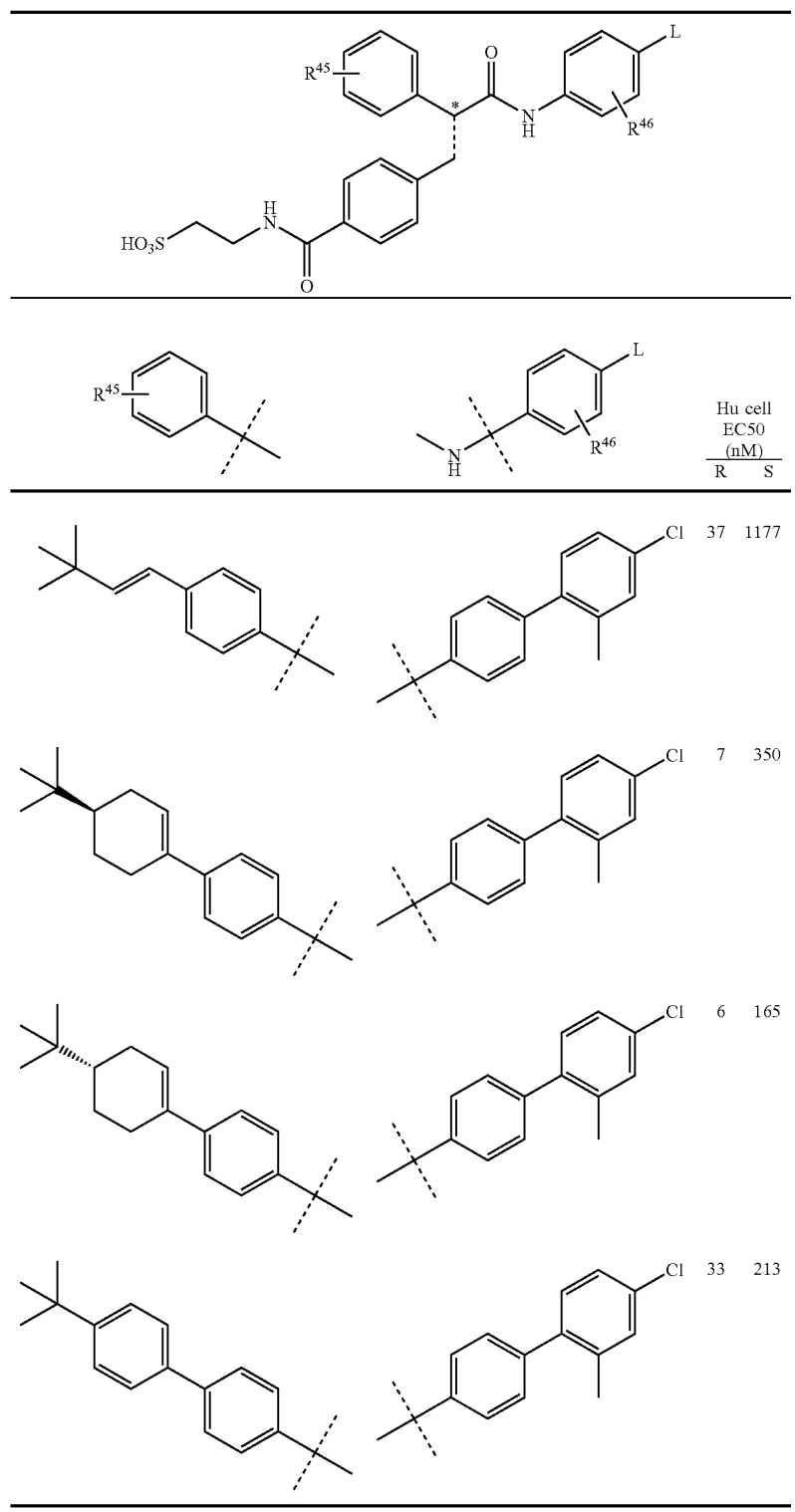

Example C—Glucose Lowering in Diabetic Animals

The effects of compounds provided herein on blood glucose levels are assessed in animal models of type 1 or 2 diabetes such as, but not limited to, the db/db mouse, the Zucker fatty (ZF) rat, the Zucker diabetic (ZDF) rat, the glucagon-challenged dog, the alloxan- or streptozotocin-treated mouse or rat, the NOD mouse or the BB rat.

Compounds are dissolved in an appropriate vehicle such as polyethylene glycol-400 or cyclodextrin and administered to animals at doses of 0.1 to 100 mg/kg either by intraperitoneal injection, intravenous injection, or oral gavage. Animal models used in this evaluation [e.g., the db/db mouse, the ZF rat, the ZDF rat, the glucagon-challenged (0.3-5

μg/kg) dog, the alloxan- or streptozotocin-treated mouse or rat, the NOD mouse, or BB rat] are either freely-feeding or fasted from 3 to 24 hours prior to compound administration. In some instances, animals may be subjected to a glucose tolerance test following compound administration by intravenous or oral administration of up to 2 g/kg of glucose. Blood glucose levels are assessed in blood samples obtained by toil bleed or by sampling an appropriate blood vessel by means of a syringe or catheter. Glucose is measured using a portable glucometer such as the OneTouch or HemoCue meters at regular time intervals for up to 24 hours. The extent of blood glucose lowering elicited by the compounds of Formula I or II is determined by comparison to those in control animals administered only the vehicle. The percentage of blood glucose lowering attained is calculated relative to blood glucose levels in vehicle-treated nondiabetic or non-glucagon-challenged control animals.

Example D—Decose Lowering in db/db Mice

To assess the effects of compounds provided herein on blood glucose levels in the db/db mouse, an animal model of type 2 diabetes, compounds are dissolved in polyethylene glycol-400 and administered by oral gavage to db/db mice in the freely-feeding state at doses of 30 and/or 100 mg/kg. Blood glucose levels are assessed in blood samples obtained by tail bleed at baseline (prior to drug administration) and at regular time intervals over 24 hrs using a portable glucometer such as the OneTouch or HemoCue meters. The magnitude of blood glucose lowering elicited by the compounds provided herein is determined by comparison to those in db/db mice administered only the vehicle. The percentage glucose lowering is calculated by factoring in the blood glucose levels of vehicle-treated lean db/+ (heterozygote) mice, with 100% representing the normalization of blood glucose levels from the hyperglycemic state (vehicle-treated db/db mice) to the normoglycemic state (vehicle-treated db/+ mice).

The compounds disclosed herein which have been tested lowered blood glucose of db/db mice in the freely-feeding state. In particular, the percentage blood glucose lowering achieved ranged from 36 to 57% relative to lean control animals.

The compounds disclosed herein have pronounced antihyperglycemic activity in animal models of type 2 diabetes.

EXAMPLES—CHEMICAL SYNTHETIC EXAMPLES

Example 1: Sodium; 2-{4-[2-[4-(4-tert-butyl-cyclohex-1-enyl)-phenyl]-2-(4'-chloro-2'-methyl-biphenyl-ylcarbamoyl)-ethyl]benzoylamino}-ethanesulfonate Step 1: 4-[2-(4-Bromophenyl)-2-carboxy-ethyl]-benzoic acid methyl ester

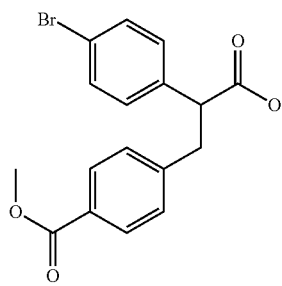 [SMILES: COC(=O)c1ccc(CC(C(=O)O)c2ccc(Br)cc2)cc1]

In a 3-neck flask, a solution of 4-bromophenyl acetic acid (26.91 g) in THF (485 mL) was cooled to <10° C. under a nitrogen atmosphere. A solution of LiHMDS in THF (263 mL, 1.0 M) was added dropwise, ensuring that the internal temperature remained at <10° C. After the addition was complete, the mixture was stirred at 0° C. for about 15 min. The cooling bath was the removed and the reaction mixture was allowed to warm up to 20° C.

The reaction mixture was then cooled to <−60° C. From an addition funnel, a solution of 4-bromomethyl methylbenzoate (29.53 g) in THF (270 mL) was added dropwise, ensuring that the temperature did not rise above −60° C. After the addition was complete, the mixture was stirred at −60° C. for about 15 min, and poured over 300 mL of cold 1M aqueous HCl (saturated with sodium chloride). The organic layer was washed with 1M aqueous HCl (saturated with sodium chloride). The combined aqueous layers were extracted with toluene (50 mL). The combined organic phases were then dried over magnesium sulfate and concentrated under reduced pressure. The crude residue was recrystallized from toluene to yield the carboxylic acid as a white solid. HNMR (300 MHz. DMSO-$d_6$): 12.54 (1H, broad s), 7.82 (2H, d, J=6.4 Hz), 7.49 (2H, d, J=6.7 Hz), 7.32 (2H, d, J=8.2 Hz), 7.26 (2H, d, J=8.5 Hz), 3.95 (1H, t, J=7.9 Hz), 3.81 (3H, s), 3.3 (1H, m, overlaps with residual HOD), 3.03 (1H, m)

Step 2: 4-{2-(4-Bromo-phenylcarbamoyl)-2-[4-(4-tert-butyl-cyclohex-1-enyl)-phenyl]-ethyl}-benzoic acid methyl ester

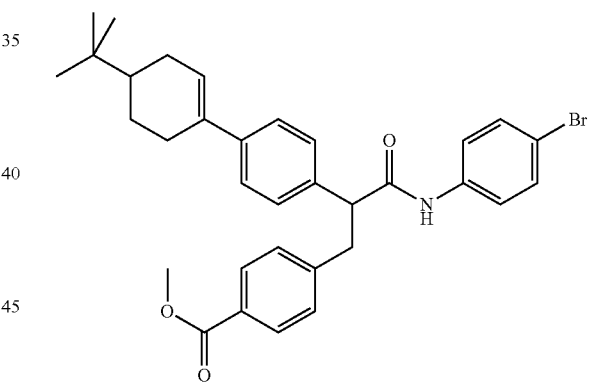

To a solution of 4-[2-(4-Bromophenyl)-2-carboxy-ethyl]-benzoic acid methyl ester (step 1 above, 0.6 g) in THF: ethanol:water (6 mL:3 mL:1.5 mL) added 4-t-butyl-1-cyclohexenyl-boronic acid (0.5 g). $PdCl_2(P(o-tolyl)_3)_2$, and sodium carbonate (0.7 g). The resulting mixture was heated at 125° C. for a 1 h period. The reaction was then cooled to room temperature, treated with an excess of aqueous HCl (1M) and the resulting heterogeneous mixture was filtered through a celite pad. The organic phase was dried over sodium sulfate and concentrated under reduced pressure. The crude residue was dissolved in toluene (25 mL), treated with thionyl chloride (0.26 mL) and heated at 100° C. for a 1 h period. The toluene was removed under reduced pressure. The resulting acid chloride was redissolved in toluene (15 mL), treated with 4-bromoaniline (0.3 g) and diisopropyl ethyl amine (0.3 mL), and heated at 100° C. for a 1 h period. After cooling to room temperature, the mixture was partitioned between ethyl acetate and 1M aqueous HCl. The organic layer was washed (water, saturated sodium chloride), dried over magnesium sulfate and concentrated under reduced pressure. The product obtained was carried to the next step without further purification.

Step 3: Sodium; 2-(4-{2-(4-bromo-phenylcarbamoyl)-2-[4-(4-tert-butyl-cyclohex-1-enyl)-phenyl]-ethyl}-benzoylamino)-ethanesulfonate

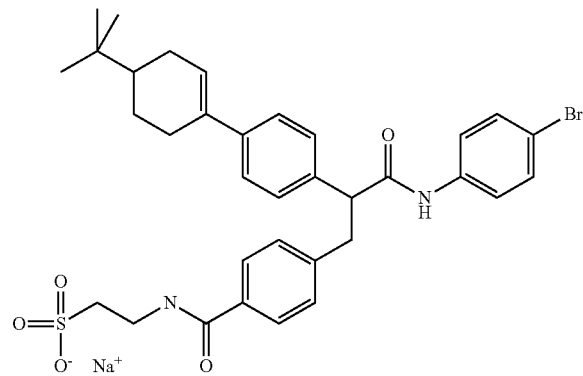 [SMILES: CC(C)(C)C1CC=C(c2ccc(C(Cc3ccc(C(=O)NCCS(=O)(=O)[O-])cc3)C(=O)Nc3ccc(Br)cc3)cc2)CC1 ; [Na+]]

A solution of 4-{2-(4-Bromo-phenylcarbamoyl)-2-[4-(4-tert-butyl-cyclohex-1-enyl)-phenyl]-ethyl}-benzoic acid methyl ester (Step 2, 0.8 g) in THF:methanol:water (8 mL:6 mL:2 mL) was treated with lithium hydroxide (0.4 g) and stirred at room temperature for 16 h. Added an excess of aqueous HCl (1M) and extracted with ethyl acetate. The organic phase was washed with saturated sodium chloride in water and dried over sodium sulfate. The solvents were then removed under reduced pressure. The residue obtained was dissolved in DMF (10 mL), and treated with EDCl (0.4 g). HOBt-H$_2$O (0.32 g), taurine (0.26 g) and diisopropyl ethyl amine (0.71 mL). The reaction mixture was then stirred at room temperature for a 16 h period. The solvent was removed under reduced pressure. The residue was partitioned between ethyl acetate and 1M aqueous HCl. The organic phase was washed with saturated sodium chloride, and concentrated. The residue in methanol was treated with an excess of sodium hydroxide and loaded on top of a C-18 reverse phase flash chromatography column. The column was eluted with an acetonitrile—water gradient to afford the sodium salt of the sulfonate as a white solid. LCMS m/z: 665.6 [C$_{34}$H$_{38}$N$_2$O$_5$BrS]$^-$ Step 4

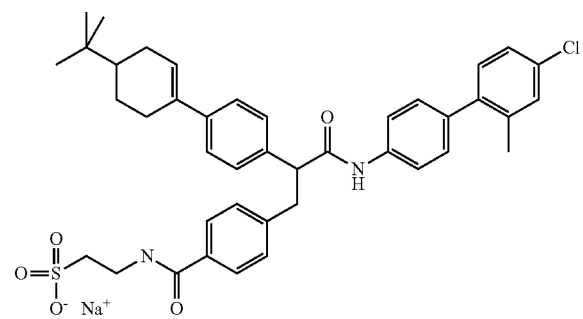 [SMILES: Cc1cc(Cl)ccc1-c1ccc(NC(=O)C(Cc2ccc(C(=O)NCCS(=O)(=O)[O-])cc2)c2ccc(C3=CCC(C(C)(C)C)CC3)cc2)cc1 ; [Na+]]

To a solution sodium; 2-(4-{2-(4-bromo-phenylcarbamoyl)-2-[4-(4-tert-butyl-cyclohex-1-enyl)-phenyl]-ethyl}-benzoylamino)-ethanesulfonate (Step 3 above, 96 mg) in DME:ethanol:water (2 mL:1 mL:0.5 mL) added 4-t-butyl-1-cyclohexenyl-boronic acid (0.5 g), PdCl$_2$(P(o-tolyl)$_3$))$_2$, and sodium carbonate (0.7 g). The resulting mixture was heated at 125° C. for a 1 h period. The reaction was then cooled to room temperature, treated with an excess of aqueous HCl (1M) and the resulting heterogeneous mixture was filtered through a celite pad. The mixture was partitioned (ethyl acetate/water). The organic phase was washed with saturated sodium chloride, and concentrated. The residue in methanol was treated with an excess of sodium hydroxide and loaded on top of a C-18 reverse phase flash chromatography column. The column was eluted with an acetonitrile—water gradient to afford the sodium salt of the sulfonate as a white solid. LC-MS m/z=711.6 [C$_{44}$H$_{44}$N$_2$O$_5$ClS]$^-$ Example 2: Sodium-2-(4-{2-(4'-chloro-2'-methyl biphenyl-4-ylcarbamoyl)-2-[3-(4,4-dimethyl-cyclohexyl)-phenyl]-ethyl}-benzoylamino-ethane sulfonic acid Step 1: 4-Benzyl-3-[2-(3-bromo-phenyl)-acetyl]-oxozolidin-2-one

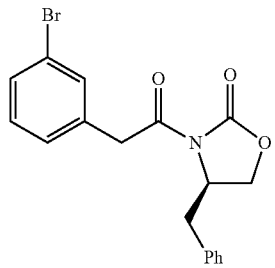 [SMILES: O=C(Cc1cccc(Br)c1)N1C(=O)OC[C@H]1Cc1ccccc1]

To a solution of (3-bromo-phenyl)-acetic acid (5.0 g, 23.2 mmol) in CH$_2$Cl$_2$ (50 mL) at room temperature was added oxalyl chloride (5.86 g, 46.5 mmol). The reaction mixture was stirred at room temperature for overnight and the solvent was removed under reduced pressure. The residue was dried under vacuum for 3-4 h and used without further purification.

In a separate flask, to a stirred solution of R-(+)-4-benzyl-oxazolidinone (4.34 g, 24.5 mmol) in THF (30 mL) at −78° C. was added n-BuLi (26.7 mL, 26.7 mmol, 1.0 M solution in hexane). The reaction mixture was stirred for 1 h, at −78° C. then the crude acid chloride (5.2 g, 22.3 mmol) in THF was added dropwise. The mixture was stirred for 2 h at −78° C. and allowed to warm to rt and stirred for another hour (monitored by TLC). The reaction was quenched with saturated NH$_4$Cl solution (100 mL) and stirred for 10 min. The reaction mixture was extracted with ethyl acetate (2×250 mL) and the combined organic layers were washed with brine, dried over MgSO$_4$ and concentrated under reduced pressure. The crude product was purified by column chromatography on silica gel, eluting with EtOAc-hexanes (5-25%) to afford 4-benzyl-3-[2-(3-bromo-phenyl)-acetyl]-oxozolidin-2-one. $^1$H NMR (300 MHz, CDCl$_3$): 7.51 (d, J=2.1 Hz, 1H), 7.44 (dd, J=3.9, 4.8 Hz, 1H), 7.32-7.20 (m, 6H), 7.15 (d, J=3.9 Hz, 1H), 4.60 (m, 1H), 4.30 (m, 2H), 4.26-4.19 (m, 3H), 3.27 (dd, J=1.8, 8.1 Hz, 1H), 2.78 (dd, J=5.4, 7.8 Hz, 1H); TLC conditions: Uniplate silica gel, 250 microns; mobile phase=ethyl acetate/hexanes (5:1); $R_f$=0.6.

Step 2: 4-{3-(4-Benzyl-2-oxo-oxazolidin-3-yl)-2-[4-(3-bromophenyl)-3-oxo-propyl}-benzoic acid tert-butyl ester

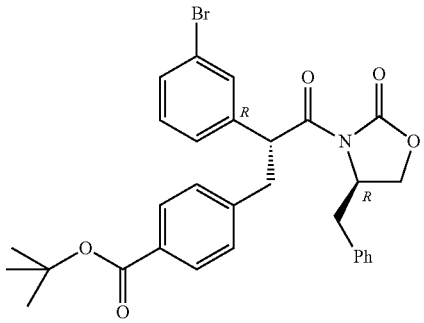

To a stirred solution of 4-benzyl-3-[2-(3-bromo-phenyl)-acetyl]-oxozolidin-2-one (4.02 g, 10.7 mmol) in anhydrous THF (50 mL) was added LiHMDS (16.5 mL 16.5 mmol, 1.0 M solution in THF) at −78° C. The reaction mixture was stirred for 1.5 h at −78° C., and then tert-butyl-4-bromo methyl benzoate (3.75 g, 11.8 mmol, in THF 10 mL) was added dropwise, stirred for 2 h at −78° C. and then allowed to warm to rt for 1 h. After completion of the reaction quenched with saturated NH₄Cl solution (100 mL) and stirred for 10 min. The reaction mixture was extracted with ethyl acetate (2×250 mL) and the organic layer was washed with brine, dried over Na₂SO₄ and concentrated under reduced pressure. The crude product was precipitated from minimum amount of EtOAc and hexane at room temperature to afford 4-{3-(4-Benzyl-2-oxo-oxazolidin-3-yl)-2-[4-(3-bromophenyl)-3-oxo-propyl}-benzoic acid tert-butyl ester as a yellow solid $^1$H NMR (300 MHz, CDCl₃): δ 7.75 (d, J=6.3 Hz, 2H), 7.44 (d, J=2.1 Hz, 2H), 7.26-7.04 (m, 9H), 6.79 (dd, J=1.8, 5.7 Hz, 2H), 5.29 (dd, J=2.1, 6.3 Hz, 1H), 3.89 (s, 3H), 3.83 (d, J=7.5 Hz, 1H), 3.41 (dd, J=8.4, 13.8 Hz, 1H), 3.05 (dd, J=7.2, 13.5 Hz, 1H); TLC conditions: Uniplate silica gel, 250 microns; mobile phase=ethyl acetate-hexanes (1:4); $R_f$=0.45.

Step 3: 4-[2-carboxy-2-(3-bromo-phenyl)-ethyl]-benzoic acid tert-butyl ester (5)

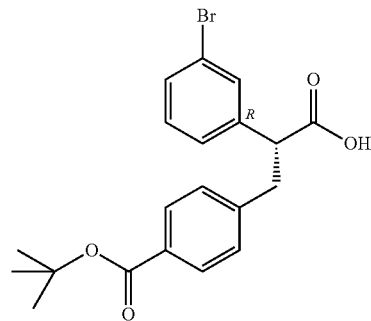

To a stirred solution of 4-{3-(4-benzyl-2-oxo-oxazolidin-3-yl)-2-[4-(3-bromophenyl)-3-oxo-propyl}-benzoic acid tert-butyl ester (2.3 g, 3.7 mmol) in THF/H₂O (20 mL) (3:1) at room temperature were added H₂O₂ (1.25 g, 37.0 mmol 35% in H₂O) followed by LiOH (0.62 g, 14.8 mmol). The reaction mixture was stirred for 3 h, at room temperature and quenched with 0.1 N HCl. The reaction mixture was extracted with ethyl acetate (100 mL) and dried over MgSO₄ filtered and concentrated under reduced pressure to afford the crude acid. This crude product was purified by column chromatography on silica gel, eluting with CH₂Cl₂/MeOH 2%-15% to afford 4-[2-carboxy-2-(3-bromo-phenyl)-ethyl]-benzoic acid tert-butyl ester (1.5 g, 75%). $^1$H NMR (300 MHz, DMSO-d₆): δ 12.52 (s, 1H), 7.77 (d, J=8.4 Hz, 2H), 7.48 (d, J=8.7 Hz, 2H), 7.28 (d, J=8.4 Hz, 2H), 7.22 (d, J=8.4 Hz, 2H), 3.93 (t, J=7.8 Hz, 1H), 3.30 (dd, J=8.4, 13.8 Hz, 1H), 3.0 (dd, J=8.1, 13.8 Hz, 1H), 1.49 (s, 9H). TLC conditions: Uniplate silica gel, 250 microns; mobile phase=CH₂Cl₂/MeOH (10%); $R_f$=0.4. Chiral HPLC conditions: Kromasil 100-5-TBB chiral column 250×4.6 cm, (5% hexane/2-propanol to 30%), 35 min, flow rate 1 mL/min, RT=12.41 min (enantiomeric excess: >96%)

Step 4: 4'-Chloro-2'-methyl-biphenyl-4-amine

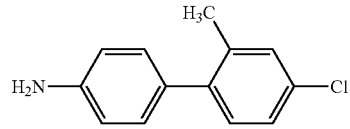

A mixture of 4-iodo-aniline (25.0 g, 114.1 mmol), 2-methyl-4-chlorophenyl-boronic acid (29.17 g, 171.1 mmol), PdCl₂(P(o-tolyl)₃)₂ (11.66 g, 14.8 mmol), and Na₂CO₃ (60.49 g, 570.7 mmol) in DME/EtOH/H₂O (100/50/25 mL) was heated 125° C. for 2 h. The reaction mixture was cooled to room temperature, filtered and washed with EtOAc (200 mL). The solvent was removed under reduced pressure. The crude mixture was extracted with ethyl acetate (500 mL) and the organic layer was washed with brine, dried over Na₂SO₄ and concentrated under reduced pressure. The resulting crude was purified by column chromatography on silica gel, eluting with 5-30% Hexane/EtOAc to afford 4'-Chloro-2'-methyl biphenyl-4-ylamine. $^1$H NMR (300 MHz, CDCl₃): δ 7.24-7.08 (m, 5H), 6.72 (d, J=7.2 Hz, 2H), 3.70 (bs, 2H), 2.27 (s, 3H).

Step 5: 4-[2-(3-Bromo-phenyl)-2-(4'-chloro-2'-methyl-biphenyl-4-ylcarbamoyl)-ethyl]-benzoic acid tert-butyl ester

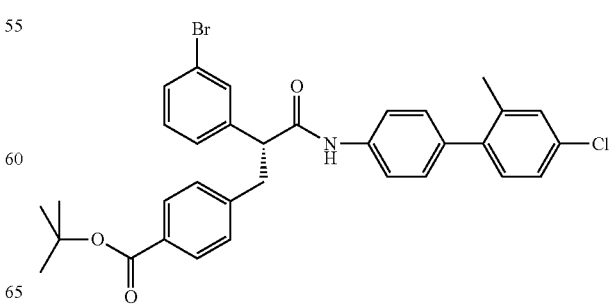

To a stirred suspension of 4-[2-carboxy-2-(3-bromo-phenyl)-ethyl]-benzoic acid tert-butyl ester (2.41 g, 5.94 mmol) in anhydrous CH$_2$Cl$_2$ (20 mL), was added oxalylchloride (1.0 mL, 11.8 mmol) at room temperature The reaction mixture was stirred for 14 h, concentrated under reduced pressure and azeotroped with CH$_2$Cl$_2$ (2×10 mL). The crude acid chloride (2.2 g, 1.61 mmol) was treated with 4-chloro-2-methyl biphenyl-4-ylamine (1.24 g, 5.71 mmol) and N,N-diisopropylethylamine (2.53 mL, 15.5 mmol) in CH$_2$Cl$_2$ (25 mL) at 0° C. The reaction mixture was stirred for 14 h at room temperature and concentrated under reduced pressure. The crude product was purified by column chromatography on silica gel, eluting with CH$_2$Cl$_2$-hexanes (30%-100%) to give 4-[2-(3-bromo-phenyl)-2-(4'-chloro-2'-methyl-biphenyl-4-ylcarbamoyl)-ethyl]-benzoic acid tert-butyl ester as a brownish solid (2.4 g, 88%). $^1$H NMR (500 MHz, CDCl$_3$): δ 7.74 (d, J=14.0 Hz, 2H), 7.58-7.49 (m, 4H), 7.39-7.22 (m, 4H), 7.24-7.19 (m, 3H), 7.14 (d, J=14.0 Hz, 2H), 4.03 (t, J=11.0 Hz, 1H), 3.42 (dd, J=15.5, 22.5 Hz, 1H), 3.03 (dd, J=11.0, 22.5 Hz, 1H), 2.17 (s, 3H), 1.49 (s, 9H): Chiral HPLC conditions: Chiralcel OD-H T=23° C.; mobile phase=5-25% hexane/IPA; flow rate=1.0 mL/min; detection=254, 280, 220 nm retention time in min: 16.66 min (enantiomeric excess: 97.3%).

Step 6: 4-{2'-chloro-2'-methyl-biphenyl-4-ylcarbamoyl)-2-[(3-(4,4-dimethyl-cyclohex-1-enyl)-phenyl]-ethyl}-benzoic acid tert-butyl ester

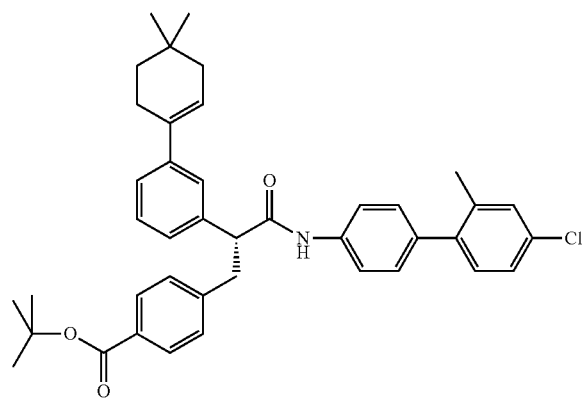 [SMILES: Cc1cc(Cl)ccc1-c1ccc(NC(=O)[C@H](Cc2ccc(C(=O)OC(C)(C)C)cc2)c2cccc(C3=CCC(C)(C)CC3)c2)cc1]

To 4-[2-(3-bromo-phenyl)-2-(4'-chloro-2'-methyl-biphenyl-4-ylcarbamoyl)-ethyl]-benzoic acid tert-butyl ester (1.2 g, 1.98 mmol) in DME (30 mL), was added 4,4-dimethyl-cyclo-hex-1-enyl-boronic acid (0.76 g, 4.96 mmol), PdCl$_2$(P(o-tolyl$_3$)$_2$ (202 mg, 0.25 mmol), and diisopropylethylamine (1.0 mL, 5.94 mmol). The resulting mixture was heated at 85° C. for 2 h, allowed to cool to room temperature and filtered. Partitioned the filtrate between EtOAc (20 mL) and water. The organic phase was washed with brine, dried over sodium sulfate and concentrated under reduced pressure. The resulting crude was purified by column chromatography on silica gel, eluting with CH$_2$Cl$_2$:hexanes (20%-100%) to afford 4-{4'-chloro-2'-methyl-biphenyl-4-ylcarbamoyl)-2-[(3-(4,4-dimethyl-cyclohex-1-enyl)-phenyl]-ethyl}-benzoic acid tert-butyl ester as a yellow solid. $^1$H NMR (500 MHz, CDCl$_3$): δ 10.14 (s, 1H), 7.76 (d, J=8.5 Hz, 2H), 7.57 (d, J=8.4 Hz, 2H), 7.48 (s, 1H), 7.35-7.20 (m, 9H), 7.13 (d, J=8.5 Hz, 1H), 6.06 (bt, 1H), 4.03 (t, J=6.5 Hz, 1H), 3.48 (dd, J=4.5, 13.5 Hz, 1H), 3.04 (dd, J=6.5, 14.0 Hz, 1H), 2.37-2.34 (m, 2H), 2.23 (t, J=7.0 Hz, 1H), 2.18 (s, 3H), 1.57 (t, J=6.5 Hz, 2H), 1.50 (s, 9H), 1.47 (t, J=6.5 Hz, 1H), 0.93 (s, 6H).

Step 7: 4-{2'-chloro-2'-methyl-biphenyl-4-ylcarbamoyl)-2-[(3-(4,4-dimethyl-cyclohex-1-enyl)-phenyl]-ethyl}-benzoic acid

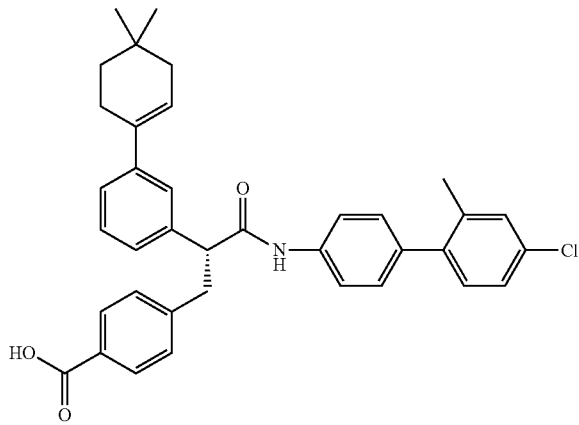 [SMILES: Cc1cc(Cl)ccc1-c1ccc(NC(=O)[C@H](Cc2ccc(C(=O)O)cc2)c2cccc(C3=CCC(C)(C)CC3)c2)cc1]

To a stirred solution of 4-{4'-chloro-2'-methyl-biphenyl-4-ylcarbamoyl)-2-[(3-(4,4-dimethyl-cyclohex-1-enyl)-phenyl]-ethyl}-benzoic acid ten-butyl ester (0.82 g, 1.29 mmol) in CH$_2$Cl$_2$ (30 mL) at room temperature, added trifluoroacetic acid (2.5 ml), and conc HCl (1.0 mL) The reaction mixture was stirred overnight. The organic solvents were removed under reduced pressure. The residue was extracted with ethyl acetate (2×100 mL), dried over MgSO$_4$ and concentrated o afford 4-{2'-chloro-2'-methyl-biphenyl-4-ylcarbamoyl)-2-[(3-(4,4-dimethyl-cyclohex-1-enyl)-phenyl]-ethyl}-benzoic acid as a solid. $^1$H NMR (500 MHz, DMSO-d$_6$): 10.05 (s, 1H), 7.73 (d, J=8.0 Hz, 2H), 7.48 (d, J=8.5 Hz, 2H), 7.40 (s, 1H), 7.29-7.05 (m, 10H), 5.99 (s, 1H), 3.96 (t, J=10.5 Hz, 1H), 2.95 (dd, J=5.0, 14.0 Hz, 1H), 2.20-2.18 (m, 1H), 2.14 (t, J=7.5 Hz, 1H), 2.09 (s, 3H), 1.89 (bs, 2H), 1.49 (t, J=7.5 Hz, 1H), 1.39 (t, J=6.0 Hz, 2H), 0.84 (s, 6H). Chiral HPLC conditions: Chiralcel OD-H T=23° C.; mobile phase=10-30% hexane/IPA; flow rate=1.0 mL/min; detection=254, 280, 220 nm retention time in min: 19.81 min (enantiomeric excess: 70.8%)

Step 8: 4-{2'-chloro-2'-methyl-biphenyl-4-ylcarbamoyl)-2-[(3-(4,4-dimethyl-cyclohexyl)-phenyl]-ethyl}-benzoic acid

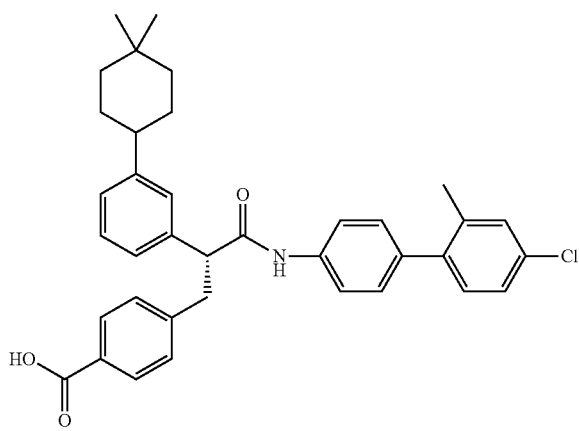 [SMILES: Cc1cc(Cl)ccc1-c1ccc(NC(=O)[C@H](Cc2ccc(C(=O)O)cc2)c2cccc(C3CCC(C)(C)CC3)c2)cc1]

A stirred solution of 4-{4'-chloro-2'-methyl-biphenyl-4-ylcarbamoyl)-2-[(3-(4,4-dimethyl-cyclohex-1-enyl)-phenyl]-ethyl}-benzoic acid (0.62 g, 1.07 mmol) in ethyl acetate (30 mL) at room temperature, was added Pd/C (100 mg). The mixture was stirred under 1 atm of $H_2$ (gas) at room temperature for 4 h. The catalyst was removed by filtration through a Celite plug and washed with ethyl acetate (2×50 mL). Concentration of the filtrate afforded 4-{2'-chloro-2'-methyl-biphenyl-4-ylcarbamoyl)-2-[(3-(4,4-dimethyl-cyclohex-1-enyl)-phenyl]-ethyl}-benzoic acid as a solid. 1H NMR (300 MHz. DMSO-$d_6$): 12.69 (s, 1H), 10.06 (s, 1H), 7.72 (d, J=7.0 Hz, 2H), 7.49 (d, J=7.0 Hz, 2H), 7.27-7.03 (m, 11H), 3.94 (t, J=5.5 Hz, 1H), 3.39 (t, J=11.5 Hz, 1H), 2.93 (dd, J=5.5, 13.0 Hz, 1H), 2.16 (t, J=7.0 Hz, 1H), 2.09 (s, 3H), 1.48-1.43 (m, 4H), 1.24-1.19 (m, 2H), 0.87 (s, 3H), 0.84 (s, 3H).

Step 9: Sodium-2-(4-{2-(4'-chloro-2'-methyl biphenyl-4-ylcarbamoyl)-2-[3-(4,4-dimethyl-cyclohexyl)-phenyl]-ethyl}-benzoylamino-ethane sulfonic acid

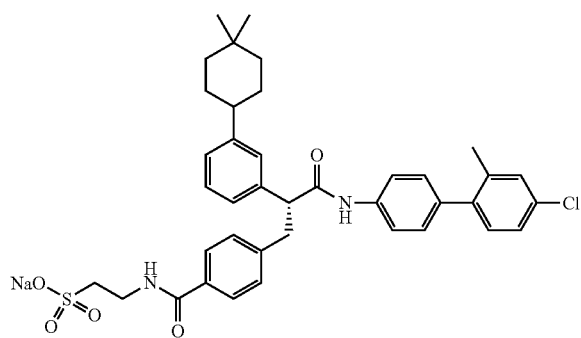

To a mixture of 4-{2'-chloro-2'-methyl-biphenyl-4-ylcarbamoyl)-2-[(3-(4,4-dimethyl-cyclohex-1-enyl)-phenyl]-ethyl}-benzoic acid (0.6 g, 1.03 mmol) and EDCl (290 mg, 1.55 mmol) in DMF (7 mL), added HOBt (230 mg, 1.55 mmol), N,N-diisopropylethylamine (0.4 g, 2.06 mmol), and taurine (250 mg, 0.5 mmol). The resulting mixture was stirred for 14 h. The reaction solvent was removed under reduced pressure. The residue mixture was dissolved in 0.1 N NaHCO$_3$ and acetonitrile, purified by column chromatography on a C-18 silica gel flash chromatography column, eluting with an acetonitrile-water gradient. Sodium-2-(4-{2-(4'-chloro-2'-methyl-biphenyl-4-ylcarbamoyl)-2-[3-<4,4-dimethyl-cyclohex-1-enyl)-phenyl]-ethyl}-benzoylamino-ethane sulfonic acid was obtained as a white solid. $^1$H NMR (500 MHz, DMSO-$d_6$): 9.98 (s, 1H), 8.25 (bs, 1H), 7.50 (d, J=3.0 Hz, 2H), 7.43 (d, J=5.5 Hz, 2H), 7.19-6.98 (m, 11H), 3.85 (bs, 1H), 3.32-3.18 (m, 3H), 2.83 (d, J=14.0 Hz, 2H), 2.47 (bs, 2H), 2.23 (bs, 1H), 2.03 (s, 3H), 1.42-1.15 (m, 6H), 0.81 (s, 3H), 0.78 (s, 3H); LC-MS m/z=685 [C$_{39}$H$_{42}$N$_2$O$_5$S]$^+$; Anal Calcd: (MF:C$_{398}$H$_{42}$N$_2$O$_3$SNa+3.3 H$_2$O) Calcd: C:60.94, H:6.37, N:3.64 Found: C: 60.82, H:6.08, N:3.57. Chiral HPLC conditions: Regis-Whelk-01-786615, (S,S)10/100 250×10 mm T=23° C.; mobile phase=100% ACN/(5% NH$_4$CO$_3$,+H$_2$O) flow rate=1.0 mL/min; detection=254 nm retention time in min: 12.39 min (enantiomeric excess: 95.1%)

Example 3: Ammonium, 2-(S)-{4-[2-[4-(4-(R)-tert-butylcyclohex-1-enyl)phenyl]-2-(4'-chloro-2'-methylbiphenyl-4-ylcarbamoyl)-ethyl]-benzoylamino}-ethanesulfonate Step 1: [4-(4-tert-Butyl-cyclohex-1-enyl)-phenyl]-acetic acid ethyl ester

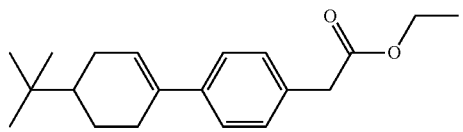

To a mixture of 4-bromophenyl ethyl acetate (780 mg), 4-t-butyl-cyclohexen-1-yl boronic acid (897 mg), PdCl$_2$(P(o-tolyl)$_3$)$_2$ (254 mg) in THF: ethanol: water (8 mL: 4 mL: 2 mL), added sodium carbonate (1.377 g). The sealed flask was heated at 140° C. for a 5 min period. The heterogeneous mixture was treated with an excess of 1M aqueous hydrochloric acid and filtered through a celite pad. The organic solvents were removed under reduced pressure and the residue partitioned between ethyl acetate and water. The organic phase was washed with water and saturated aqueous sodium chloride, dried over magnesium sulfate and chromatographed on silica gel using an ethyl acetate/hexanes gradient. The product was obtained as a yellow oil.
$^1$H NMR (500 MHz, CDCl$_3$): 7.32 (d, J=8 Hz, 2H), 7.20 (d, J=8 Hz, 2H), 6.10 (m, 1H), 4.12 (q, J=7 Hz, 2H), 3.57 (s, 2H), 2.52-2.32 (m, 2H), 2.26-2.18 (m, 1H), 2-1.9 (m, 2H), 1.38-1.2 (m, 5H), 0.91 (s, 9H).

Step 2: [4-((1R,2R,4S)-4-tert-Butyl-1,2-dihydroxy-cyclohexyl)-phenyl]-acetic acid ethyl ester and [4-((1R,2R,4R)-4-tert-Butyl-1,2-dihydroxy-cyclohexyl)-phenyl]-acetic acid ethyl ester

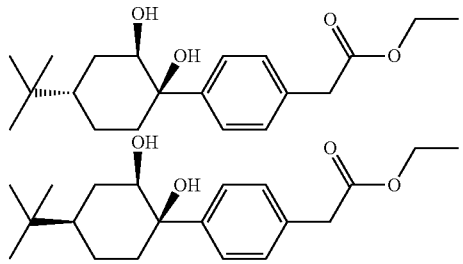

A mixture of AD-mix-beta (6.512 g, J. Org. Chem 57, 2768 (1992)) and methanesulfonamide (443 mg, 4.66 mmol) in tert-butanol (23 mL) and water (28 mL) was cooled to 2-4° C. To this mixture. [4-<4-tert-Butyl-cyclohex-1-enyl)-phenyl]-acetic acid ethyl ester (1.4 g, 4.66 mmol) in tert-Butanol (5 mL) was added slowly while making sure that the temperature remained in the 2-4° C. range. The mixture was stirred at the same temperature for a period of 4 days then quenched by adding sodium sulfite (1.5 g/mmol starting material) in water (20 mL). After allowing to warm to room temperature, the reaction mixture was stirred an additional 1 h before being partitioned between ethyl acetate and water. The organic phase was washed with brine then concentrated under reduced pressure to afford crude material which was purified by chromatography on silica gel, eluting with an ethyl acetate/hexanes gradient. Two products were obtained. In agreement with the report from Hamon et al (Tetrahedron 57.9499 (2001)) they were assigned as follows:

First eluting product: [4-((1R,2R,4R)-4-tert-Butyl-1,2-dihydroxy-cyclohexyl)-phenyl]-acetic acid ethyl ester $^1$H NMR (500 MHz. CDCl$_3$): 7.46 (m, 2H), 7.28 (m, 2H), 4.16 (q, J=7 Hz, 2H), 3.99 (m, 1H), 3.61 (s, 2H), 2.59 (m, 1H), 1.92 (m, 2H), 1.64-1.46 (m, 5H), 1.27 (t, J=7 Hz, 3H), 0.93 (s, 9H).

Second eluting product: [4-((1R,2R,4S)-4-tert-Butyl-1,2-dihydroxy-cyclohexyl)-phenyl]-acetic acid ethyl ester, $^1$H NMR (500 MHz, CDCl$_3$): 7.51 (m, 2H), 7.30 (m, 2H), 4.36 (m, 1H), 4.16 (q, J=7 Hz, 2H), 3.62 (s, 2H), 2.74 (m, 1H), 2.26 (m, 1H), 2.20 (m, 1H), 2.07 (m, 1H), 1.92 (m, 1H), 1.75 (m, 1H), 1.27 (t, J=7 Hz, 3H), 1.17 (m, 2H), 0.80 (s, 9H).

Step 3-[4-((3R,6R,7R)-6-tert-Butyl-2-thioxo-tetrahydro-benzo[1,3]dioxol-3-yl)-phenyl]-acetic acid ethyl ester

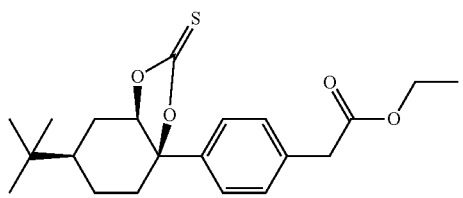 [SMILES: CCOC(=O)Cc1ccc([C@]23CC[C@@H](C(C)(C)C)C[C@H]2OC(=S)O3)cc1]

A solution of [4-((1R,2R,4R)-4-tert-Butyl-1,2-dihydroxy-cyclohexyl)-phenyl]-acetic acid ethyl ester (319 mg, 0.95 mmol) and thiocarbonyl diimidazole (309 mg, 1.91 mmol) in THF (15 mL) was refluxed under N$_2$ overnight. The reaction mixture was partitioned between ethyl acetate and brine, dried over Na$_2$SO$_4$ and concentrated under reduced pressure. Purification of the residue by chromatography on silica gel using an ethyl acetate/hexanes gradient afforded 297 mg of product.

1H NMR (500 MHz, CDCl$_3$): 7.31 (m, 4H), 4.97 (dd, J=9 Hz, J=7 Hz, 1H), 4.13 (q, J=7 Hz, 2H), 3.59 (s, 2H), 2.53-2.48 (m, 1H), 2.40-2.31 (m, 1H), 1.90-1.72 (m, 2H), 1.40-1.15 (m, 6H), 0.91 (s, 9H).

Step 4: [4-((R)-4-tert-Butyl-cyclohex-1-enyl)-phenyl]-acetic acid ethyl ester

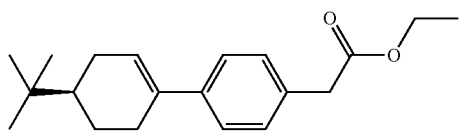 [SMILES: CCOC(=O)Cc1ccc(C2=CC[C@H](C(C)(C)C)CC2)cc1]

A solution of [4-((3aR,6S,7aR)-6-tert-Butyl-2-thioxo-tetrahydro-benzo[1,3]dioxol-3a-yl)-phenyl]-acetic acid ethyl ester (297 mg, 0.80 mmol) in triethylphosphite (3 mL) was slowly added to a solution of triethylphosphite (10 mL) heated to reflux—rate of addition was such that the reaction temperature exceeded 150° C. After refluxing overnight, the solvent was removed under vacuum and the crude reaction mixture was loaded on top of a silica column and eluted with an ethyl acetate/hexanes gradient to afford 145 mg of the title compound, 1H NMR (500 MHz, CDCl$_3$): 7.32 (d, J=8 Hz, 2H), 7.20 (d, J=8 Hz, 2H), 6.10 (m, 1H), 4.12 (q, J=7 Hz, 2H), 3.57 (s, 2H), 2.52-2.32 (m, 2H), 2.26-2.18 (m, 1H), 2-1.9 (m, 2H), 1.38-1.2 (m, 5H), 0.91 (s, 9H).

Determination of the enantiomeric excess: A sample of the product was treated with an excess of aqueous 1M NaOH:ethanol:water (1:2:3 ratio by volume) and heated at 125° C. for a 5 min period. The organic solvents were removed under reduced pressure and the residue was partitioned between ethyl acetate and 1M aqueous HCl. The organic phase was washed with water and a saturated sodium chloride solution and then dried over magnesium sulfate. The enantiomeric excess of the product was determined to be >99% by chiral HPLC utilizing a Chiral Technologies Chiralpak AD-H 250 mm×4.6 mm column, eluting at a 1.0 mL/min flow rate using a mixture of hexanes: isopropanol: methanesulfonic acid in a 95:5:0.1 ratio. The sample was dissolved at 1 mg/mL in ethanol prior to injection. The retention time observed was 6.2 min.

Step 5: 4-{2-[4-(4-(R)-tert-Butylcyclohex-1-enyl)-phenyl]-2-ethoxycarbonyl-ethyl}-benzoic acid tert-butyl ester

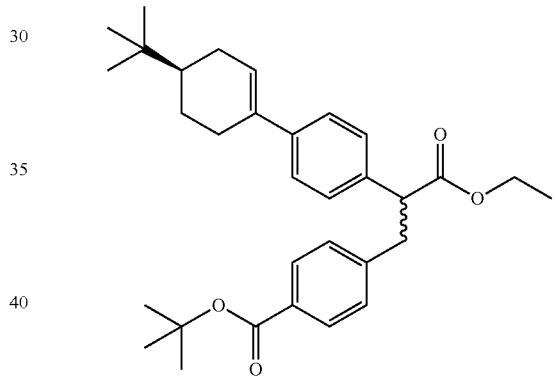

To [4-((R)$_4$-tert-Butyl-cyclohex-1-enyl)-phenyl]-acetic acid ethyl ester (95 mg, 0.32 mmol) in anhydrous THF (5 mL), chilled to −78° C., was added 380 uL (0.38 mmol) of 1M lithium hexamethyldisilazane in THF. The resulting solution was stirred for 1 hr before 4-Bromomethylbenzoic acid tert-butyl ester (94 mg, 0.35 mmol) was added. The reaction mixture was allowed to warm to rt overnight then quenched with saturated NH$_4$Cl solution. Alter partitioning between ethyl acetate and brine the organic portion was dried over Na$_2$SO$_4$ and concentrated under reduced pressure. Purification of the crude by prep TLC (Analtech, 2 mm silica plates) using an hexane/ethyl acetate (10:1) gave 63 mg of product. $^1$H NMR (500 MHz. CDCl$_3$): 7.83 (d, J=8.5 Hz, 2H), 7.31 (d, J=8.5 Hz, 2H), 7.20 (d, J=8 Hz, 2H), 7.14 (d, J=8 Hz, 2H), 6.12 (m, 1H), 4.03 (q, J=7 Hz 2H), 3.80 (t, J=8.5 Hz, 1H), 3.41 (dd, J=14, 8.5 Hz, 1H), 3.03 (dd, J=14, 7 Hz, 1H), 2.56-2.4 (m, 2H), 2.35-2.2 (m, 1H), 2.05-1.9 (m, 2H), 1.56 (s, 9H), 1.36-1.2 (m, 2H), 1.11 (t, J=7 Hz, 3H), 0.89 (s, 9H).

Step 6: 4-{2-[4-(4-(R)-tert-Butylcyclohex-1-enyl)-phenyl]-2-carboxy-ethyl}-benzoic acid tert-butyl ester

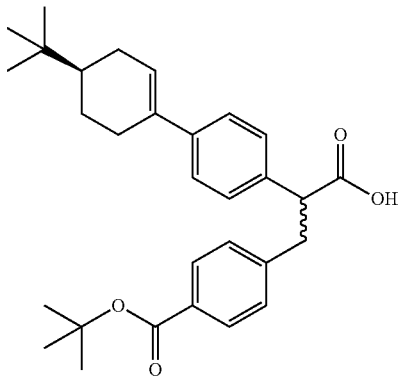 [SMILES: CC(C)(C)OC(=O)c1ccc(CC(C(=O)O)c2ccc(C3=CC[C@H](C(C)(C)C)CC3)cc2)cc1]

To 4-{2-[4-(4-(R)-tert-Butylcyclohex-1-enyl)-phenyl]-2-ethoxycarbonyl-ethyl}-benzoic acid tert-butyl ester (63 mg, 0.13 mmol) dissolved in a solution of THF (3 mL), MeOH (1 mL) and water (1 mL) was added lithium hydroxide (27 mg, 0.64 mmol). The solution was stirred at rt for 5 hrs then neutralized with 3M $KH_2PO_4$ and extracted with ethyl acetate. The organic portion was washed with brine, dried over $Na_2SO_4$ and concentrated under vacuum to afford crude material which was used without further purification.

Step 7: 4-{2-[4-(4-(R)-tert-Butylcyclohex-1-enyl)-phenyl]-2-(4'-chloro-2'-methylbiphenyl-4-ylcarbamoyl)-ethyl]-benzoic acid tert-butyl ester

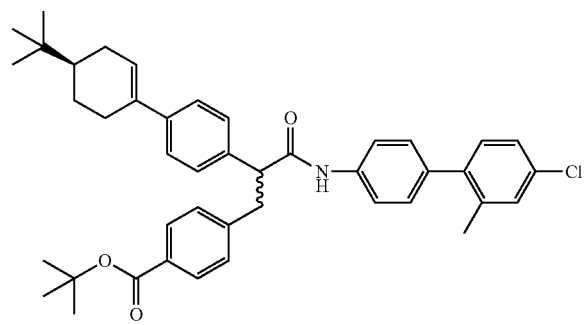 [SMILES: Cc1cc(Cl)ccc1-c1ccc(NC(=O)C(Cc2ccc(C(=O)OC(C)(C)C)cc2)c2ccc(C3=CC[C@H](C(C)(C)C)CC3)cc2)cc1]

To 4-{2-[4-(4-(R)-tert-Butylcyclohex-1-enyl)-phenyl]-2-carboxy-ethyl}-benzoic acid tert-butyl ester (697 mg, 1.51 mmol) in anhydrous dichloromethane (30 mL) was added oxalyl chloride (650 uL, 7.53 mmol) and 3 drops of DMF. The resulting solution was stirred at rt for 1 hr before being concentrated under vacuum. The residue was co-evaporated with toluene (1×5 mL) then dissolved in toluene again (20 mL). To the mixture was added 4-chloro-2-methylbiphenyl-4-ylamine (361 mg, 1.66 mmol) and DIPEA (1.3 mL, 7.53 mmol). The resulting mixture was refluxed for 90 min, diluted with ethyl acetate and washed with saturated $NaHCO_3$. The organic portion was dried over $Na_2SO_4$ and concentrated under vacuum to afford crude material which was crystallized from MeOH to afford a white solid (590 mg). Removing the solvent and purification of the residue by chromatography on silica gel using an ethyl acetate/hexanes gradient afforded an additional 137 mg of product. 1H NMR (500 MHz, DMSO-$d_6$): 10.16 (s, 1H), 7.78 (d, J=8 Hz, 2H), 7.59 (d, J=8.5 Hz, 2H), 7.4-7.32 (m, 7H), 7.21 (d, J=8 Hz, 2H), 7.15 (d, J=8 Hz, 2H), 6.14 (m, 1H), 4.03 (dd, J=9.7 Hz, 1H), 3.48 (dd, J=13.5, 9.5 Hz, 1H), 3.41 (dd, J=13.5, 6.5 Hz, 1H), 2.4-2.3 (m, 1H), 2.2-2.15 (m, 4H), 1.96-1.9 (m, 2H), 1.52 (s, 9H), 1.32-1.2 (m, 2H), 0.89 (s, 9H).

Step 8: 4-{2-[4-(4-(R)-tert-Butylcyclohex-1-enyl)-phenyl]-2-(4'-chloro-2'-methylbiphenyl-4-ylcarbamoyl)-ethyl]-benzoic acid

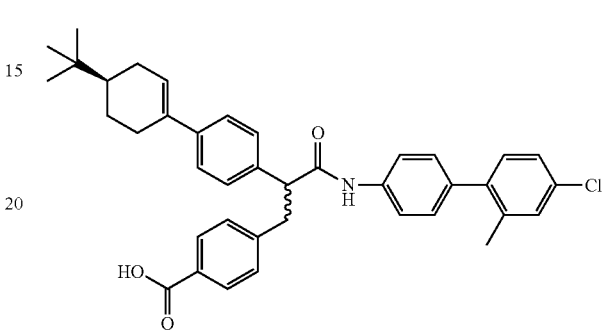

To 4-{2-[4-<4-(R)-tert-Butylcyclohex-1-enyl)-phenyl]-2-(4'-chloro-2'-methylbiphenyl-4-ylcarbamoyl)-ethyl]-benzoic acid tert-butyl ester (727 mg, 1.1 mmol) was added 4N HCl/dioxane (30 mL), water (5 mL) and conc. HCl (1 mL). The resulting solution was stirred at rt overnight. The excess solvent was removed under vacuum and the residue co-evaporated with toluene to afford the desired crude product as a gummy oil. The crude material was used the next step without further purification.

Step 9: Sodium, 2-{4-[2-[4-(4-(R)-tert-butylcyclohex-1-enyl)-phenyl]-2-<4'-chloro-2'-methylbiphenyl-4-ylcarbamoyl)-ethyl]-benzoylamino}-ethanesulfonate

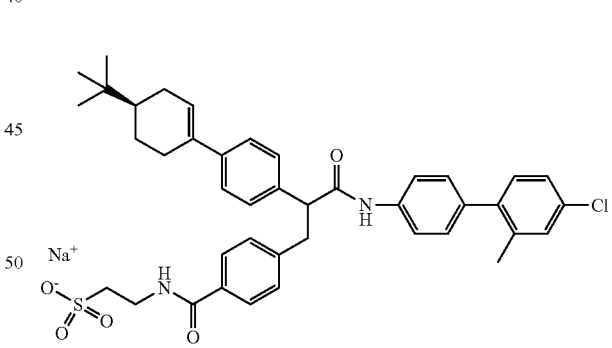

To crude 4-{2-[4-(4-(R)-tert-Butylcyclohex-1-enyl)-phenyl]-2-(4'-chloro-2'-methyl biphenyl-4-ylcarbamoyl)-ethyl]-benzoic acid (assumed 1.1 mmol) in DMF (25 mL) was added EDC (316 mg, 1.65 mmol), HOBt (252 mg, 1.65 mmol), taurine (206 mg, 1.65 mmol) and DIPEA (550 uL, 3.29 mmol). The resulting mixture was stirred at rt overnight. The excess solvent was removed under vacuum and to the oily residue was added excess lN HCl. After decanting off the excess lN HCl, the residue was dissolved in acetonitrile/MeOH, made basic with saturated $NaHCO_3$ and purified using reverse phase flash chromatography and eluting with an acetonitrile/water gradient. The sodium salt was obtained as a white solid. LCMS: 711.6 [M−H]⁻

Step 10: Ammonium, 2-(S)-{4-[2-[4-(4-(R)-tert-butylcyclohex-1-enyl)-phenyl]-2-(4'-chloro-2'-methylbiphenyl-4-ylcarbamoyl)-ethyl]-benzoylamino}-ethanesulfonate

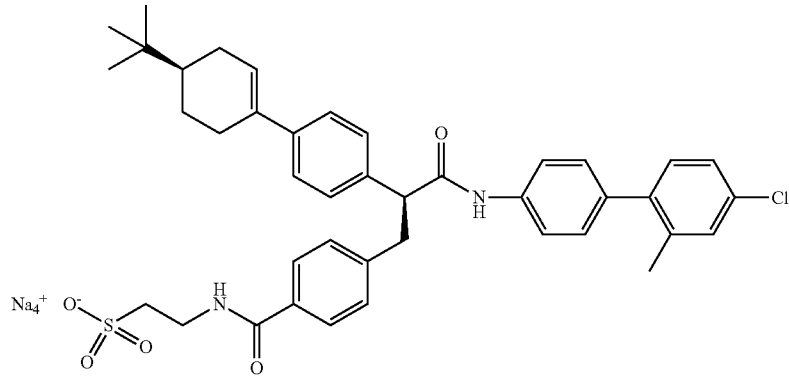

Sodium, 2-{4-[2-[4-(4-(R)-tert-butylcyclohex-1-enyl)-phenyl]-2-(4'-chloro-2'-methylbiphenyl-4-ylcarbamoyl)-ethyl]-benzoylamino}-ethanesulfonate (obtained on Step 8 above), was dissolved in DMF. The product was subjected to preparative HPLC on a Pirkle Covalent (S,S)-Whelk-01 column (250 mm×10 mm), eluting at 10 mL/min with a gradient of acetonitrile and 5 mM ammonium bicarbonate. The title compound was the first of the two diastereomers to elute. Conditions for the determination of the enantiomeric excess by HPLC: Regis-Whelk-01-786615. (S,S)10/100 250×10 mm T=23° C.; mobile phase=100% ACN/(5% Phosphate pH=7.0, ACN) flow rate=1.0 mL/min; detection=254 nm. Retention time in min: 18.22 min (enantiomeric excess: 99.1%). $^1$H NMR (500 MHz, CD$_3$OD): 7.71 (d, J=8.5 Hz, 2H), 7.51 (d, J=8.5 Hz, 2H), 7.4-7.25 (m, 7H), 7.20 (d, J=8.5 Hz, 2H), 7.13 (d, J=8.5 Hz, 2H), 3.97 (dd, J=9.5, 6.5 Hz, 1H), 3.78 (t, J=6.5 Hz, 2H), 3.52 (dd, J=13.5, 9.5 Hz, 1H), 3.10 (dd, J=13.5, 6.5 Hz, 1H), 3.07 (t, J=6.5 Hz, 2H), 2.5-2.3 (m, 2H), 2.3-2.20 (m, 4H), 2.1-1.95 (m, 2H), 1.38 (s, 10H), 0.94 (s, 9H).

Example 4: Ammonium, 2-(R)-{4-[2-[4-(4-(R)-tert-butylcyclohex-1-enyl)-phenyl]-2-(4'-chloro-2'-methylbiphenyl-4-ylcarbamoyl)-ethyl]-benzoylamino}-ethanesulfonate The title compound was the second compound eluting from the chiral chromatography reported in Example 3. Step 9. Conditions for the determination of the enantiomeric excess by HPLC: Regis-Whelk-01-786615. (S,S)10/100 250×10 mm T=23° C.; mobile phase=100% ACN/(5% Phosphate pH=7.0, ACN) flow rate=1.0 mL/min; detection=254 nm. Retention time in min: 23.55 min (enantiomeric excess: 99.5%). $^1$H NMR (500 MHz, CD$_3$OD): 7.71 (d, J=8.5 Hz, 2H), 7.51 (dd, J=8.5 Hz, 2H), 7.4-7.25 (m, 7H), 7.20 (d, J=8.5 Hz, 2H), 7.13 (d, J=8.5 Hz, 2H), 3.97 (dd, J=9.5, 6.5 Hz, 1H), 3.78 (t, J=6.5 Hz, 2H), 3.52 (dd, J=13.5, 9.5 Hz, 1H), 3.10 (dd, J=13.5, 6.5 Hz, 1H), 3.07 (t, J=6.5 Hz, 2H), 2.5-2.3 (m, 2H), 2.3-2.20 (m, 4H), 2.1-1.95 (m, 2H), 1.38 (s, 10H), 0.94 (s, 9H).

Example 5: Ammonium, 2-(S)-{4-[2-[4-(4-(S)-tert-butylcyclohex-1-enyl)-phenyl]-2-4'-chloro-2'-methylbiphenyl-4-ylcarbamoyl)-ethyl]-benzoylamino}-ethanesulfonate Step 1: [4-((S)-4-tert-Butyl-cylclohex-1-enyl)-phenyl]-acetic acid ethyl ester

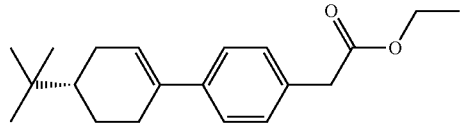

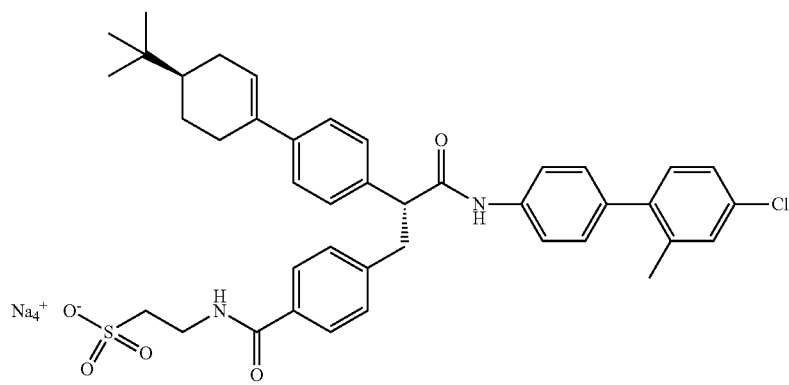

Utilizing the second eluting diol in Example 3, Step 2, the chiral alkene shown above was obtained after utilizing the methods described in Example 3, Steps 3 and 4. $^1$H NMR (500 MHz, CDCl$_3$): 7.32 (d, J=8 Hz, 2H), 7.20 (d, J=8 Hz, 2H), 6.10 (m, 1H), 4.12 (q, J=7 Hz, 2H), 3.57 (s, 2H), 2.52-2.32 (m, 2H), 2.26-2.18 (m, 1H), 2-1.9 (m, 2H), 1.38-1.2 (m, 5H), 0.91 (s, 9H).

Determination of the enantiomeric excess: A sample of the product was treated with an excess of aqueous 1M NaOH:ethanol:water (1:2:3 ratio by volume) and heated at 125° C. for a 5 min period. The organic solvents were removed under reduced pressure and the residue was partitioned between ethyl acetate and 1M aqueous HCl. The organic phase was washed with water and a saturated sodium chloride solution and then dried over magnesium sulfate. The enantiomeric excess of the product was determined to be >99% by chiral HPLC utilizing a Chiral Technologies Chiralpak AD-H 250 mm×4.6 mm column, eluting at a 1.0 mL/min flow rate using a mixture of hexanes: isopropanol: methane sulfonic acid in a 95:5:0.1 ratio. The sample was dissolved at 1 mg/mL in ethanol prior to injection. The retention time observed was 5.6 min.

Step 2: Ammonium, 2-(S)-{4-[2-[4-(4-(S)-tert-butylcyclohex-1-enyl)-phenyl]-2-(4'-chloro-2'-methyl-biphenyl-4-ylcarbamoyl)-ethyl]-benzoylamino}-ethanesulfonate

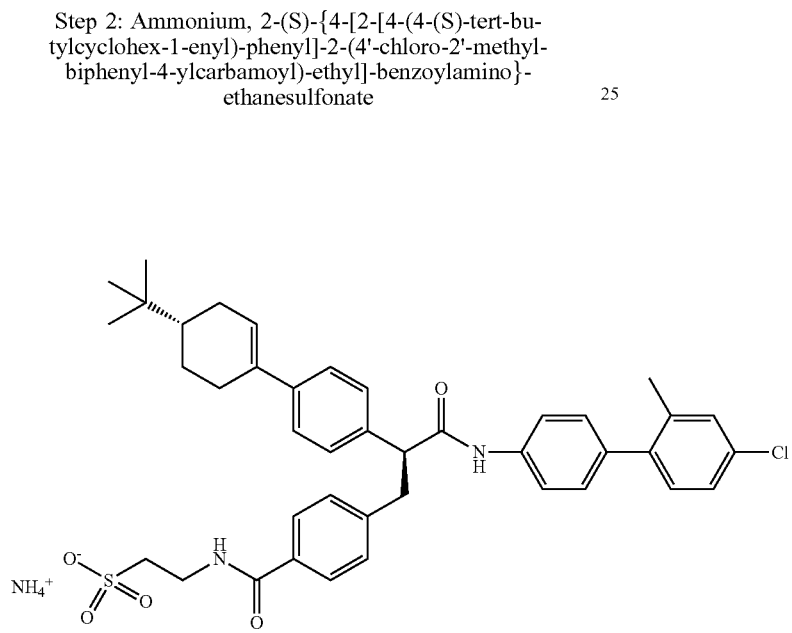

[4-((S)-4-tert-Butyl-cyclohex-1-enyl)-phenyl]-acetic acid ethyl ester (Step 1, above), was utilized to yield the title compound through the sequence illustrated in Example 3. Steps 5-10. The title compound eluted first among the two possible diastereomers after preparative HPLC on a Pirkle Covalent (S, S)-Whelk-01 column (250 mm×10 mm), eluting at 10 mL/min with a gradient of acetonitrile and 5 mM ammonium bicarbonate.

Conditions for the determination of the enantiomeric excess by HPLC: The sample was diluted in ethanol at a 1 mg/mL concentration. It was injected into an HPLC system equipped with a Regis-Whelk-01-786615, (S,S)10/100 250× 10 mm column kept at 23° C. The column was eluted with a gradient of two solvents A and B for a 30 min period. The composition of the gradient ranged from 40% A to 65% A over this period (with the balance of the solvent being B). Solvent A was acetonitrile, solvent B was a mixture of 5% acetonitrile and 95% water containing 5 mM potassium phosphate monobasic (pH 6.8). The product was detected by UV at 254 nm. Retention time in min: 18.23 min (enantiomeric excess: >99.5%). $^1$H NMR (500 MHz. CD$_3$OD): 7.71 (d, J=8.5 Hz, 2H), 7.51 (d, J=8.5 Hz, 2H), 7.4-7.25 (m, 7H), 7.20 (d, J=8.5 Hz, 2H), 7.13 (d, J=8.5 Hz, 2H), 3.97 (dd, J=9.5, 6.5 Hz, 1H), 3.78 (t, J=6.5 Hz, 2H), 3.52 (dd, J=13.5, 9.5 Hz, 1H), 3.10 (dd, J=13.5, 6.5 Hz, 1H), 3.07 (t, J=6.5 Hz, 2H), 2.5-2.3 (m, 2H), 2.3-2.20 (m, 4H), 2.1-1.95 (m, 2H), 1.38 (s, 10H), 0.94 (s, 9H).

Example 6: Ammonium, 2-(R)-{4-[2-[4-(4-(S)-tert-butylcyclohex-1-enyl)-phenyl]-2-4'-chloro-2'-methylbiphenyl-4-ylcarbamoyl)-ethyl]-benzoylamino}-ethanesulfonate

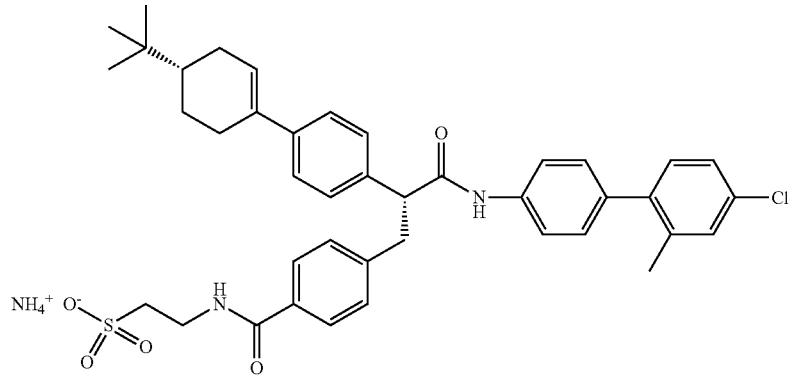 [SMILES: [NH4+] ; Cc1cc(Cl)ccc1-c1ccc(NC(=O)[C@H](Cc2ccc(C(=O)NCCS(=O)(=O)[O-])cc2)c2ccc(C3=CC[C@@H](C(C)(C)C)CC3)cc2)cc1]

The title compound was the second compound eluting from the chiral chromatography reported in Example 5, Step 2. Ille sample was diluted in ethanol at a 1 mg/mL concentration. It was injected into an HPLC system equipped with a Regis-Whelk-01-786615, (S,S)10/100 250×10 mm column kept at 23° C. The column was eluted with a gradient of two solvents A and B for a 30 min period. The composition of the gradient ranged from 40% A to 65% A over this period (with the balance of the solvent being B). Solvent A was acetonitrile, solvent B was a mixture of 5% acetonitrile and 95% water containing 5 mM potassium phosphate monobasic (pH 6.8). The product was detected by UV at 254 nm. Retention time in min:23.41 min (enantiomeric excess: >99.5%). $^1$H NMR (500 MHz, CD$_3$OD): 7.71 (d, J=8.5 Hz, 2H), 7.51 (d, J=8.5 Hz, 2H), 7.4-7.25 (m, 7H), 7.20 (d, J=8.5 Hz, 2H), 7.13 (d, J=8.5 Hz, 2H), 3.97 (dd, J=9.5, 6.5 Hz, 1H), 3.78 (t, J=6.5 Hz, 2H), 3.52 (dd, J=13.5, 9.5 Hz, 1H), 3.10 (dd, J=13.5, 6.5 Hz, 1H), 3.07 (t, J=6.5 Hz, 2H), 2.5-2.3 (m, 2H), 2.3-2.20 (m, 4H), 2.1-1.95 (m, 2H), 1.38 (s, 10H), 0.94 (s, 9H).

Using the methods described in Examples 1-6, the following compounds were synthesized.

Example 7: Sodium-2-(R)-4-[2-(4'-chloro-2'-methyl-biphenyl-4-ylcarbamoyl)-2-[(4-(3,3-dimethyl-but-1-enyl)-phenyl]-ethyl}-benzoyl amino ethane sulfonic acid 2H), 7.33-7.12 (m, 11H), 6.25 (dd, J=16.2, 3.6 Hz, 2H), 3.98 (t, J=8.4 Hz, 1H), 3.49-3.38 (m, 3H), 3.0 (dd, J=6.3, 7.8 Hz, 1H), 2.61 (t, J=7.8 Hz, 2H), 2.17 (s, 3H), 1.06 (s, 3H): LC-MS m/z=657 [C$_{37}$H$_{38}$N$_2$O$_5$SClNa+H]$^+$; HPLC conditions: Waters Atlantis C-18 OBD 4.6×150 mm; mobile phase=ACN/(H$_2$O:0.1 TFA) flow rate=1.0 mL/min; detection=UV@254, 220 nm retention time in min: 12.33; Anal Calcd: (MF: C$_{37}$H$_{38}$N$_2$O$_5$SClNa+1.2H$_2$O) Calcd: C:63.23, H:5.79. N:3.99 Found: C: 63.02, H:5.89, N:4.15.

Chiral HPLC conditions: The sample was diluted in ethanol at a 1 mg/mL concentration. It was injected into an HPLC system equipped with a Regis-Whelk-01-786615, (S,S)10/100 250×10 mm column kept at 23° C. The column was eluted with a gradient of two solvents A and B for a 30 min period. The composition of the gradient ranged from 40% A to 65% A over this period (with the balance of the solvent being B). Solvent A was acetonitrile, solvent B was a mixture of 5% acetonitrile and 95% water containing 5 mM potassium phosphate monobasic (pH 6.8). The product was detected by UV at 254 nm. Retention time in min: 14.08 min (enantiomeric excess: >97.06%)

Example 8: Sodium-2-(S)-4-[2-(4'-chloro-2'-methyl-biphenyl-4-ylcarbamoyl)-2-[(4-(3,3-dimethyl-but-1-enyl)-phenyl]-ethyl}-benzoyl amino ethane sulfonic acid

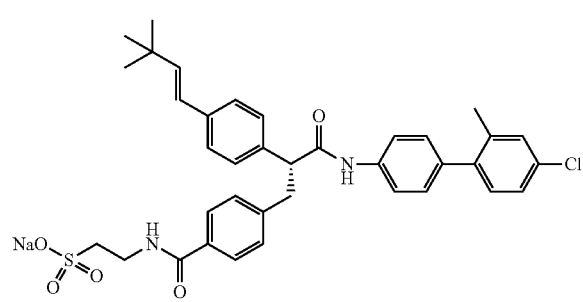

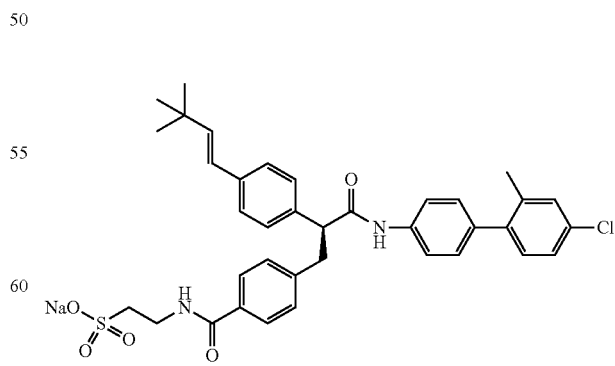

$^1$H NMR (500 MHz, DMSO-d$_6$): 10.14 (s, 1H), 8.39 (t, J=9.8 Hz, 1H), 7.61 (d, J=8.7 Hz, 2H), 7.55 (d, J=8.7 Hz, $^1$H NMR (500 MHz, DMSO-d$_6$): 10.14 (s, 1H), 8.39 (t, J=9.8 Hz, 1H), 7.61 (d, J=8.7 Hz, 2H), 7.56 (d, J=6.6 Hz, 2H), 7.33-7.12 (m, 11H), 6.26 (dd, J=16.2, 3.6 Hz, 2H), 3.98

(t, J=9.9 Hz, 1H), 3.49-3.39 (m, 3H), 3.0 (dd, J=6.3, 7.8 Hz, 1H), 2.61 (t, J=7.2 Hz, 2H), 2.17 (s, 3H), 1.05 (s, 3H); LC-MS m/z=657 [$C_{37}H_{38}N_2O_5SClNa+H$]⁻; HPLC conditions: Waters Atlantis C-18 OBD 4.6×150 mm; mobile phase=ACN/($H_2O$:0.1TFA) flow rate=1.0 mL/min; detection=UV@254, 220 nm retention time in min: 12.33; Anal Calcd: (MF: $C_{37}H_{38}N_2O_5SClNa+1.5H_2O$) Calcd: C:62.75, H:5.83, N:3.96 Found: C: 62.65, H:5.81, N:4.13.

Chiral HPLC conditions: The sample was diluted in ethanol at a 1 mg/mL concentration. It was injected into an HPLC system equipped with a Regis-Whelk-01-786615, (S,S)10/100 250×10 mm column kept at 23° C. The column was eluted with a gradient of two solvents A and B for a 30 min period. The composition of the gradient ranged from 40% A to 65% A over this period (with the balance of the solvent being B). Solvent A was acetonitrile, solvent B was a mixture of 5% acetonitrile and 95% water containing 5 mM potassium phosphate monobasic (pH 6.8). The product was detected by UV at 254 nm. Retention time in min: 17.69 min (enantiomeric excess: >97.4%).

Example 9: 2-(4-{(R)-2-(4'-Chloro-2'-methyl-biphenyl-4-ylcarbamoyl)-2-[4-(4,4-dimethyl-cyclohex-1-enyl)-phenyl]-ethyl}-benzoylamino)-ethanesulfonic acid

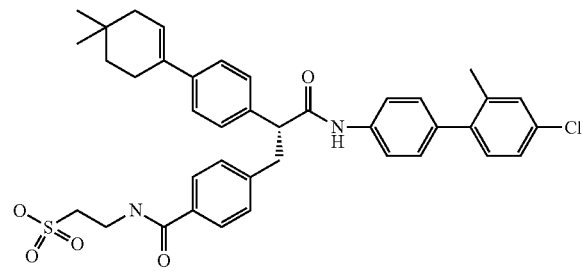 [SMILES: Cc1cc(Cl)ccc1-c1ccc(NC(=O)[C@H](Cc2ccc(C(=O)NCCS(=O)(=O)O)cc2)c2ccc(C3=CCC(C)(C)CC3)cc2)cc1]

¹H NMR (500 MHz. DMSO-$d_6$): δ 10.14 (s, 1H), 8.40 (t, J=2.8 Hz, 1H), 7.64 (d, J=8.4 Hz, 2H), 7.57 (d, J=8.9 Hz, 2H), 7.37-7.14 (m, 11H), 6.07 (bs, 1H), 4.0 (t, J=5.5 Hz, 1H), 3.47-3.45 (m, 3H), 3.0-2.85 (m, 1H), 2.62 (t, J=4.2 Hz, 2H), 235 (t, J=1.2 Hz, 2H), 2.18 (s, 3H), 1.95 (t, J=2.8 Hz, 2H), 1.46 (t, J=2.8 Hz, 2H), 0.91 (s, 6H). LC-MS m/z=685 [$C_{39}H_{40}N_2O_4SCl+H$]⁻.

Chiral HPLC conditions: The sample was diluted in ethanol at a 1 mg/mL concentration. It was injected into an HPLC system equipped with a Regis-Whelk-01-786615, (S,S) 10/100 250×10 mm column kept at 23° C. The column was eluted with a gradient of two solvents A and B for a 30 min period. The composition of the gradient ranged from 40% A to 70% A over this period (with the balance of the solvent being B). Solvent A was acetonitrile, solvent B was a mixture of 5% acetonitrile and 95% water containing 5 mM ammonium bicarbonate (pH adjusted to 6.5 with $CO_2$). The product was detected by UV at 254 nm. Retention time in min: 17.92 min (enantiomeric excess: 99.5%).

Example 10: 2-(4-{(S)-2-(4'-Chloro-2'-methyl-biphenyl-4-ylcarbamoyl)-2-[4-(4,4-dimethyl-cyclohex-1-enyl)-phenyl]-ethyl}-benzoylamino)-ethanesulfonic acid

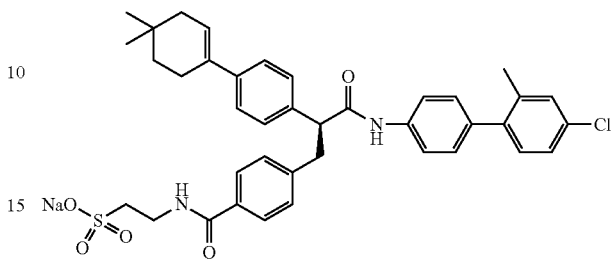

¹H NMR (500 MHz. DMSO-$d_6$): δ 10.15 (s, 1H), 8.40 (t, J=2.8 Hz, 1H), 7.64 (d, J=8.4 Hz, 2H), 7.57 (d, J=8.9 Hz, 2H), 7.37-7.11 (m, 11H), 6.07 (bs, 1H), 4.0 (t, J=5.5 Hz, 1H), 3.47-3.45 (m, 3H), 3.0-2.85 (m, 1H), 2.62 (t, J=8.4 Hz, 2H), 2.35 (t, J=1.2 Hz, 2H), 2.18 (s, 3H), 1.95 (t, J=2.8 Hz, 2H), 1.46 (t, J=2.8 Hz, 2H), 0.91 (s, 6H). LC-MS m/z=684 [$C_{39}H_{40}N_2O_4SCl$]⁺.

Chiral HPLC conditions: The sample was diluted in ethanol at a 1 mg/mL concentration. It was injected into an HPLC system equipped with a Regis-Whelk-01-786615, (S,S)10/100 250×10 mm column kept at 23° C. The column was eluted with a gradient of two solvents A and B for a 30 min period. The composition of the gradient ranged from 40% A to 70% A over this period (with the balance of the solvent being B). Solvent A was acetonitrile, solvent B was a mixture of 5% acetonitrile and 95% water containing 5 mM ammonium bicarbonate (pH adjusted to 6.5 with $CO_2$). The product was detected by UV at 254 nm. Retention time in min: 13.87 min (enantiomeric excess: 97.6%).

Example 11: Sodium-2-[4-(S)-2-(4'-tert-butyl-biphenyl-4-yl)-2-(4'-chloro-2'-methyl-phenyl-carbamoyl-ethyl}-benzoylamino-ethane sulfonic acid

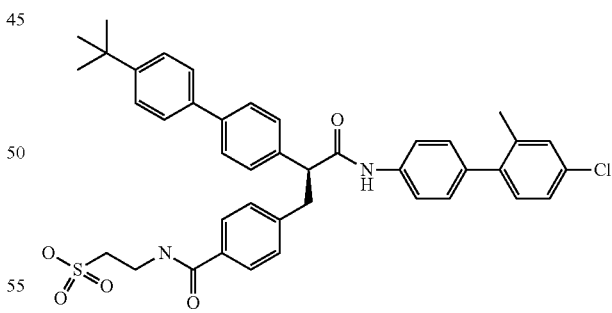

¹H NMR (500 MHz, DMSO-$d_6$): δ 7.70 (d, J=6.0 Hz, 2H), 7.57-7.47 (m, 11H), 7.33 (d, J=8.4 Hz, 2H), 7.21-7.13 (m, 4H), 4.0 (t, J=6.0 Hz, 1H), 3.74 (t, J=13.5 Hz, 2H), 3.53 (dd, J=6.3, 3.0 Hz, 1H), 3.15 (dd, J=6.6, 2.8 Hz, 1H), 3.06 (t, J=6.9 Hz, 2H), 2.20 (s, 3H), 1.34 (s, 9H). LC-MS m/z=709 [$C_{35}H_{36}N_2O_5SClNa$]⁺.

Chiral HPLC conditions: The sample was diluted in ethanol at a 1 mg/mL concentration. It was injected into an HPLC system equipped with a Regis-Whelk-01-786615, (S,S)10/100 250×10 mm column kept at 23° C. The column Example 13: Sodium-2-[4-(R)-2-(4'-tert-butyl-biphenyl-4-yl)-2-(2',4',6'-trimethyl-biphenyl-4-ylcarbamoyl)-ethyl}-benzoylamino-ethane sulfonic acid

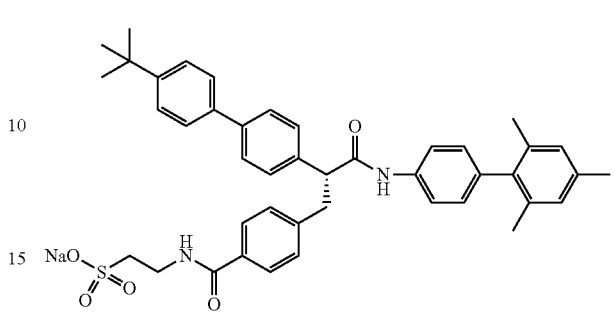

$^1$H NMR (500 MHz, DMSO-d$_6$): δ 7.65 (d, J=7.5 Hz, 2H), 7.51 (d, J=8.0 Hz, 2H), 7.48-7.43 (m, 11H), 7.38 (d, J=8.4 Hz, 2H), 7.28 (d, J=8.4 Hz, 2H), 6.92 (d, J=8.5 Hz, 2H), 6.80 (s, 1H), 3.97 (t, J=6.5 Hz, 1H), 3.71 (t, J=7.0 Hz, 2H), 3.50 (dd, J=9.0, 13.5 Hz, 1H), 3.08 (dd, J=6.6, 13.5 Hz, 1H), 2.99 (t, J=6.5 Hz, 2H), 2.19 (s, 3H), 1.86 (s, 6H), 1.28 (s, 9H). LC-MS m/z=702 [C$_{43}$H$_{45}$N$_2$O$_5$SCl]$^+$; Anal Calcd: (MF: C$_{43}$H$_{45}$N$_2$O$_5$SClNa+1.2H$_2$O+0.1 NaHCO$_3$) Calcd: C:68.57, H:6.34, N:3.71 Found: C: 68.24, H:5.98, N:3.58.

Chiral HPLC conditions: The sample was diluted in ethanol at a 1 mg/mL concentration. It was injected into an HPLC system equipped with a Regis-Whelk-01-786615, (S,S)10/100 250×10 mm column kept at 23° C. The column was eluted with a gradient of two solvents A and B for a 30 min period. The composition of the gradient ranged from 40% A to 70% A over this period (with the balance of the solvent being B). Solvent A was acetonitrile, solvent B was a mixture of 5% acetonitrile and 95% water containing 5 mM ammonium bicarbonate (pH adjusted to 6.5 with CO$_2$). The product was detected by UV at 254 nm. Retention time in min: 28.908 min (enantiomeric excess: >98.79%).

was eluted with a gradient of two solvents A and B for a 30 min period. The composition of the gradient ranged from 40% A to 70% A over this period (with the balance of the solvent being B). Solvent A was acetonitrile, solvent B was a mixture of 5% acetonitrile and 95% water containing 5 mM ammonium bicarbonate (pH adjusted to 6.5 with CO$_2$). The product was detected by UV at 254 nm. Retention time in min: 23.87 min (enantiomeric excess: 99.5%).

Example 12: Sodium-2-[4-(R)-2-(4'-tert-butyl-biphenyl-4-yl)-2-(4'-chloro-2'-methyl-phenyl-carbamoyl)-ethyl}-benzoylamino-ethane sulfonic acid

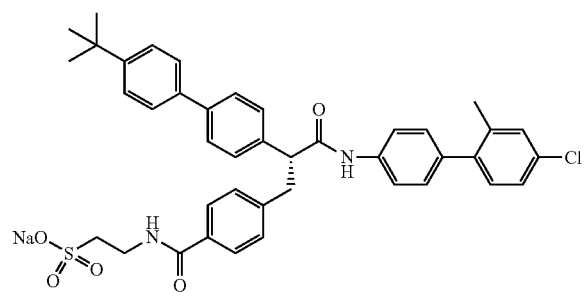

$^1$H NMR (500 MHz, DMSO-<4): δ 7.70 (d, J=6.0 Hz, 2H), 7.57-7.47 (m, 11H), 7.33 (d, J=8.4 Hz, 2H), 7.21-7.13 (m, 4H), 4.0 (t, J=6.0 Hz, 1H), 3.74 (t, J=13.5 Hz, 2H), 3.53 (dd, J=6.3, 3.0 Hz, 1H), 3.15 (dd, J=6.6, 2.8 Hz, 1H), 3.06 (t, J=6.9 Hz, 2H), 2.20 (s, 3H), 1.34 (s, 9H). LC-MS m/z=707 [C$_{35}$H$_{36}$N$_2$O$_5$SClNa−2]$^+$.

Chiral HPLC conditions: The sample was diluted in ethanol at a 1 mg/mL concentration. It was injected into an HPLC system equipped with a Regis-Whelk-01-786615, (S,S)10/100 250×10 mm column kept at 23° C. The column was eluted with a gradient of two solvents A and B for a 30 min period. The composition of the gradient ranged from 40% A to 70% A over this period (with the balance of the solvent being B). Solvent A was acetonitrile, solvent B was a mixture of 5% acetonitrile and 95% water containing 5 mM ammonium bicarbonate (pH adjusted to 6.5 with CO$_2$). The product was detected by UV at 254 nm. Retention time in min: 23.86 min (enantiomeric excess: >96.9%).

Example 14: Ammonium-2-(R)-(4-{2-[4'-tert-butyl-biphenyl-4-yl)-2-[3-(4,4-dimethyl-cyclohex-1-enyl)-phenyl-4-ylcarbamoyl]-ethyl}-benzoylamino-ethane sulfonic acid

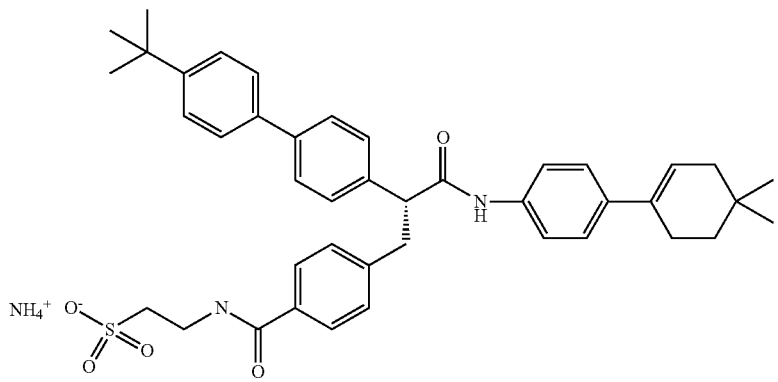 [SMILES: [NH4+] ; CC1(C)CC=C(c2ccc(NC(=O)[C@H](Cc3ccc(C(=O)NCCS(=O)(=O)[O-])cc3)c3ccc(-c4ccc(C(C)(C)C)cc4)cc3)cc2)CC1]

¹H NMR (500 MHz, DMSO-d₆): δ 10.07 (s, 1H), 8.39 (t, J=5.0 Hz, 1H), 7.64 (d, J=8.0 Hz, 2H), 7.57 (d, J=8.0 Hz, 2H), 7.54 (d, J=7.5 Hz, 2H), 7.50-7.44 (m, 6H), 7.32-7.29 (m, 4H), 6.0 (bs, 1H), 4.05 (dd, J=6.0, 8.5 Hz, 1H), 3.48 (dd, J=7.0, 12.5 Hz, 3H), 3.05 (dd, J=6.0, 13.5 Hz, 1H), 2.63 (t, J=7.0 Hz, 2H), 2.18 (bs, 3H), 1.94 (bs, 2H), 1.44 (t, J=12.0 Hz, 2H), 1.29 (s, 9H), 0.90 (s, 6H). LC-MS m/z=692 [C₄₂H₄₈N₂O₅S]⁺; Anal Calcd: (MF: C₄₂H₄₈N₂O₅S+ 2.8H₂O+0.6 NH₃) Calcd: C:66.94, H:7.41. N:4.83 Found: C: 66.90, H:7.20, N:4.44.

Chiral HPLC conditions: The sample was diluted in ethanol at a 1 mg/mL concentration. It was injected into an HPLC system equipped with a Regis-Whelk-01-786615, (S,S)10/100 250×10 mm column kept at 23° C. The column was eluted with a gradient of two solvents A and B for a 30 min period. The composition of the gradient ranged from 40% A to 70% A over this period (with the balance of the solvent being B). Solvent A was acetonitrile, solvent B was a mixture of 5% acetonitrile and 95% water containing 5 mM ammonium bicarbonate (pH adjusted to 6.5 with CO₂). The product was detected by UV at 254 nm. Retention time in min: 13.87 min (enantiomeric excess: >99.0%).

Example 15: 2-(4-[2-(4-Benzooxazol-2-yl-phenyl-carbamoyl)-2-4-(1R,4R)-1,7,7-trimethylbicyclo[2.2.1]hept-2-en-2-yl)-phenyl]-ethyl-benzoyl amino)-ethane sulfonic acid

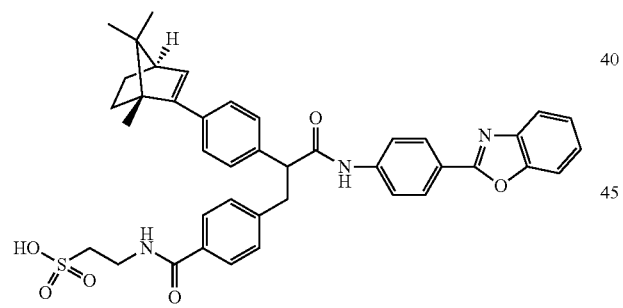

¹H NMR (500 MHz, DMSO-d₆): δ 8.13 (d, J=8.5 Hz, 2H), 7.74-7.65<m, 4H), 7.40-7.38 (m, 6H), 7.33 (d, J=8.0 Hz, 2H), 7.21 (d, J=8.0 Hz, 2H), 5.97 (d, J=3.5 Hz, 2H), 4.05 (t, J=6.0 Hz, 1H), 3.77 (t, J=6.5 Hz, 1H), 3.56-3.46 (m, 1H), 3.14 (dd, J=6.0, 14.0 Hz, 1H), 3.06 (t, J=6.5 Hz, 2H), 2.37 (t, J=3.5 Hz, 2H), 1.99-1.93 (m, 2H), 1.72-1.67 (m, 2H), 1.33-1.29 (m, 2H), 1.15-1.09 (m, 4H), 0.90 (s, 3H), 0.88 (s, 3H). LC-MS m/z=703 [C₄₁H₄₁N₃O₆S]⁺. HPLC conditions: 250×10 mm T=23° C.; mobile phase=100% ACN/(H₂O/CAN+0.1 TFA) flow rate=1.0 mL/min; detection=254, 280, 220 nm retention time in min: 7.39 min (95.0%).

Example 16: Sodium-2-[4-(R)-2-(4'-tert-butyl-biphenyl-4-yl)-2-(4'-chloro-3'-methyl-phenyl-carbamoyl)-ethyl}-benzoylamino-ethane sulfonic acid

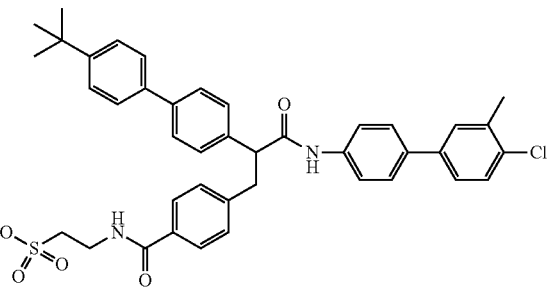

¹H NMR (500 MHz, DMSO-d₆): δ 7.71 (d, J=8.0 Hz, 2H), 7.59-7.44 (m, 13H), 7.36-7.33 (m, 4H), 4.0 (dd, J=6.0, 9.0 Hz, 1H), 3.77 (t, J=7.0 Hz, 2H), 3.56 (dd, J=9.0, 13.0 Hz, 1H), 3.14 (dd, J=6.0, 13.0 Hz, 1H), 3.06 (t, J=6.5 Hz, 2H), 2.41 (s, 3H), 1.34 (s, 9H). LC-MS m/z=731 [C)₅H₃₆N₂O₅SClNa]⁺.

Example 17: Ammonium-2-(R)-(4-{2-[4'-tert-butyl-biphenyl-4-yl)-2-(4-methyl-benzooxazol-2-yl)phenylcarbamoyl]-ethyl}-benzoylamino)-ethane sulfonic acid Step 1: 4-(4-Methyl-benzooxazol-2-yl)-phenylamine

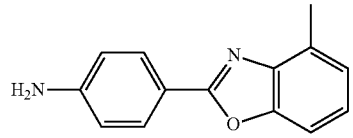 [SMILES: Cc1cccc2oc(-c3ccc(N)cc3)nc12]

To a suspension of 4-amino-benzoic acid (2.0 g, 14.5 mmol) in PPA (~85 g) was added 2-amino-m-cresol (1.8 g, 15.3 mmol). The reaction was heated to 160° C. for 14 h, then carefully quenched in aqueous sodium carbonate (~50% saturated) at room temperature. Ethyl acetate was added, and the organic layer was washed with water and brine, and dried over sodium sulfate. The crude product was obtained was subsequently purified by flash column chromatography on silica gel eluting with ethyl acetate in hexanes to afford the desired product, 4-(4-methyl-benzooxazol-2-yl)-phenylamine as a light pink solid. 1.8 g (56%). LC-MS m/z=225 [C₁₄H₁₂N₂O+H]⁺.

Step 2: The Methods Described in Examples 1-6 were Used to Generate the Title Compound from 4-(4-Methyl-benzooxazol-2-yl)-phenylamine

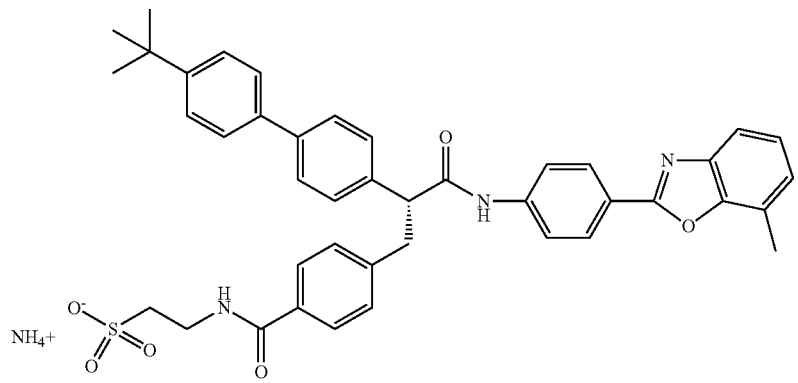 [SMILES: [NH4+] ; Cc1cccc2nc(-c3ccc(NC(=O)[C@H](Cc4ccc(C(=O)NCCS(=O)(=O)[O-])cc4)c4ccc(-c5ccc(C(C)(C)C)cc5)cc4)cc3)oc12]

1H NMR (500 MHz. DMSO-$d_6$): δ 10.48 (s, 1H), 8.41 (t, J=3.0 Hz, 1H), 8.12 (d, J=5.4 Hz, 2H), 7.77 (d, J=5.1 Hz, 2H), 7.67-7.46 (m, 11H), 7.34 (d, J=5.1 Hz, 1H), 7.25 (dd, J=4.5 Hz, 1H), 7.17 (d, J=4.8 Hz, 1H), 4.13 (t, J=6.0 Hz, 1H), 3.53-3.41 (m, 3H), 3.11 (dd, J=3.0, 6.5 Hz, 1H), 2.62 (t, J=3.9 Hz, 2H), 2.55 (s, 3H), 1.29 (s, 9H): LC-MS m/z=717[$C_{42}H_{41}N_3O_6S$]$^+$.

Chiral HPLC conditions: The sample was diluted in ethanol at a 1 mg/mL concentration. It was injected into an HPLC system equipped with a Regis-Whelk-01-786615, (S,S)10/100 250×10 mm column kept at 23° C. The column was eluted with a gradient of two solvents A and B for a 30 min period. The composition of the gradient ranged from 40% A to 70% A over this period (with the balance of the solvent being B). Solvent A was acetonitrile, solvent B was a mixture of 5% acetonitrile and 95% water containing 5 mM ammonium bicarbonate (pH adjusted to 6.5 with $CO_2$). The product was detected by UV at 254 nm. Retention time in min: 26.69 min (enantiomeric excess: >99.5%).

Example 18: Ammonium-2-(S)-(4-{2-[4'-tert-butyl-biphenyl-4-yl)-2-(4-methyl-benzooxazol-2-yl)phenylcarbamoyl]-ethyl}-benzoylamino)-ethanesulfonate This compound was generated using the methods described in Example 19. $^1$H NMR (500 MHz, DMSO-$d_6$): δ 10.48 (s, 1H), 8.41 (t, J=3.3 Hz, 1H), 8.11 (d, J=5.1 Hz, 2H), 7.78 (d, J=2.1 Hz, 2H), 7.67-7.46 (m, 11H), 7.34 (d, J=5.1 Hz, 1H), 7.25 (dd, J=4.8 Hz, 1H), 7.19 (d, J=4.8 Hz, 1H), 4.13 (t, J=6.0 Hz, 1H), 3.51-3.37 (m, 3H), 3.09 (dd, J=3.9, 4.5 Hz, 1H), 2.62 (t, J=1.2 Hz, 2H), 2.60 (s, 3H), 1.29 (s, 9H); LC-MS m/z=717[$C_{42}H_{41}N_3O_6S$]$^+$.

Chiral HPLC conditions: The sample was diluted in ethanol at a 1 mg/mL concentration. It was injected into an HPLC system equipped with a Regis-Whelk-01-786615, (S,S)10/100 250×10 mm column kept at 23° C. The column was eluted with a gradient of two solvents A and B for a 30 min period. The composition of the gradient ranged from 40% A to 70% A over this period (with the balance of the solvent being B). Solvent A was acetonitrile, solvent B was a mixture of 5% acetonitrile and 95% water containing 5 mM ammonium bicarbonate (pH adjusted to 6.5 with $CO_2$). The product was detected by UV at 254 nm. Retention time in min: 26.48 min (enantiomeric excess: >99.8%).

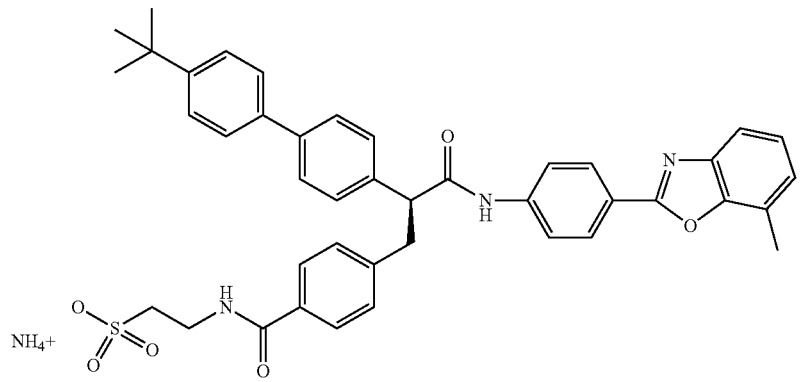 [SMILES: [NH4+] ; Cc1cccc2nc(-c3ccc(NC(=O)[C@@H](Cc4ccc(C(=O)NCCS(=O)(=O)O)cc4)c4ccc(-c5ccc(C(C)(C)C)cc5)cc4)cc3)oc12]

Example 19: 2-{4-[(R)-2-[4-(4-(cis)-tert-Butylcyclo-hexyl)-phenyl]-2-(4'-Chloro-2'-methyl-biphenyl-4-ylcarbamoyl)-ethyl]-benzoylamino}-ethanesulfonic acid

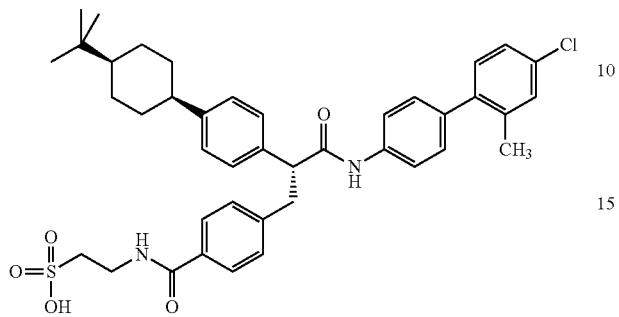

Step 1: 4-Chloromethyl benzoic acid tert-butyl ester

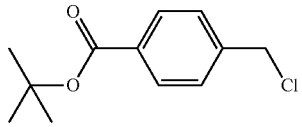

Oxalyl chloride (101 mL) was added dropwise over a 30 min period to a slurry of 4-chloromethyl benzoic acid (181.8 g) in dichloromethane (1.2 L) containing 5 mL of DMF. After the addition was complete the reaction mixture was stirred at room temperature for 24 h, concentrated under reduced pressure and then co-evaporated with toluene. To the residue was added 908 mL of MTBE and the mixture was cooled to −5° C. A solution of potassium tert-butoxide in THF (1.0 M, 1172 mL) was added dropwise ensuring that the internal temperature remained below 10° C. After the addition was complete, the reaction mixture was stirred for an additional 1 hour then treated with 500 mL of saturated sodium bicarbonate solution. After stirring 5 minutes, then settling, the organic phase was separated, washed with saturated sodium chloride solution and dried over magnesium sulfate. Concentration yielded 241.7 g (86% yield) as a dark oil. HNMR: CDCl$_3$, 1.59 ppm (s, 9H), 4.61 (s, 2H), 7.45 (d, 2H), 7.99 (d, 2H)

Step 2: 4-Iodomethyl benzoic acid tert-butyl ester

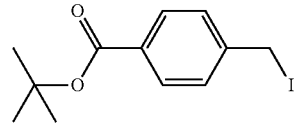

Sodium iodide (229.2 g) was added to a solution of 4-chloromethyl benzoic acid tert-butyl ester (315.2 g) in acetone (1.5 L). The reaction mixture was heated to reflux for about 2 h and then allowed to cool to room temperature. The precipitate was removed by filtration and the filtrate concentrated under reduced pressure. The residue was partitioned between water (500 mL) and MTBE (1500 mL). The organic phase was washed with saturated sodium bicarbonate and dried over magnesium sulfate. Concentration under reduced pressure afforded 442.2 g (97% yield) dark oil. HNMR: CDCl$_3$, 1.59 ppm (s, 9H), 4.47 (s, 2H), 7.42 (d, 2H), 7.91 (d, 2H)

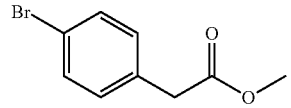

Step 3: 4-Bromophenyl acetic acid methyl ester

Sulfuric acid (56.5 mL) was very slowly added to a solution of 206.6 g of 4-bromophenyl acetic acid in methanol (800 mL). After completion of the addition, the mixture was heated to reflux for 2 h. The reflux condenser was replaced by a distillation head and 400 mL of methanol was atmospherically distilled. The temperature was the reduced to 50° C. and the reaction stirred for additional 16 h, when the mixture was then cooled to room temperature and partitioned between dichloromethane (1 L) and water (600 mL). The organic phase was washed with saturated sodium bicarbonate and dried over magnesium sulfate. Concentration under reduced pressure provided 220.1 g (98% yield) colorless oil. HNMR: CDCl$_3$, 3.59 (s, 2H), 3.70 (s, 3H), 7.16 (d, 2H), 7.45 (d, 2H)

Step 4: 4-[2-(4-Bromo-phenyl)-2-methoxycarbonyl-ethyl]-benzoic acid tert-butyl ester

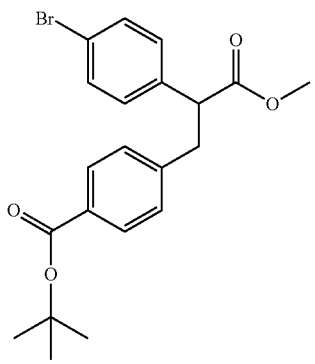 [SMILES: COC(=O)C(Cc1ccc(C(=O)OC(C)(C)C)cc1)c1ccc(Br)cc1]

A solution of 246.63 g of methyl-4-bromophenyl acetate and 342.54 g of 4-Iodomethyl benzoic acid tert-butyl ester in THF (1233 mL) was cooled to −8° C. A solution of lithium hexamethyl disilazide in THF (1185 mL, 1.0 M) was added dropwise ensuring that the temperature remain below −2° C. After the addition was complete, the reaction was allowed to proceed for ~45 min at the same temperature and then poured over a stirring mixture of ethyl acetate (2.46 L) and water (1.23 L). The organic phase was washed with saturated ammonium chloride and then with water. Dried over magnesium sulfate and concentrated under reduced pressure to obtain 430.3 g (100% yield) thick oil. HNMR: CDCl$_3$. 1.41 (s, 9H), 2.88-2.90 (m, 1H), 3.24-3.28 (m, 1H), 3.45 (s, 3H), 3.63 (t, 1H), 6.96-6.99 (m, 4H), 7.25 (d, 2H), 7.68 (d, 2H)

Step 5: (R)-2-(4-Bromo-phenyl)-3-(4-tert-butoxy-carbonyl-phenyl)-propionate (S)-2-hydroxymethyl pyrrolidinium

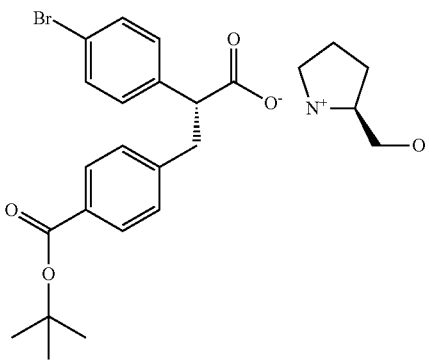 [SMILES: CC(C)(C)OC(=O)c1ccc(C[C@@H](C(=O)[O-])c2ccc(Br)cc2)cc1 ; OC[C@@H]1CCC[NH2+]1]

4-[2-(4-Bromo-phenyl)-2-methoxycarbonyl-ethyl]-benzoic acid tert-butyl ester (769 g) was dissolved in THF (5.38 L) and water (3.85 L) and treated with lithium hydroxide monohydrate (153.9 g). The reaction mixture was heated to 45° C. for approximately 1 hour. After allowing the reaction to cool to 32° C., the reaction was poured into a stirring mixture of 11.6 L of ethyl acetate and 3.9 L of 1M aqueous hydrochloric acid. The separated organic layer was washed with water, dried over magnesium sulfate and concentrated under reduced pressure. Added ethyl acetate (2.045 L) to the residue and warmed to 78° C. for ~5 min for dissolution. The mixture was allowed to cool to 68° C. and treated with (S)-(+)-prolinol (90.5 mL). The solid that precipitated after cooling to room temperature was filtered and rinsed with a cold mixture (7° C.) of 1:1 ethyl acetate: heptane (740 mL). The solid isolated (232.4 g, 35% yield) was shown to have 94% enantiomeric excess (R isomer) by chiral HPLC analysis. HNMR: CDCl$_3$, 1.57 (s, 9H), 1.67-1.74, (m, 2H), 2.64-2.69 (m, 1H), 2.76-2.81 (m, 1H), 2.94-2.99 (m, 1H), 3.14-3.19 (m, 1H), 3.32-3.39 (m, 2H), 3.60-3.67 (m, 2H), 7.14-7.19 (m, 4H), 7.35 (d, 2H), 7.80 (d, 2H). Conditions for chiral HPLC analysis Kromasil 100-5-TBB column, 250× 4.6 mm, 1 mL/min, 15% (1% AcOH/MTBE)/85% hexanes, 230/240/250 nm.

To 228 g of the product above were added 684 mL of ethyl acetate. The mixture was warmed to reflux (additional 228 mL of ethyl acetate were added when the temperature reached 69° C. for mobility) where it was held for about 10 min. The suspension was then allowed to cool to room temperature and filtered. Vacuum dried at 50° C. Product is a white solid (224.6 g, 98% yield) "R' enantiomer with enantiomeric excess of 96.9% by HPLC analysis as described above.

Step 6: 4-[(R)-2-(4-Bromo-phenyl)-2-carboxy-ethyl-]-benzoic acid tert-butyl ester

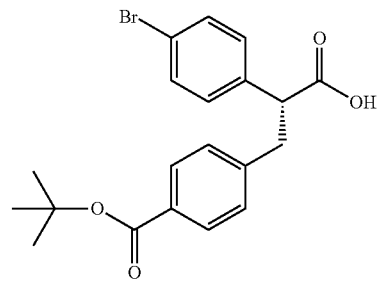 [SMILES: CC(C)(C)OC(=O)c1ccc(C[C@@H](C(=O)O)c2ccc(Br)cc2)cc1]

A stirring slurry of 216.8 g of (R)-2-(4-Bromo-phenyl)-3-(4-tert-butoxycarbonyl-phenyl)-propionate (S)-2-hydroxymethyl pyrrolidinium in 2168 mL of ethyl acetate at 21° C. was treated 1084 mL of 10% aqueous formic acid. After 20 minutes, the separated organic phase was washed with water and dried over magnesium sulfate. The ethyl acetate solution was atmospherically displaced into heptanes to yield the product as a granular solid. 166.3 g (96% yield) of white solid, enantiomeric excess ("R" enantiomer) of 96.9% by chiral HPLC analysis as described above. HNMR: CDCl$_3$, 1.50 (s, 9H), 2.96-3.00 (m, 1H), 3.32-3.37 (m, 1H), 3.73 (t, 1H), 7.03-7.08 (m, 4H), 7.35 (d, 2H), 7.76 (d, 2H)

Step 7: 4-{(R)-2-[4-(4-tert-Butyl-cyclohex-1-enyl)-phenyl]-2-carboxy-ethyl}-benzoic acid tert-butyl ester

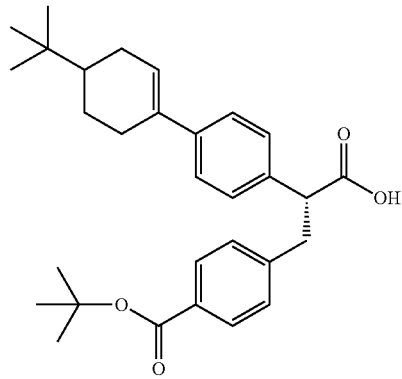 [SMILES: CC(C)(C)OC(=O)c1ccc(C[C@@H](C(=O)O)c2ccc(C3=CCC(C(C)(C)C)CC3)cc2)cc1]

A mixture of 3.1 g of 4-[(R)-2-(4-Bromo-phenyl)-2-carboxy-ethyl-]-benzoic acid tert-butyl ester (3.Step 2, above), 1.5 g of 4-t-butyl-cyclohex-1-enyl boronic acid, 644 mg of PdCl$_2$(P(o-tolyl)$_3$)$_2$, and 2.21 g of sodium carbonate in 12 mL of DME and 6 mL of ethanol and 3 mL of water was heated to reflux for a 16 h period. The reaction mixture was quenched with an excess of aqueous ammonium chloride, added ethyl acetate and the heterogeneous mixture was filtered through a celite pad. The organic phase was washed (water, saturated sodium chloride), dried over magnesium sulfate and concentrated. The residue was chromatographed on silica gel using a methanol-dichloromethane gradient to yield the carboxylic acid. HNMR (300 MHz, CDCl3, partial): 6.14 (1H, m), 1.58 (9H, s), 0.92 (9H, s). LCMS m/z=407.9 [(C$_{30}$H$_{38}$O$_4$+H)–C$_4$H$_9$]$^+$.

Step 8: 4-{(R)-2-[4-(4-(cis)-tert-Butyl-cyclohexyl) phenyl]-2-carboxy-ethyl}-benzoic acid tert-butyl ester

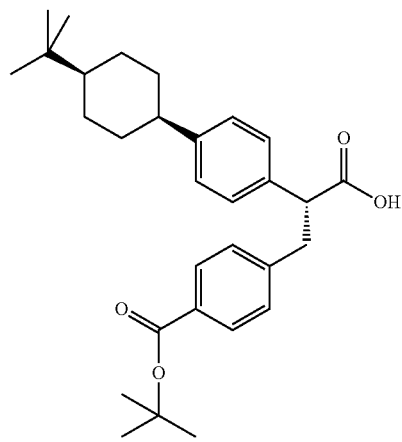 [SMILES: CC(C)(C)OC(=O)c1ccc(C[C@@H](C(=O)O)c2ccc([C@H]3CC[C@@H](C(C)(C)C)CC3)cc2)cc1]

To a solution of 4-{(R)-2-[4-(4-tert-Butyl-cyclohex-1-enyl)-phenyl]-2-carboxy-ethyl}-benzoic acid tert-butyl ester (3.0 g) in ethyl acetate (100 mL) added 10% palladium on carbon (300 mg). The mixture was stirred under a balloon filled with hydrogen, until proton NMR indicated the disappearance of the olefinic signal. The reaction was filtered through a plug of celite, and the filtrate was concentrated under reduced pressure to give a mixture of cis/trans isomers (in a ratio of 1:1, based on $^1$H NMR). The cis[1] and trons isomers were separated by reverse phase chromatography with the latter being cis (1.34 g, 2.9 mmol, 35%). $^1$H NMR (CDCl$_3$): δ 0.95 (9H, s), 1.23-1.38 (4H, m), 1.58 (9H, s), 1.88-1.98, (4H, m), 2.39-2.56 (1H, m), 3.05-3.12 (1H, m), 3.19-3.50 (1H, m), 3.82-3.90 (1H, m), 7.19-7.22 (6H, m), 8.81 (2H, d).

Based on the following reference and references within the article, the cis was assigned as described above. Garbisch, E. W.; Patterson, D. B., *J. Am. Chem. Soc.,* 1963, 85, 3228.

Step 9: 4-[(R)-2-[4-(4-(cis)-tert-Butyl-cyclohexyl)-phenyl]-2-(4'-chlor-2'-methyl-biphenyl-4-ylcarbamoyl)-ethyl]-benzoic acid tert-butyl ester

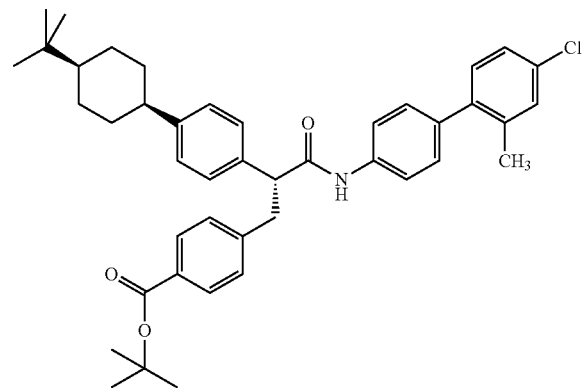 [SMILES: Cc1cc(Cl)ccc1-c1ccc(NC(=O)[C@H](Cc2ccc(C(=O)OC(C)(C)C)cc2)c2ccc([C@H]3CC[C@@H](C(C)(C)C)CC3)cc2)cc1]

To 4-{(R)-2-[4-(4-(cis)-tert-Butyl-cyclohexyl)-phenyl]-2-carboxy-ethyl}-benzoic acid tert-butyl ester (300 mg) in dichloromethane (10 mL) was added a solution of oxalyl chloride in dichloromethane (2.0M, 0.54 mL) followed by 2 drops of DMF. The reaction mixture was stirred at room temperature for 2 h and concentrated under reduced pressure. The residue was dissolved in dichloromethane (20 mL), and treated with 4'-Chloro-2'-methyl-biphenyl-4-amine (142 mg) and diisopropyl ethyl amine (0.120 mL). After stirring for 1 h at room temperature, the solvent was removed under reduced pressure and the residue treated with methanol. The white precipitated formed was washed with methanol, dried under vacuum and used without further purification in the following step.

Step 10: 4-[(R>2-[4-(4-(cis)-tert-Butyl-cyclohexyl)-phenyl]-2-(4'-chlor-2'-methyl-biphenyl-4-ylcarbamoyl)-ethyl]-benzoic acid

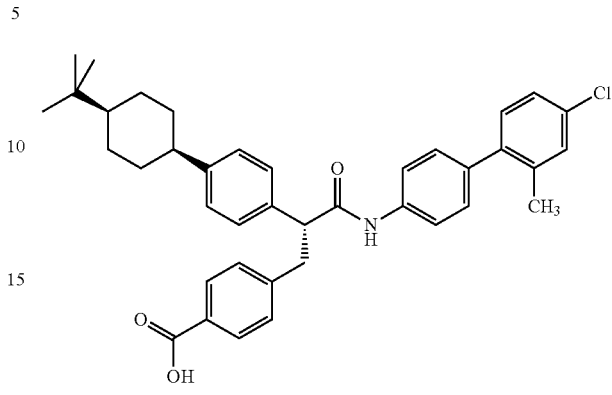

A solution of 431 mg of 4-[(R)-2-[4-(4-(cis)-tert-Butyl-cyclohexyl)-phenyl]-2-(4'-chloro-2'-methyl-biphenyl-4-yl-carbamoyl)-ethyl]-benzoic acid tert-butyl ester in dichloromethane (10 mL) was treated with trifluoroacetic acid (2 mL) and concentrated aqueous hydrochloric acid (1 mL). The resulting mixture was stirred for 16 h at room temperature. The organic phase was separated, washed with water and dried over magnesium sulfate. Concentration left a residue that was used without further purification.

Step 11: 2-{4-[(R)-2-[4-(4-(cis)-tert-Butyl-cyclohexy)-phenyl]-2-(4'-chloro-2'-methyl-biphenyl-4-ylcarbamoyl)-ethyl]-benzoylamino}-ethanesulfonic acid

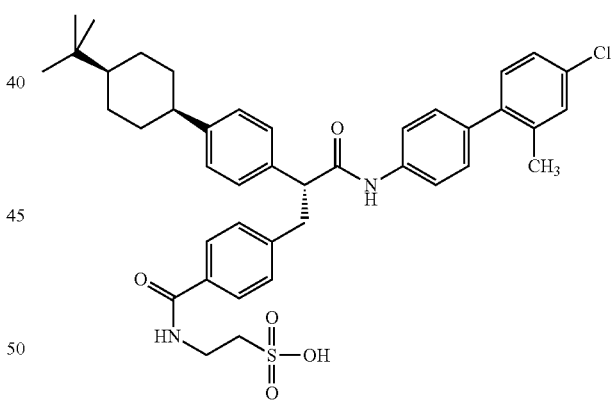

(R)-4-[2-[4-(4-(cis)-tert-Butyl-cyclohexyl)-phenyl]-2-(4'-chloro-2'-methyl-biphenyl-4-ylcarbamoyl)-ethyl]-benzoic acid (350 mg, 0.6 mmol), was taken up in 3 mL of DMF, followed by addition of HOBt (133 mg, 0.9 mmol). EDCl (132 mg, 0.7 mmol), taurine (86 mg, 0.7 mmol) and Hunig's base (374 mg, 2.9 mmol). The resulting reaction mixture was then stirred for 16 h at room temperature. The reaction solution was diluted with EtOAc (25 mL) and 10 mL of water, acidified with 2.4 N HCl. The layers were separated and the aqueous layer was extracted with EtOAc (2×20 mL). The organic extracts were combined, dried with Na$_2$SO$_4$, filtered through a frit and concentrated under reduced pressure to give a foam. The material was subjected to reverse phase HPLC purification to give the desired product as a white solid (150 mg, 36%). $^1$H NMR (CD$_3$OD): δ 0.89 (9H, s), 1.10-1.60 (6H, m), 1.80-1.90 (4H, m), 2.38 (3H, s), 2.32-2.53 (1H, m), 3.05-3.10 (4H, m), 3.47-3.55 (1h, dd), 3.77 (2H, t), 3.93-3.98 (1H, m), 7.09-7.47 (11H, m), 7.50 (2H, d), 7.70 (2H, d). Anal. Calcd. For C$_{42}$H$_{47}$ClN$_2$O$_5$S+ NH$_3$+1.2 H$_2$O; C=65.22; H=7.13; N=5.57. Found C=65.31; H=7.00; N=5.57.

Step 12. (R)-2-{4-[2-[4-(4-(trans)-tert-Butyl-cyclohexyl)-phenyl]-2-(4'-chloro-2'-methyl-biphenyl-4-ylcarbamoyl)-ethyl]-benzoylamino}-ethanesulfonic acid The trans isomer isolated from step 8, (R)-4-{2-[4-(4-(trans)-tert-Butyl-cyclohexyl)-phenyl]-2-carboxy-ethyl}-benzoic acid tert-butyl ester, was subjected to the procedures of steps 9-11 to give (R)-2-{4-[2-[4-(4-trans)-tert-butyl-cyclohexyl)-phenyl]-2-(4'-chloro-2'-methyl-biphenyl-4-yl-carbamoyl)-ethyl]-benzoylamino}-ethanesulfonic acid.

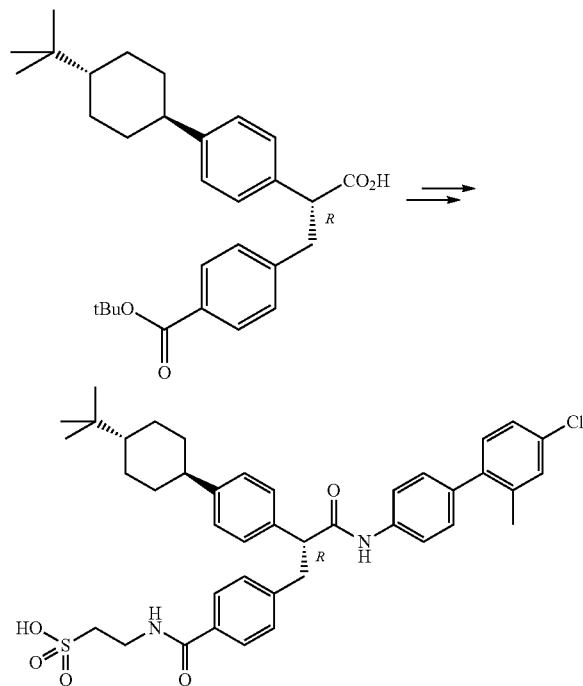

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference in their entireties as if each such publication, patent or patent application were specifically and individually indicated to be incorporated herein by reference.

What is claimed is:

1. A pharmaceutical composition comprising a pharmaceutically acceptable carrier or excipient and a compound of Formula I, or a pharmaceutically acceptable salt, solvate, or prodrug thereof:

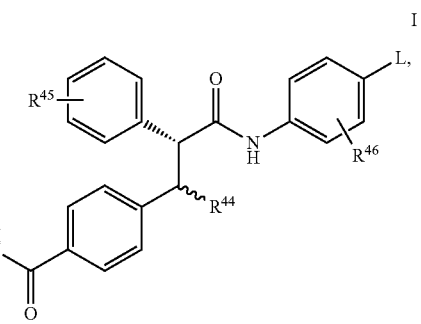

wherein
R$^{44}$ is H, CH$_3$ or CH$_3$CH$_2$;
R$^{45}$ is C$_{1-6}$-alkyl, alkenyl, alkoxy, C$_{3-6}$-cycloalkyl, C$_{3-6}$-cycloalkenyl, C$_{4-8}$-bicycloalkenyl, aryl or heteroaryl, any of which can be optionally substituted with one or more substituents selected from C$_{1-6}$alkyl, CF$_3$, F, CN or OCF$_3$;
L is phenyl, indenyl, benzoxazol-2-yl, C$_{3-6}$-cycloalkyl, C$_{4-8}$-cycloalkenyl or C$_{4-8}$-bicycloalkenyl, any of which can be optionally substituted with one or more substituents selected from F, Cl, CH$_3$, CF$_3$, OCF$_3$ or CN; and
R$^{46}$ represents one or more substituents selected from H, F, Cl, CH$_3$, CF$_3$, OCF$_3$ or CN,
wherein the amount of the compound, salt, solvate, or prodrug of Formula I is about 5 mg, about 10 mg or about 15 mg.

2. The pharmaceutical composition of claim 1, wherein R$^{44}$ is H, CH$_3$ or CH$_3$CH$_2$;
R$^{45}$ is C$_{1-6}$-alkyl, alkenyl, alkoxy, C$_{3-6}$-cycloalkyl, C$_{4-8}$-cycloalkenyl, C$_{4-8}$-bicycloalkenyl, aryl or heteroaryl, any of which can be optionally substituted with one or more substituents selected from C$_{1-6}$-alkyl, CF$_3$, F, CN or OCF$_3$;
L is phenyl, indenyl, benzoxazol-2-yl or 4,4-dimethylcyclohexenyl, any of which can be optionally substituted with one or more substituents selected from F, Cl, CH$_3$, CF$_3$, OCF$_3$ or CN; and
R$^{46}$ is H, F, Cl, CH$_3$, CF$_3$, OCF$_3$ or CN.

3. The pharmaceutical composition of claim 1, wherein L is phenyl, benzoxazol-2-yl or 4,4-dimethylcyclohexenyl, any of which can be optionally substituted with one or more substituents selected from F, Cl, CH$_3$, CF$_3$, OCF$_3$ or CN.

4. The pharmaceutical composition of claim 1, wherein L is 4-chloro-2-methylphenyl, 4-methyl-2-benzoxazolyl, 2,4,6-trimethylphenyl, 2-benzoxazolyl, 4-chloro-3-methylphenyl or 4,4-dimethylcyclohexenyl.

5. The pharmaceutical composition of claim 1, wherein R$^{44}$ is H or CH$_3$.

6. The pharmaceutical composition of claim 1, wherein R$^{45}$ is attached to the 3 (meta) or 4 (para) position.

7. The pharmaceutical composition of claim 1, wherein R$^{45}$ is alkenyl, C$_{3-6}$-cycloalkyl, C$_{4-8}$-cycloalkenyl, C$_{4-8}$-bicycloalkenyl or phenyl, any of which can be optionally substituted with one or more substituents selected from C$_{1-6}$-alkyl or CF$_3$.

8. The pharmaceutical composition of claim 1, wherein R$^{45}$ is substituted with one or more substituents independently selected from CH$_3$ and (CH$_3$)$_3$C—.

9. The pharmaceutical composition of claim 1, wherein R$^{45}$ is selected from (CH$_3$)$_3$CCH=CH—, t-butyl-cycloalkyl-, dimethyl-cycloalkyl-, t-butyl-cycloalkenyl-, dimethyl-cycloalkenyl-, bicycloalkenyl-, or t-butyl-phenyl-.

10. The pharmaceutical composition of claim 1, wherein $R^{45}$ is trans-t-butylvinyl, cis-4-t-butylcyclohexyl, trans-4-t-butylcyclohexyl, 4,4-dimethylcyclohexyl, cyclohex-1-enyl, (S)-4-t-butylcyclohex-1-enyl, (R)-4-t-butylcyclohex-1-enyl, 4,4-dimethylcyclohex-1-enyl, 4,4-diethylcyclohex-1-enyl, 4,4-diethylcyclohexyl, 4,4-dipropylcyclohex-1-enyl, 4,4-dipropylcyclohexyl, 4,4-dimethylcyclohexa-1,5-dienyl, (1R,4S)-1,7,7-trimethylbicyclo[2.2.1]-3-heptyl-2-ene, (1R,4R)-1,7,7-trimethylbicyclo[2.2.1]-2-heptyl-2-ene, 2-methyl-4-chloro-phenyl, 2,4,6-trimethylphenyl, or 4-t-butylphenyl.

11. The pharmaceutical composition of claim 1, wherein $R^{45}$ is trans-1-butylvinyl, cis-4-t-butylcyclohexyl, trans-4-t-butylcyclohexyl, 4,4-dimethylcyclohexyl, (S)-4-t-butylcyclohex-1-enyl, (R)-4-t-butylcyclohex-1-enyl, 4,4-dimethylcyclohex-1-enyl, (1R,4R)-1,7,7-trimethylbicyclo[2.2.1]-2-heptyl-2-ene or 4-t-butylphenyl.

12. The pharmaceutical composition of claim 1, wherein $R^{46}$ is H or $CH_3$.

13. The pharmaceutical composition of claim 1, wherein the compound is selected from the group consisting of

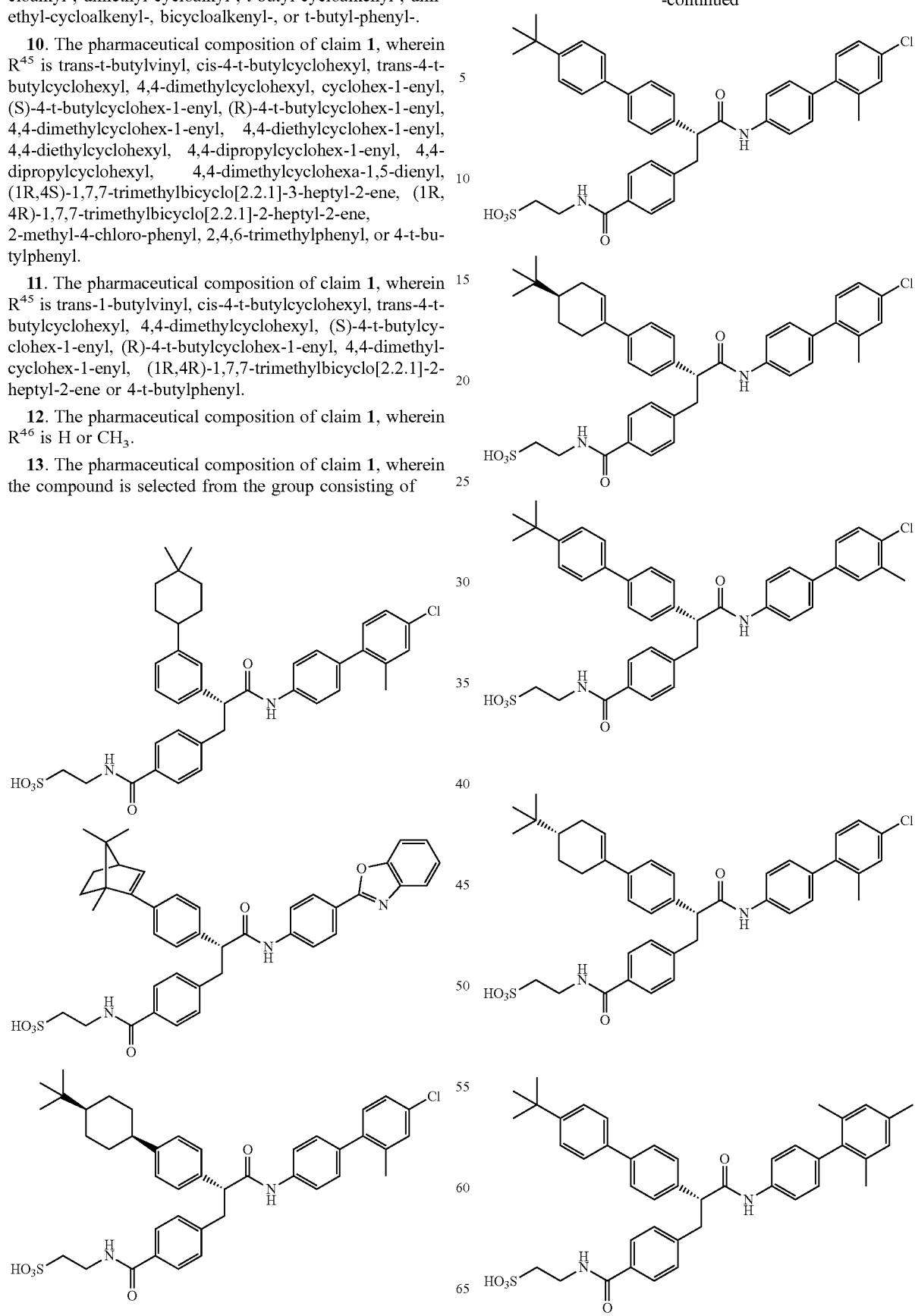

101
-continued
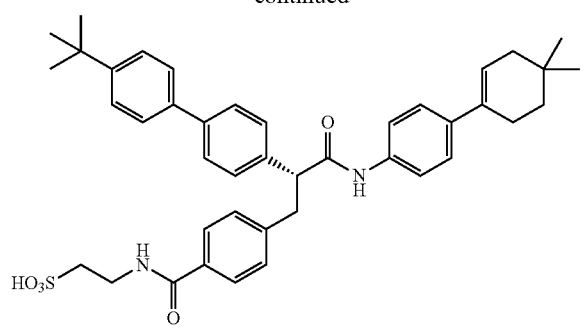
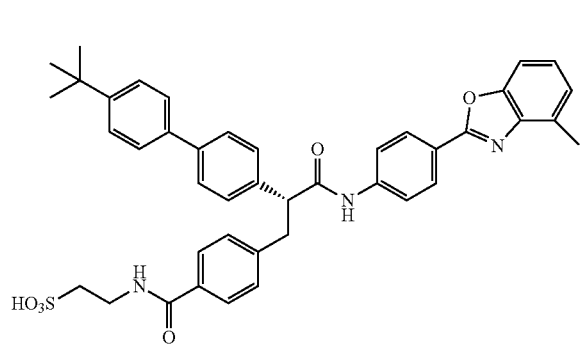
102
-continued
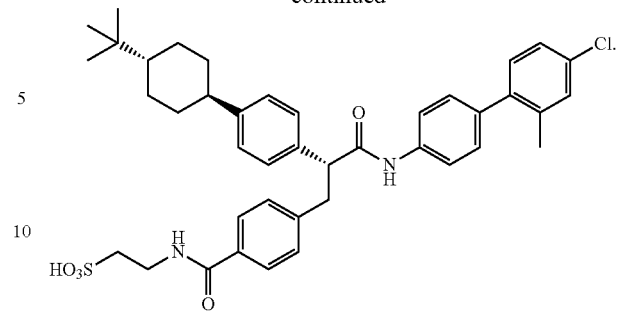
14. The pharmaceutical composition of claim 1, wherein the compound is
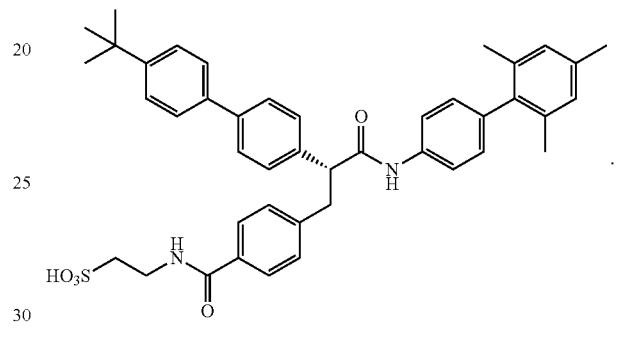
* * * * *